US009150622B2

(12) United States Patent
Boland

(10) Patent No.: US 9,150,622 B2
(45) Date of Patent: Oct. 6, 2015

(54) IMMUNE SYSTEM MODULATING COMPOSITION

(75) Inventor: Jose Antonio Vazquez Boland, Edinburgh (GB)

(73) Assignee: UNIVERSITY COURT OF THE UNIVERSITY OF EDINBURGH, Edinburgh (DE)

( * ) Notice: Subject to any disclaimer, the term of this patent is extended or adjusted under 35 U.S.C. 154(b) by 0 days.

(21) Appl. No.: 13/508,181

(22) PCT Filed: Nov. 11, 2010

(86) PCT No.: PCT/GB2010/051889
§ 371 (c)(1),
(2), (4) Date: May 15, 2012

(87) PCT Pub. No.: WO2011/058368
PCT Pub. Date: May 19, 2011

(65) Prior Publication Data
US 2012/0225078 A1 Sep. 6, 2012

(30) Foreign Application Priority Data

Nov. 11, 2009 (GB) .................................. 0919733.6

(51) Int. Cl.
| | |
|---|---|
| C07K 7/00 | (2006.01) |
| C07K 14/36 | (2006.01) |
| A61K 39/05 | (2006.01) |
| C07K 16/12 | (2006.01) |
| C12Q 1/68 | (2006.01) |
| G01N 33/569 | (2006.01) |
| A61K 39/00 | (2006.01) |

(52) U.S. Cl.
CPC ................. *C07K 14/36* (2013.01); *A61K 39/05* (2013.01); *C07K 16/1267* (2013.01); *C12Q 1/689* (2013.01); *G01N 33/56911* (2013.01); *A61K 2039/53* (2013.01); *A61K 2039/552* (2013.01); *C07K 2317/76* (2013.01); *G01N 2333/34* (2013.01); *G01N 2500/04* (2013.01)

(58) Field of Classification Search
None
See application file for complete search history.

(56) References Cited

U.S. PATENT DOCUMENTS

| | | | |
|---|---|---|---|
| 4,631,211 A | 12/1986 | Houghten | |
| 2008/0008726 A1* | 1/2008 | Taouji et al. | ................ 424/234.1 |
| 2008/0138356 A1 | 6/2008 | Friedman et al. | |

FOREIGN PATENT DOCUMENTS

WO WO-01/83519 A1 11/2001

OTHER PUBLICATIONS

Letek et al. 2008 (Evolution of the *Rhodococcus equi* vap pathogenicity island seen through comparison of host-associated vapA and vapB virulence plasmids; J. Bacteriol. 190 (17): 5797-5805).*
Letek et al. 2010 (The Genome of a Pathogenic *Rhodococcus*: Coopetive virulence underpinned by key gene acquisitions; PLOS Genetics, 6(9) e1001145).*
Greenspan et al. 1999. Defining epitopes: Its not as easy as it seems; Nature Biotechnology, 17:936-937.*
Barbey, Corinne, et al., "Proteomic Analysis and Immunogenicity of Secreted Proteins from *Rhodococcus equi* ATCC 33701", Veterinary Microbiology, vol. 135 (2009), pp. 334-345.
Vazquez-Boland, J., et al, "Havemeyer Workshop Report: *Rhodococcus equi* Comes of Age", Equine Veterinary Journal, vol. 41, No. 1 (2009), pp. 1-3.
Muscatello, G., et al, "*Rhodococcus equi* Infection in Foals: The Science of 'Rattles'", Equine Veterinary Journal, vol. 39, No. 5 (2007), pp. 470-478.
Navas, Jesus, et al., "Identification and Mutagenesis by Allelic Exchange of *choE*, Encoding a Cholesterol Oxidase from the Intracellular Pathogen *Rhodococcus equi*", Journal of Bacteriology, vol. 183, No. 16, Aug. 2001, pp. 4796-4805.
Van Der Geize, R., et al., "A Novel Method to Generate Unmarked Gene Deletions in the Intracellular Pathogen *Rhodococcus equi* Using 5-Fluorocytosine Conditional Lethality", Nucleic Acids Research, vol. 36, No. 22 (2008), 10 pages.
Hong, Yang, et al., "Site-Specific Integration of *Streptomyces* ΦC31 Integrase-Based Vectors in the Chromosome of *Rhodococcus equi*", FEMS Microbiol Lett 287 (2008), pp. 63-68.
Sanger Institute, "*Rhodococcus equi*", 2006, available at http://www.sanger.ac.uk/Projects/R_equi/, 1 page.
Lucas, S., et al., "Flp/Fap Pilin Component [Arthrobacter Chlorophenolicus a6]", NCBI Accession No. ACL40608, Jan. 2009, 1 page.
Barabote, R.D., et al., "Peptidase A24A Domain Protein [Acidothermus Cellulolyticus 11 B]", NCBI Accession No. ABK53086, May 2009, 1 page.
Shrivastava, S., et al., "Putative Baseplate J-Like Protein [Clostridium Botulinum A2 Str. Kyoto]", NCBI Accession No. ACO83959, Apr. 2009, 3 pages.
Mongodin, E.F., et al., "Type II Secretion System Protein F [Arthrobacter aurescens TC1]", NCBI Accession No. YP_948623, Apr. 2009, 1 page.

(Continued)

*Primary Examiner* — Gary Nickol
*Assistant Examiner* — Mary Lyons
(74) *Attorney, Agent, or Firm* — Winstead PC

(57) ABSTRACT

*Rhodococcus equi* (*R.equi*) has been determined to have a major adhesion factor encoded by a rpl pathogenicity island which enables host colonisation, wherein the rpl pathogenicity islandis absent from non-pathogenic *Rhodococcus* species. Further, the proteins (Rpl) encoded by the rpl pathogenicity islandhave been determined to be major immunodominant antigens. There is provided a novel diagnostic marker and vaccine candidate for *R. equi* in horses and other susceptible species.

11 Claims, 38 Drawing Sheets

(56) References Cited

OTHER PUBLICATIONS

Alteri, Christopher, J. et al., "Mycobacterium tuberculosis produces pili during human infection", PNAS, vol. 104, No. 12, Mar. 20, 2007, pp. 5145-5150.

Hillenbrand, Guenter, "International Search Report" for PCT/GB2010/051889 as mailed Mar. 25, 2011, 5 pages.

Letek, Michal, et al., "Evolution of the *Rhodococcus equi vap* Pathogenicity Island Seen through Comparison of Host-Associated *vapA* and *vapB* Virulence Plasmids", Journal of Bacteriology, vol. 190, No. 17, Sep. 2008, pp. 5797-5805.

Meijer, W.G., et al., "*Rhodococcus equi*", Jul. 2004, Veterinary Research, vol. 35, NR. 4, pp. 383-396.

Taouji, S., et al., "Immunogenecity of synthetic peptides representing linear B-cell epitopes of VapA of *Rhodococcus equi*", Vaccine, Elsevier Ltd., Great Britain, vol. 22, No. 9-10, Mar. 12, 2004, pp. 1114-1123.

\* cited by examiner

SEQ ID NO 30
SEQ ID NO 15
SEQ ID NO 31
SEQ ID NO 32

>RplA_ATCC33707 (SEQ ID NO 48):
gtgatcgtcgcagcgggcgtcggcgctgccctcctgggcatcctcgccggggcgttcgca
aacagtgcgatcgaccgcgtgcgcctggagaccgcgtgcgccgagccgaagtcgaccccc
gccaactcaaccccgccgtccccctccctacgtccgcggtggccgcccggatcgcgatg
atcgacaccatcacgcgacgacacgacatcagtgcccgccgcgtgctcgtcgaactcgca
actgccctcctgttcgtcgcgatcactctccgtctcgccgctctcgatcttctcccggca
gcaccggcctatctctggttcgccgtcgtcgggatcgccctcgccgtcatcgacatcgat
tgcaaacggctgccgaacttcctcgtcgtaccgtcgtacccgatcgtattcgcctgcctg
gcagtgggttccgtcgtcacgggcgactggtcggccctgctgcgcgccgcgatcggtgcc
gccgtcctgttcgggttctacttcgtactcgccctgatctatccggccggcatggggttc
ggcgacgtcaaacttgccggcgtcatcggcgccgtcctcgcctacctgtcgtacggcaca
ctgctcgtcggggcgtttctcgcgttcctggtggccgcactcgtcggcctgatcatcctg
gtcacccgtcgcggacggatcgggaccacgattcccttcgggccgtacatgattgcggcg
gccgtcgttgcgatcctggcagccgatccgctggcgcgtgcgtatctggactgggccgcc
gcggcctga >RplA_PAM1571 (SEQ ID NO 49):
GTGATCGTCGCAGCGGGCGTCGGCGCCGCACTCCTGGGCATCCTTGCCGGGGCATTCGCA
AACAGTGCGATCGACCGCGTGCGCCTGGAGACCGCGTGCGCCGAGCCGAGGGCGACCCCC
ACCGGCTCAACCCCGCCGCCCCCTCCCCTACGTCCGCGGTAGCCACCCGGATCGCGATG
ATCGACACCATCACGCGACGACGCGACATCAGTGCCCGCCGCATGCTCGTCGAACTCGCA
ACGGCCCTCCTGTTCGTCGCGATCACTCTCCGTCTCGCCGCTCTCGATCTTCTCCCGGCA
GCACCGGCCTATCTCTGGTTCGCCGTCATCGGGATCGCCCTCGCCGTCATCGACATCGAT
TGCAAACGGCTGCCGAACTTCCTCGTCGTACCGTCGTACCCGATCGTATTCGCCTGCCTG
GCAGTGGGTTCCGTCGTCACGGGCGACTGGTCGGCCCTGCTGCGCGCCGCGATCGGTGCC
GCCGTCCTGTTCGGGTTCTACTTCGTACTCGCCCTGATCTATCCGGCCGGCATGGGGTTC
GGCGACGTCAAACTTGCCGGCGTCATCGGCGCCGTCCTCGCCTACCTGTCGTACGGCACA
CTGCTCGTCGGGGCGTTTCTCGCGTTCCTGGTGGCCGCACTCGTGGGCCTCATCATCCTG
GTCACCCGTCGCGGTCGGATCGGGACCACGATTCCCTTCGGGCCGTACATGATTGCGGCG
GCCGTCGTTGCGATCCTCGCGGCCGATCCGCTGGCGCGTGCGTATCTGGACTGGGCCGCC
GCGGCCTGA >RplA_PAM1593 (SEQ ID NO 50):
GTGATCGTCGCAGCGGGCGTCGGCGCCGCACTCCTGGGTATCCTCGCCGGGGCGTTCGCG
AACAGTGCGATCGACCGCGTGCGCCTGGAGACCGCGTGCGCCGAGCCGAAGTCGACCCCC
ACCGGCTCAACCCCGCCGCCCCCTCCCCTGCGTCCGCGGTAGCCACCCGGATCGCGATG
ATCGACACCATCACGCGACGACGCGACATCAGTGCCCGCCGCATGCTCGTCGAACTCGCA
ACGGCCCTCCTGTTCGTCGCGATCACTCTCCGTCTCGCCGCTCTCGGTCTTCTCCCGGCA
GCACCGGCCTATCTCTGGTTCGCCGTCATCGGGATCGCCCTCGCCGTCATCGACATCGAT
TGCAAACGGCTGCCGAACTTCCTCGTCGTACCGTCGTACCCGATCGTATTCGCCTGCCTG
GCAGTGGGTTCCGTCGTCACGGGCGACTGGTCGGCCCTGCTGCGCGCCGCGATCGGTGCC
GCCGTCCTGTTCGGGTTCTACTTCGTACTCGCCCTGATCTATCCGGCCGGCATGGGGTTC
GGCGACGTCAAACTTGCCGGCGTCATCGGCGCCGTCCTCGCCTACCTGTCGTACGGCACA
CTGCTCGTCGGGGCGTTTCTCGCGTTCCTGGTGGCCGCACTCGTCGGCCTGATCATCCTG
GTCACCCGTCGCGGACGGATCGGGACCACGATTCCCTTCGGGCCGTACATGATTGCGGCG
GCCGTCGTTGCGATCCTGGCGGCCGATCCGCTGGCGCGCGCGTATCTGGACTGGGCCGCC
GCGGCCTGA

Figure 10 B

>RplB_PAM1571 (SEQ ID NO 51):
ATGAACCTCTTCTTCGCGAACCTGTACCTCATGGGCTTAGACGTCAAGGACCGTCTGACC
CGTGACGACCGCGGCGCCACTGCGGTCGAGTACGGACTGATGGTCGCCGGCATCGCGATG
GTGATCCTCATTGCGGTCTTCGCCTTCGGCGGCAAGATCAGCGAGCTGTTTAGCGGCTTC
AATTTCGACAAGCCCGCTGCGTCGGGCACGTAG

>RplB_ATCC33707 (SEQ ID NO 52):
atgaacctcttcttcgcgaacctgtacctcatgggcttagacgtcaaggaccgtctgacc
cgtgacgaccgcggcgccactgcggtcgagtacggactgatggtcgccggcatcgcgatg
gtgatcatcatcgccgtctttgccttcggcggcagactcagcaccctgttccagaacttc
aacttcgccaacccgggtaactag

Figure 10 C

>RplC_PAM1571 (SEQ ID NO 53):
ATGGGCATGCGCCGTTTTGGTTCTGATTCTGGTGCTGCCGCAGTCGAATTCGCTCTCGTT
GTTCCGATTCTGATCACACTGGTCCTCGGCATCGTGGAGTTCGGTCGGGGATACAACGTC
CAGAACGCGGTCAGCGCTGCTGCCCGCGAGGGTGCACGGACGATGGCGATCAAGAAGGAT
CCGGCGGCGGCGCGTGCCGCCGTGAAGGGCGCGGGTGTGTTCAGTCCGGCGATCACCGAT
GCGGAGATCTGCATCAGCACTTCGGGAACGCAGGGCTGTTCGGCAACGTCGTGCCCGAGC
GGAAGTACCGTGACGCTCACGGTCAGCTATCCACTCGAGTACATGACGGGACTCTTTCCC
GGTAAGCCGACGCTCACCGGCACGGGGGTCATGCGATGCGGTGGGTGA

>RplC_ATCC33707 (SEQ ID NO 54):
gtgatcatgaagcgcctcacttccgattcaggggtcgccgcagtcgaattcgctctcgtc
gttccgatcctgatcacactggtcctcggcatcgtcgagttcggtcggggatacaacgtc
cagaacgcggtcagcgctgctgcccgcgagggtgcacggacgatggcgatcaagaaggat
ccggcggcggcgcgtgccgccgtgaagggcgcgggtgtgttcagtccggcgatcaccgat
gcggagatctgcatcagcacttcgggctcgcagggctgttcggcaacgtcgtgtccgagc
ggaagtaccgtgacgctcacggtcagctatccactcgagtacatgacgggactctttccc
ggtaagccgacgctcaccggcacgggggtcatgcgatgcggtgggtga >RplC_PAM1953 (SEQ ID NO 55):
ttgcgttccgattcaggggtcgccgcagtcgaattcgctctcgtcgttccgatcctgatc
acactggtcctcggcatcgtggagttcggtcggggttacaacgtccagaacgcggtcagc
gctgctgcccgcgagggtgcacggacgatggcgatcaagaaggatccggcggcggcgcgt
gctgccgtgaagggcgcgggtgtgttcagtccggcgatcaccgatgcggagatctgcatc
agcacttcgggaacgcagggctgttcggcaacgtcgtgtccgagcggaagtaccgtgacg
ctcacggtcagctatccactcgagtacatgacgggactctttcccggtaagccgacgctc
accggcacgggggtcatgcgatgcggtgggtga

Figure 10 D (i)

>RplD_PAM1593 (SEQ ID NO 56):
ATGCGGTGGGTGAGGTCTCGCATGTCTAATGACGAGCGCGGGGTCGTCGCCGTGCTCGTC
GCGATCCTCATGGTCGTGCTCCTGGGATGTGCTGCGATCTCGGTCGACATCGGTGCGAAC
TATGTCGTCAAACGTCAGTTGCAGAACGGGGCCGATGCGGCTGCGCTCGCCGTAGCTCAG
GAATCCAGTTGCAAGGCAGGATCTTCCGCCTCATCCGTGTCGAGCCTTGTCCAGGCGAAC
GTCAACAGCTCGTCGGCTTCAAGTGCGGCGGTGATCGACGGTGTGAAGCGGAAGGTGACG
GTCACTGCGTCGGCGGTGGGTGACGACGGCCTCGCCGGCCGGAGGAACGTGTTCGCTCCG
GTCCTCGGAGTCGACCGCAGCGAGATCTCGGCGTCTGCGACTGCAAGCTGCGTGTTTCCC
CTCGGGGGGACCGCGGAACTCCCGCTCACGTTCCACAAGTGCCATTTCGACGAATCCCGC
AGTCTGGACGTGAAGATCCTCGTCGCCTACAACGTGACGGCGCCGCGCTGCAACGGAACC
TCGGGAAATGCGGCACCGGGCAATTTCGGCTGGCTGCAGGGGGCGAACGGTCGATGCCCG
GCGAAGATCGACGCCGCCGTCTATGCAACACCGGGCGACACCGGTAACAACATTCCGGGG
CCGTGCAAGGACACCATCAAGCAGTTTCAGAATGCCGTCGTCCGGGTCCCGATCTACGAC
GTCGCAGGTGGAACCGGAAGCGGTGGATGGTTTCACGTCGTCGGTTTGGCTGCCTTCAAG
ATTCAGGGCTACCGGCTGAGCGGCAACCCGGAGTTCAACTGGAACAACGATGTTCACGGG
GCGCTGAGTTGCACCGGCAGCTGTCGCGGCATCATCGGCACCTTCGTGAAAATTGTCAGC
CTCGATTCGGATCTGACGCCGGGAGGGATCGATTTCGGCGTGAGTACGATCAGCTTGCTC
GATTAG

>RplD_ATCC33707 (SEQ ID NO 57):
atgcggtgggtgaggtctcgcatgtcgaatgacgagcgcggggtcgtcgccgtgttcgtc
gcgatcctcatggtcgtgctcctgggatgtgctgcgatctcggtcgacatcggtgcgaac
tatgtcgtcaaacgtcagttgcagaacggggccgatgcggctgcgctcgccgtagctcag
gaatccagttgcaaggcaggatcttccgcctcatccgtgtcgaggcttgtccaggcgaac
gtcaacagctcgtcggcttcaagtgcggcggtgatcgacggtgtgaagcggaaggtgacg
gtcactgcgtcggcggtgggtgacgacggcctcgccggccggaggaacgtgttcgctccg
gtcctcggagtcgaccgcagcgagatctcggcgtctgcgactgcaagctgcgtgtttccc
ctcggggggaccgcggaactcccgctcacgttccacaagtgccatttcgacgaatcccgc
agtctggacgtgaagatcctcgtcgcctacaacgtgacggcgccgcgctgcaacggaacc
tcgggaaatgcggcaccgggcaatttcggctggctacaggggtgaacggtcgatgcccg
gcgaagatcgacgcggccgtctatgcaacaccgggcgacaccggtaacaacattccgggg
ccgtgcaaggacaccatcaagcagtttcagaatgccgtcgtccgggtcccgatctacgac
gtcgcaggtggaaccggaagcggtggatggtttcacgtcgtcggtttggctgccttcaag
attcagggctaccggctgagcggcaacccggagttcaactggaacaacgatgttcacgga
gcgctgagttgcaccggcagctgtcgcggcatcatcggcaccttcgtgaaaattgtcagc
ctcgattcggatctgacgccgggagggatcgatttcggcgtgagtacgatcagcttgctc
gattag

Figure 10 D (ii)

```
>RplD_PAM1571 (SEQ ID NO 58)
ATGCGGTGGGTGAGGTCTCGCATGTCTAATGACGAGCGCGGGGTCGTCGCCGTGCTCGTC
GCGATCCTCATGGTCGTGCTCCTGGGATGTGCTGCGATCTCGGTCGACATCGGTGCGAAC
TATGTCGTCAAACGTCAGTTGCAGAACGGGGCCGATGCGGCTGCGCTCGCCGTAGCTCAG
GAATCCAATTGCAAGGCAGGATCTTCCGCCTCATCCGTGTCGAGCCTTGTCCAGGCGAAC
GTCAACAGCTCGTCGGCTTCAAGTGCGGCGGTGATCGACGGTGTGAAGCGGAAGGTGACG
GTCACTGCGTCGGCGGTGGGTGACGACGGCCTCGCCGGCCGGAGGAACGTGTTCGCTCCG
GTCCTCGGAGTCGACCGCAGCGAGATCTCGGCGTCTGCGACTGCAAGCTGCGTGTTTCCC
CTCGGGGGGACCGCGGAACTCCCGCTCACGTTCCACAAGTGCCATTTCGACGAATCCCGC
AGTCTGGACGTGAAGATCCTCGTCGCCTACAACGTGACGGCGCCGCGCTGCAACGGAACC
TCGGGAAATGCGGCACCGGGCAATTTCGGCTGGCTGCAGGGGGCGAACGGTCGATGCCCG
GCGAAGATCGACCCCACCGTCTATGCAACACCGGGCGACACCGGTAACAACATTCCGGGG
CCGTGCAAGGACACCATCAAGCAGTTTCAGAATGCCGTCGTCCGGGTCCCGATCTACGAC
GTCGCAGGTGGAACCGGAAGCGGTGGATGGTTTCACGTCGTCGGTTTGGCTGCCTTCAAG
ATTCAGGGCTACCGGCTGAGCGGCAACCCGGAGTTCAACTGGAACAACGATGTTCACGGG
GCGCTGAGTTGCACCGGCAGCTGTCGCGGCATCATCGGTACCTTCGTGAAAATTGTCAGC
CTCGATTCGGATCTGACGCCGGGAGGGATCGATTTCGGCGTGAGTACGATCAGCTTGCTC
GATTAG
```

Figure 10 E

>RplE_ATCC33707 (SEQ ID NO 59):
ttgagaacccgaatcattgctgcgatctgtgcgatcgttctcgcggtcgcgggaaccctc
gccctgatctcgtatgtacgcggggccgatgcccgcgccctggcgggtacacgcaccgtc
gatgtgctcgtcgccgatcagacgattccgaagaacactcccgccgattcgctcgtggga
atggttgtggtcaagaaacttccggaaatggcggtgctacccgaacgggtgaccagtctc
gaccaactgtccggcaaggtcgcgctgaccgacctcctacctggcgaacaactggtctcg
gcgcgattcgccgacccggcgaccgcccgaagtcaggaccagggaggaatccccgagggg
atgcaggaggtgacggttcttctcgagccgcaacgcgcactgggaggccacatcgcgtca
ggcgataccgtcggcgtcttcatgtccttctcgccgcccgtcaagaactacgaaacacat
ctgagattgcagaaagtgcgagtcacgcgggtccagggaacgttttccaacgccgacgaa
ggggattcggccacggtcgactcgtcgccgagccctgctcccaccgaggcctttctcgtc
tcgctggcggtcgacgtgccgatggcggagcgcgtcgttttcgccgcggagcacgggacc
atctggctttccaatgagccgctgagttcgaacgaggccggggcatccgtggtctccccg
gaaggagtgttccgatga >RplE_PAM1953 (SEQ ID NO 60):
TTGAGAACCCGAATCATTGCTGCGATCTGTGCGATCGTTCTCGCGGTCGCGGGAACCCTC
GCCCTGATCTCGTATGTACGCGGGGCCGATGCCCGCGCCCTGGCGGGTACACGCACCGTC
GATGTGCTCGTCGCCGATCAGACGATTCCGAAGAACACTCCCGCCGATTCGCTCGTGGGA
ATGGTTGTGGTCAAGAAACTTCCGGAAATGGCGGTGCTACCCGAACGGGTGACCAGTCTC
GACCAACTGTCCGGCAAGGTCGCGCTGACCGACCTCCTGCCGGGCGAACAACTGGTCTCG
GCGCGATTCGCAGACCCGGCGACCGCCCGAAGTCAGGACCAGGGAGGAATCCCCGAGGGG
ATGCAGGAGGTGACGGTTCTTCTCGAGCCCCAACGCGCACTGGGAGGCCACATCGCGCCG
GGCGATACCGTCGGCGTCTTCATGTCCTTCTCGCCGCCCGTCAAGAACTACGAAACACAT
CTGAGATTGCAGAAAGTGCGAGTCACGCGGGTCCAGGGAACGTTTTCCAACGCCGACGAA
GGGGATTCGGCCACGGTCGACTCGTCGCCGAGCCCTGCTCCCACCGAGGCCTTTCTCGTC
TCGCTGGCGGTCGACGTGCCGATGGCGGAGCGCGTCGTTTTCGCCGCGGAGCACGGGACC
ATCTGGCTTTCCAATGAGCCGCTGAGTTCGAACGAGGCCGGGGCATCCGTGGTCTCCCCG
GAAGGAGTGTTCCGATGA >RplE_PAM1571 (SEQ ID NO 61):
TTGAGAACCCGAATCATTGCTGCGATCTGTGCGATCGTTCTCGCGGTCGCGGGAACCCTC
GCCCTGATCTCGTATGTACGCGGGGCCGATGCCCGCGCCCTGGCGGGTACACGCACCGTC
GATGTGCTCGTCGCCGATCAGACGATTCCGAAGAACACTCCCGCCGATTCGCTCGTGGGA
ATGGTTGTGGTCAAGAAACTTCCGGAAATGGCGGTGCTACCCGATCGGGTGACCAGTCTC
GACCAACTGTCCGGCAAGGTCGCGCTGACCGACCTCCTGCCTGGCGAACAACTGGTCTCG
GCGCGATTCGTCGACCCGGCGACCGCCCGAAGTCAGGACCAGGGAGGAATCCCCGAGGGG
ATGCAGGAGGTGACGGTTCTTCTCGAGCCGCAACGCGCACTGGGAGGCCACATCGCGTCA
GGCGATACCGTCGGCGTCTTCATGTCCTTCTCGCCGCCCGTCAAGAACTACGAAACACAT
CTGAGATTGCAGAAAGTGCGAGTCACGCGGGTCCAGGGAACGTTCTCCAACGCCGACGAA
GGGGATTCGGCCACGGTCGACTCGTCGCCGAGCCCTGCTCCCACCGAGGCCTTTCTCGTC
TCGCTGGCGGTCGACGTGCCGATGGCGGAGCGCGTCGTTTTCGCCGCGGAGCACGGGACC
ATCTGGCTTTCCAATGAGCCGCTGAGTTCGAACGAGGCCGGGGCATCCGTGGTCTCCCCG
GAAGGAGTGTTCCGATGA

Figure 10 F (i)

>RplF_PAM1571 (SEQ ID NO 62):
ATGAGCCGCATCGTCCTGCTGACCGATCGCGACGATTTCGCCCGCCGCGTGTACCACGCC
GCGGACGGCAACCTTCTGGTGTTGCCGGCGCAGCCGGTTCCCCGGGGGCCGGCGCAGTTG
GTCGGGCTCGGCGTGACCGTGCAACCCGAAGTTCTCGTTCTCGGTCCGGACGTGCCGGAA
GTGGAGGGCCTCTCCCTCGCCGGCCGGATCGATCATTCGACGCCCGGCACCACGGTGGTT
CTGGCCAGTGATGCGGGCACCGACGTGTGGTTGCGGGCGATGCGCGCCGGCGTGCGGGAC
GTGATGTCGCCGGAGGCGGAGATCGCGGACGTTCGTGCGGTACTCGATCGAGCGGGCCAG
GCCGCACTGGCGCGACGTCAGGGGCGAGTGCACCGGCGGAGCAGCATGCGGTTCAAGGG
AAGGTCATCGTGGTCGCGTCGCCGAAAGGCGGAACCGGAAAGACCACCGTTGCGACGAAT
CTTGCAGTAGGACTCGCGGCGGCAGCGCCTCACTCGACGGTGTTGGTGGACCTCGACGTG
CAGTTCGGGGACGTTGCCAGTGCTCTCCAGTTGGTTCCGGAACATTGCCTGACCGACGCC
GTCGCGGCCCGGCCAGCCAGGACATGATCGTCCTCAAGACCGTCCTTACACCCCATTCC
ACAGGACTGCATGCGCTGTGTGGGTCCGACTCGCCCGCGGCGGGCGACAGCATCACCGGC
GAGCAGGTGAGCACTCTGCTGACGCAGTTGGCGGCCGAATTCCGGTACGTGGTCGTCGAC
ACCGCGCCCGGTTTGCTCGAACACACCCTGGCGGCGCTCGACCTCGCTACCGACGTCGTG
TTGGTGTCGGGTATGGACGTGCCCAGCGTCCGCGGGATGCACAAGGAACTGCAGTTGCTG
GCGGAGCTGAATCTGGGTCCGGTCGTGCGGCATGTCGTGCTCAACTTTGCGGATCGACGC
GAGGGGCTGACGGTCCAGGACATCCAGAACACCATCGGGGTCCCCGCCGATATCGTGATC
AAGCGGTCGAAAGCCGTTGCCCTCTCGACGAACCGGGGTGTTCCACTGCTTCAGAACCCG
GGTCGGGATCGCACTGCGAAAGAGTTGTGGCGACTCGTCGGCCGTATCGATCCGGCTCCC
GATACCACCAAGGGTGGACGCGCGCGGCATCGGGCAGCCGAGGCGGTGGGGGCGAAATGA

>RplF_PAM1593 (SEQ ID NO 63):
ATGAGCCGCATCGTCCTGCTGACCGATCGCGACGATTYCGCCCGCCGCGTGTACCACGCC
GCGGACGGCAACCTTCTGGTGTTGCCGGCGCAGCCGGTTCCCCGGGGGCCGGCGCAGTTG
GTCGGGCTCGGCGTGACCGTGCAACCCGACGTTCTCGTTCTCGGTCCGGACGTGCCGGAA
GTGGAGGGCCTCTCCCTCGCCGGCCGGATCGATCATTCGACGCCCGGCACCACGGTGGTT
CTGGCCAGTGATGCGGGCACCGACGTGTGGTTGAGGGCGATGCGCGCCGGCGTGCGGGAC
GTGATGTCGCCGGAGGCGGAGATCGCGGACGTTCGTGCCGTACTCGATCGAGCAGGTCAG
GCCGCGCTGGCGCGACGTCAGGGGCGAGTGCACCGGCGGAGCAGCATGCGGTTCAAGGG
AAGGTCATCGTGGTCGCGTCGCCGAAAGGCGGAACCGGAAAGACCACCGTTGCGACGAAT
CTTGCAGTCGGACTCGCGGCGGCAGCGCCTCACTCCACGGTGTTGGTGGACCTCGACGTG
CAGTTCGGCGACGTTGCCAGTGCTCTCCAGTTGGTTCCGGAACATTGCCTGACCGACGCC
GTCGCGAGCCCGGCCAGCCAGGACATGATCGTCCTCAAGACCGTCCTGACACCCCATTCC
ACAGGACTGCATGCGCTGTGTGGATCGGACTCGCCCGCGGCGGGCGACAGCATCACCGGC
GAGCAGGTGAGCACTCTGCTGACGCAGTTGGCGGCCGAATTCCGGTACGTGGTCGTCGAC
ACCGCGCCCGGTTTGCTCGAACACACCCTGGCGGCGCTCGACCTTGCTACCGACGTCGTG
TTGGTGTCGGGTATGGACGTGCCCAGCGTCCGCGGGATGCACAAGGAACTGCAATTGCTG
ACGGAGCTGAATCTGGGTCCGGTCGTGCGGCATGTCGTGCTCAACTTTGCGGATCGACGC
GAGGGGCTGACGGTCCAGGACATCCAGAACACCATCGGGGTCCCCGCCGATATCGTGATC
AAGCGCTCGAAAGCCGTTGCCCTCTCGACGAACCGGGGGGTTCCACTGCTTCAGAACCCG
GGTCGGGATCGCACTGCGAAAGAGTTGTGGCGACTCGTCGGCCGTATCGATCCGGCTCCC
GATACCGCCAAGGGTGGACGCGCGCGGCATCGGGCAGCCGAGGCGGTGGGTGCGAAATGA

Figure 10 F (ii)

```
>RplF_ATCC33707 (SEQ ID NO 64):
atgagccgcatcgtcctgctgaccgatcgcgacgatttcgcccgccgcgtgtaccacgcc
gcggacggcaaccttctggtgttgccggcgcagccggttccccgggggccggcgcagttg
gtcgggctcggcgtgaccgtgcaacccgacgttctcgttctcggtccggacgtgccggaa
gtggagggcctctccctcgccggccggatcgatcattcgacgcccggcaccacggtggtt
ctggccagtgatgcgggcaccgacgtgtggttgagggcgatgcgcgccggcgtgcgggac
gtgatgtcgccggaggcggagatcgcggacgttcgtgccgtactcgatcgagcaggtcag
gccgcgctggcgcgacgtcaggggcgagtgcaccggcggagcagcatgcggttcaaggg
aaggtcatcgtggtcgcgtcgccgaaaggcggaaccggaaagaccaccgttgcgacgaat
cttgcagtcggactcgcggcggcagcgcctcactccacggtgttggtggacctcgacgtg
cagttcggcgacgttgccagtgctctccagttggttccggaacattgcctgaccgacgcc
gtcgcgagcccggccagccaggacatgatcgtcctcaagaccgtcctgacacccattcc
acaggactgcatgcgctgtgtggatcggactcgcccgcggcgggcgacagcattaccggc
gagcaggtgagcactctgctgacgcagttggcggccgaattccggtacgtggtcgtcgac
accgcgcccggtttgctcgaacacaccctggcggcgctcgaccttgctaccgacgtcgtg
ttggtgtcgggtatggacgtgcccagcgtccgcgggatgcacaaggaactgcaattgctg
acggagctgaatctgggtccggtcgtgcggcatgtcgtgctcaactttgcggatcgacgc
gaggggctgacggtccaggacatccagaacaccatcggggtccccgccgatatcgtgatc
aagcgctcgaaagccgttgccctctcgacgaaccgggggttccactgcttcagaacccg
ggtcgggatcgcactgcgaaagagttgtggcgactcgtcggccgtatcgatccggctccc
gataccgccaagggtggacgcgcgcggcatcgggcagccgaggcggtgggtgcgaaatga
```

Figure 10 G (i)

>RplG_PAM1593 (SEQ ID NO 65):
ATGAGACTGTCCCAACGGCTCGAGGCCGTGCGCGGAGCCGCACCCGTCGAAGCCGCCGCA
CCGATCCCGCCGGGGAAGCAGGGGAAGGCGAAAACGTCCCTCCCTCCGGCCGACGCTCTC
GCCGAACTGAAGGACCGTGCGAGTGCGGCCCTGTACACCCGGATCGGCACCCGCTTCAAC
GACTCCTCGTTGAGCGAGGAGCAACTGCATCTCCTGGTCCGTGAGGAACTGGCCGAAATC
GTGGAGCAAGAGACGACGCCACTCACCTTCGACGAACGGCAGCGCCTGCTCCGTGAGGTT
GCCGACGAGGTACTGGGGCACGGACCGCTCCAGCGGCTACTGGAGGACCCGTCGGTCACC
GAGATCATGGTCAACAGCCACGACATGGTCTACGTCGAGCGGGACGGCACCCTCGTCCGC
AGCTCCGCGCGATTCGCGGACGAGGCGCACCTGCGTCGCGTGATCGAACGCATCGTTTCC
GCCGTCGGTCGACGGATCGACGAATCGTCCCCGCTCGTGGATGCACGCTTGGCGGATGGC
TCCCGTGTCAACGCGGTGATCCCACCGCTCGCATTCAACGGCTCCTCGCTCACCATTCGA
AAGTTCTCGAAAGATCCGTTCCAGGTCGACGATCTCATCGCCTTCGGCACTCTCTCGCAC
GAGATGGCCGAACTGCTCGACGCGTGTGTGCAGGCGCGACTGAACGTCATCGTCTCGGGC
GGCACGGGCACGGGGAAGACGACGCTGCTCAACGTGCTCTCGTCGTTCATTCCGGAAGGG
GAGCGGATCGTCACCATCGAGGACGCCGTGGAACTGCAACTTCAGCAGGACCACGTCGTA
CGGTTGGAGAGCCGACCGCCGAACATCGAGGGCAAGGGTGCCGTCACCATCCGCGACCTG
GTGCGGAACTCGCTGCGTATGCGTCCCGACCGCATCGTGGTGGGGGAGTGTCGCGGAGGC
GAGAGTCTCGACATGCTGCAAGCGATGAACACCGGTCACGACGGGTCGCTGTCGACGGTG
CATGCGAATTCGCCCCGTGACGCCATCGCGCGCTTGGAGACGCTCGTGTTGATGGCGGGC
ATGGACTTGCCGTTGCGGGCGATCCGGGAGCAGATTGCTTCGGCGGTCGACGTGATCGTG
CAGCTCACTCGACTACGTGACGGCACTCGGCGAGTGACCCACGTGACCGAGGTCCAGGGC
ATGGAGGGTGAGATCGTCACACTGCAGGATGCCTTCCTGTTCGACTACAGCGCCGGCGTC
GACGCGCGGGCGATTCCTCGGCAGACCGCAGCCGACGGGAGTGCGGCCGCGGTTCACC
GACAAATTCCGAGATCTCGGTATTGCTTTGTCGCCGAGTGTTTTCGGGGTGGGAGAACCC
TCCCGGGGGCGGGCATGA

Figure 10 G (ii)

>RplG_PAM1571 (SEQ ID NO 66):
ATGAGACTGTCCCAACGGCTCGAGGCCGTGCGCGGAGCCGCACCCGTCGAAGCCGCCGCA
CCGATCCCGCCGGGGAAGCAGGGGAAGGCGAAGACGTCCCTCCCTCCGGCCGACGCTCTC
GCCGAACTGAAGGACCGTGCGAGTGCGGCCCTGTACACCCGGATCGGCACCCGCTTCAAC
GACTCCTCGTTGAGCGAGGAGCAACTGCATCTCCTGGTCCGTGAGGAACTGGCCGAGATC
GTGGAGCAGGAGACGACGCCACTCACCTTCGACGAGCGGCAGCGCCTGCTCCGTGAGGTC
GCCGACGAGGTACTGGGGCACGGACCGCTTCAGCGGCTACTGGAGGACCCGTCGGTCACC
GAGATCATGGTCAACAGCCACGACATGGTCTACGTCGAGCGGGACGGCACCCTCGTTCGC
AGCTCCGCGCGATTCGCGGACGAGGCGCACCTGCGCCGCGTGATCGAACGCATCGTTTCC
GCCGTCGGTCGACGGATCGACGAATCGTCCCCGCTCGTGGATGCACGCTTGGCGGACGGC
TCCCGTGTCAACGCGGTGATCCCACCGCTCGCATTCAACGGCTCCTCGCTCACCATTCGA
AAGTTCTCGAAAGATCCGTTCCAGGTCGACGATCTCATCGCCTTCGGCACTCTCTCGCAC
GAGATGGCCGAACTGCTCGACGCGTGTGTGCAGGCGCGACTGAACGTCATCGTCTCGGGC
GGCACGGGCACGGGGAAGACGACGCTGCTCAACGTGCTCTCGTCGTTCATTCCGGAAGGG
GAGCGGATCGTCACCATCGAGGACGCCGTGGAACTGCAACTTCAGCAGGACCACGTCGTA
CGGTTGGAGAGCCGACCGCCGAACATCGAGGGCAAGGGCGCCGTCACCATCCGTGACCTG
GTGCGGAACTCGCTGCGTATGCGTCCTGACCGCATCGTGGTGGGGAGTGTCGCGGAGGC
GAGAGTCTCGACATGCTGCAAGCGATGAACACCGGTCACGACGGGTCGCTGTCGACGGTG
CATGCGAATTCGCCCCGTGACGCCATCGCGCGCTTGGAGACGCTCGTGTTGATGGCGGGC
ATGGACCTGCCGTTGCGGGCGATCCGGGAGCAGATTGCTTCGGCGGTCGACGTGATCGTG
CAGCTCACTCGACTACGTGACGGCACTCGGCGAGTGACCCACGTGACCGAGGTCCAGGGC
ATGGAGGGTGAGATCGTCACCCTGCAGGATGCCTTCCTGTTCGACTACAGCGCCGGCGTC
GACGCGCGCGGGCGATTCCTCGGCAGACCGCAGCCGACCGGAGTGCGGCCGCGGTTCACC
GACAAATCCGAGATCTCGGTATTGCTTTGTCGCCGAGTGTTTCGGGGTGGGAGAACCC
TCCCGGGGGCGGGCATGA

Figure 10 G (iii)

>RplG_ATCC33707 (SEQ ID NO 67):
atgagactgtcccaacggctcgaggccgtgcgcggagccgcacccgtcgaagcggccgca
ccgatcccgccggggaagcaggggaaggcgaagacgtccctccctccggccgacgctctc
gccgaactgaaggaccgtgcgagtgcggccctgtacacccggatcggcacccgcttcaac
gactcctcgttgagcgaggagcaactgcatctcctggtccgtgaggaactggccgaaatc
gtggagcaagagacgacgccactcaccttcgacaacggcagcgcctgctccgtgaggtc
gccgacgaggtactggggcacggaccgctccagcggctactggaggacccgtcggtcacc
gagatcatggtcaacagccacgacatggtctacgtcgagcgggacggcaccctcgtccgc
agctccgcgcgattcgcggacgaggcgcacctgcgtcgcgtgatcgaacgcatcgtttcc
gccgtcggtcgacggatcgacgaatcgtccccgctcgtggatgcacgcttggcggatggc
tcccgtgtcaacgcggtgatcccaccgctcgcattcaacggctcctcgctcaccattcga
aagttctcgaaagatccgttccaggtcgacgatctcatcgccttcggcactctctcgcac
gagatggccgaactgctcgacgcgtgtgtgcaggcgcgactgaacgtcatcgtctcgggc
ggcacgggcacggggaagacgacgctgctcaacgtgctctcgtcgttcattccggaaggg
gagcggatcgtcaccatcgaggacgccgtggaactgcaacttcagcaggaccacgtcgta
cggttggagagccgaccgccgaacatcgagggcaagggcgccgtcaccatccgcgacctg
gtgcggaactcgctgcgtatgcgtcccgaccgcatcgtggtggggagtgtcgcggaggc
gagagtctcgacatgctgcaagcgatgaacaccggtcacgacgggtcgctgtcgacggtg
catgcgaattcgcccgtgacgccatcgcgcgcttggagacgctcgtgttgatggcgggc
atggacctgccgttgcgggcgatccgggagcagattgcttcggcggtcgacgtgatcgtg
cagctcactcgactacgtgacggcactcggcgagtgacccacgtgaccgaggtccagggc
atggagggtgagatcgtcaccctgcaggatgccttcctgttcgactacagcgccggcgtc
gacgcgcgcgggcgattcctcggcagaccgcagccgaccggagtgcggccgcggttcacc
gacaaattccgagatctcggtattgctttgtcgccgagtgttttcggggtgggagaaccc
tcccggggcgggcatga

Figure 10 H (i)

```
>RplH_PAM1593 (SEQ ID NO 68):
ATGAGTCGGTGCGTGGTGGCCGTCGTGCTCGCCCTCGGTGCGGGTGTTCTGGGAATTCCT
GCCGTAGCCGCGGCGCCNNNGGAGGCTGTCCAGGTCTCGGCGGTCGACACGACCCGGTTT
CCCGACATCGAGGTGTCCATCCTCGCGCCGCCCGGTATCGAAGGGCAGGCGATCGATCCG
GGAACGTTCGCGCTCACCGAGGGCGGCGTGCCGCGAGAGATCGAGGTCAGGCAGCAGCCG
GGTTCCGAGCAGGACATCGTGCTCGCAATCGACGTGTCCGGGGGCATGTCGGGTCCGGCG
CTGGACGACGTGAAGCGCGCCGCATCGGATTTCGTGCGGCAGGCGCCGACCGGCGCCCAC
ATCGGAATCGTCGCGATCTCGTCGACGCCACAGGTGCTCTCGGAACTGACGACGGACTCC
GAGGACCTGCTCCGCAGGATCGACGGACTGAAGGCGGGCGGCAACAGCGCGATCGCAGAT
TCGGTGGTGACCGCCGCCGAGATGCTCGAGCGCGGCGAAGCGGCCAACAACATCCTGCTT
CTGTTGACGGACGGCGCCGACACGTCGAGTGCACACTCGATGTCGGAACTCCCGTCCGTC
CTGAGTCGGTCGCGCGCGTCGCTGTACGCCGTGCAGATGTCGACACCCGAGACGAACTCT
GCTCTCCTGCAGCAGGTTGCGCGGGAGTCGCGCGGTCAGTACGCGTCTGCGGGTGATACG
GCGGCGCTGGGTGCGATCTACCAGTCGGCCGCTCGCGCGCTCGGAAACCTGTACGTCGTC
CGATACCGATCGGAAGCGAACGGCGATACCCAGGTGGTGGCGAGCGTGCGCAGCGGCGCA
GCCGGCCGAGTGAGCGATCCGTTCCCGGTGACATTGCCCGGTGTGGTGCCGACGCCGAGC
GTCGTCGCCGGGACCGTCGACGGTTTCTTCACGTCTTCGACGGGCTGGTGATCGGGCTC
CTAGCGTGCTACTCGGCGCTTGCGGGAGGCGTGCTGGCGGTCGCCGGTAGAGCGCCCGCG
AGGATTTCGGCAGCACGTCGTGGGCGGCAGGACGGACGGGACTCGATGCTGTCCCGATTC
GCGGAACGGCTGGTGCAGTGGATCGATCAGAACCTGAGGAGACGCGGACGCATCGCTGCC
CGCACCCAGGCGCTACAGGAGGCGGGGCTGAAGCTTCGTCCAGGTGACTTCATCGCCCTG
GTCGGTGCTGCGGCGATCACCGCTGCGGCGATCGGTCTCCTGGCTTCGGGCATCGTGGCG
GCGCTCTTGCTCGCGGCGATCACAGTGGGATTGTCGAGAATCTATCTCCGTGTGATGGCC
GGTAGGCGTCGGGCCGCGTTCGCTGATCAGCTCGACGATTCCCTGCAGCTGCTGGCCAGC
AATCTCCGAGCCGGGCACAGCATGCTCCGAGCGCTCGATTCCCTTTCCCGAGAGGCGGAG
GTGCCGACTTCGGAGGAGTTCGCTCGGATCGTCAACGAGACTCGGGTGGACGTGATCTC
AACGAGGCTCTCGACGACGTGGCCCGGCGGATGCGAAGTGACGATTTCAACTGGATAGCT
CAGGCGATCGCCATCAACCGTGAGGTCGGAGGCGACCTCGCGGAAGTCCTCGACCAGGTG
GGCAACACCATTCGAGAGCGAAATCAGATTCGACGGCAGGTGAAAGCCCTTGCTGCCGAG
GGGAAACTGTCCGCCTACGTGCTGATGGCGCTGCCCTTCGGTCTCACCGCATTTCTGCTC
GTCTCGAATCCGGACTACCTGTCGAAGTTGACGGGTAGCGCCATCGGCTACGTGATGATC
GCGGTGGGGCTCGTCATGCTGACCGTCGGTGGGCTGTGGATGAACAAGGTTGTCTCGGTC
AAGTTCTAG
```

Figure 10 H (ii)

\>RplH_PAM1571_N (SEQ ID NO 69):
ATGAGTCGGTGCGTGGTGGCCGTCGTGCTCGCCCTCGGTGCGGGTGTTCTGGGAATTCCT
GCCGTAGCCGCGGCGGCCGAGACGGAGGCTGTCCAGGTCTCGGCGGTCGACACGACCCGG
TTTCCCGACATCGAGGTGTCCATCCTCGCGCCGCCCGGTATCGAAGGGCAGGCGATCGAT
CCGGGAACGTTCGCGCTCACCGAGGGAGGCGTGCCGCGAGAGATCGAGGTCAGGCAGCAG
CCGGGTTCCGAGCAGGACATCGTGCTCGCAATCGACGTGTCCGGGGCATGTCGGGTCCG
GCGCTGGACGACGTGAAGCGCGCCGCATCGGATTTCGTACGGCAGGCGCCGACCGGCGCC
CACATCGGAATCGTCGCGATCTCGTCGACGCCACAGGTGCTCTCGGAACTGACGACGGAC
TCCGAGGACCTGCTCCGCAGGATCGACGGACTGAAGGCGGGCGGCAACAGCGCGATCGCA
GATTCGGTGGTGACCGCCGCCGAGATGCTCGAGCGCGGCGAAGCGGCCAACAACATCCTG
CTTCTGTTGACGGACGGCGCCGACACGTCGAGTGCACACTCGATGTCGGAACTCCCGTCC
GTCCTGAGTCGGTCGCGCGCGTCGCTGTACGCCGTGCAGATGTCGACACCCGAGACGAAC
TCTGCTCTCCTGCAGCAGGTTGCGCGGGAGTCGCGCGGTCAGTACGCGTCTGCGGGTGAT
ACGGCGGCGCTGGGTGCGATCTACCAGTCGGCCGCTCGCGCGCTCGGAAACCTGTACGTC
GTCCGATACCGATCGGAAGCGAACGGCGATACCCAGGTGGTGGCGAGCGTGCGCAGCGGC
GCAGCCGGCCGAGTGAGCGATCCGTTCCCGGTGACATTGCCCGGTGTGGTGCCGACGCCG
AGCGTCGTCGCCGGGACCGTCGACGGTTTCTTCACGTCTTCGACGGGGCTGGTGATCGGG
CTCCTAGCGTGCTACTCGGCGCTTGCGGGANNNNNNctggcggtcgccggtagagggccc
gcgaggatttcggcagcacgtcgtgggcggcaggacggacgggactcgatgctgtcccga
ttcgcggaacggctggtgcagtggatcgatcagaacctgaggagacgcggacgcatcgct
gcccgcacccaggcgctacaggaggcggggctgaagcttcgtccaggtgacttcatcgcc
ctggtcggtgctgcggcgatcaccgctgcggcgatcggtctcctggcttcgggcatcgtg
gcggcgctcttgctcgcggcgatcacagtgggattgtcgagaatctatctccgggtgatg
gccggtaggcgtcgggccgcgttcgctgatcagctcgacgattccctgcagctgctggcc
agcaatctccgagccgggcacagcatgctccgagcgctcgattccctttcccggaggcg
gaggtgccgacttcggaggagttcgctcggatcgtcaacgagactcgggtgggacgtgat
ctcaacgagtctctcgacgacgtggcccggcggatgcgaagtgacgatttcaactggata
gctcaggcgatcgccatcaaccgtgaggtcggaggcgacctcgcggaagtcctcgaccag
gtgggcaacaccattcgagagcgaaatcagattcgacggcaggtgaaagcccttgctgcc
gagggaaactgtccgcctacgtgctgatggcgctgcccttcggtctcaccgcatttctg
ctcgtctcgaatccggactacctgtcgaagttgacgggtagcgccatcggctacgtgatg
atcgcggtggggctcgtcatgctgaccgtcggtgggctgtggatgaacaaggttgtctcg
gtcaagttctag

Figure 10 H (iii)

>RplH_ATCC33707 (SEQ ID NO 70):
atgagtcggtgcgtggtggccgtcgtgctcgccctcggtgcgggtgttctgggaattcct
gccgtagccgcggcggccgagacggaggctgtccaggtctcggcggtcgacacgacccgg
tttcccgacatcgaggtgtccatcctcgcgccgccggtatcgaagggcaggcgatcgat
ccgggaacgttcgcgctcaccgagggaggcgtgccgcgagagatcgaggtcaggcagcag
ccgggttccgagcaggacatcgtgctcgcaatcgacgtgtccggggcatgtcgggtccg
gcgctggacgacgtgaagcgcgccgcatcggatttcgtgcggcaggcgccgaccggcgcc
cacatcggaatcgtcgcgatctcgtcgacgccacaggtgctctcggaactgacgacggac
tccgaggacctgctccgcaggatcgacggactgaaggcgggcggcaacagcgcgatcgca
gattcggtggtgaccgccgcgagatgctcgagcgcggcgaagcggccaacaacatcctg
cttctgttgacggacggcgccgacacgtcgagtgcacactcgatgtcggaactcccgtcc
gtcctgagtcggtcgcgcgcgtcgctgtacgccgtgcagatgtcgacgcccgagacgaac
tctgctctcctgcagcaggttgcgcgggagtcgcgcggtcagtacgcgtctgcgggtgat
acggcggcgctgggtgcgatctaccagtcggccgctcgcgcgctcggaaacctgtacgtc
gtccgataccgatcggaagcgaacggcgatacccaggtggtggcgagcgtgcgcagcggc
gcagccggccgagtgagcgatccgttcccggtgacattgcccggtgtggtgccgacgccg
agcgtcgtcgccgggaccgtcgacggtttcttcacgtcttcgacggggctggtgatcggg
ctcctagcgtgctactcggcgcttgcgggaggcgtgctggcggtcgccggtagagcgccc
gcgaggatttcggcagcacgtcgtgggcggcaggacggacgggactcgatgctgtccga
ttcgcggaacggctggtgcagtggatcgatcagaacctgaggagacgcggacgcatcgct
gcccgaacccaggcgctacaggaggcggggctgaagcttcgtccaggtgacttcatcgcc
ctggtcggtgctgcggcgatcaccgctgcggcgatcggtctcctggcttcgggcatcgtg
gcggcgctcttgctcgcggcgatcacagtgggattgtcgagaatctatctccgtgtgatg
gccggtaggcgtcgggccgcgttcgctgatcagctcgacgattccctgcagctgctggcc
agcaatctccgagccgggcacagcatgctccgagcgctcgattcccttcccgagaggcg
gaggtgccgacttcggaggagttcgctcggatcgtcaacgagactcgggtgggacgtgat
ctcaacgagtctctcgacgacgtggcccggcggatgcgaagtgacgatttcaactggata
gctcaggcgatcgccatcaaccgtgaggtcggaggcgacctcgcggaagtcctcgaccag
gtcggcaacaccattcgagagcgaaatcgattcgacggcaggtgaaagcccttgctgcc
gaggggaaactgtccgcctacgtgctgatggcgctgcccttcggtctcaccgcatttctg
ctcgtctcgaatccggactacctgtcgaagttgacgggtagcgccatcggctacgtgatg
atcgcggtggggctcgtcatgctgaccgtcggtgggctgtggatgaacaaggttgtctcg
gtcaagttctag

Figure 10 I (i)

>RplI_PAM1571 (SEQ ID NO 71):
GTGATTCCACCGCTGGTGCTCATGGCGGCGCTGTCCGTCGGCGGGGCGTTGGGTGTTCTG
GTGTGGTTGACGGCCGGCGCCCGAGATCCAGAACGCGGACCCGCCCTTCAGAACCTGCAG
TCGCAGCTGGCGTTGCCGATTCCGGAGTCGGGAGGCGCGCCACCGCTTTCGCTCGGCCGA
TTCGTGAAGCTGCTGTCGCCGCCCGGGACGATGGCCCGCTTGGAACGACTGCACATCCTT
GCCGGTCGTCCAGCGGCGTGGGTTCCGGAACGGGCCGCGATGGCGAAGATCGTTCTCGCC
GCGGCCGCCGCCCTGCTCGGCCTTCTCGCGGTGGGTGCGTCGCCTGGCGTCGGCCGGGTG
CTGTTCGCTGCGGCCGCCGTCGCGCTGGCGTATTTCGTCCCGGAACTTCTCCTGCAGAGC
AGGGGGCAGGAGCGCCAAGCCGCGATCGAACTGGCGCTTGCCGACACCCTCGACCAGATG
ACGATCGCAGTCGAGGCGGGCCTGGGGTTCGAAGCCGCCATGCAGCGGGCCGCGAAGAAC
GGAAAGGGGCCGCTGGCCGAGGAATTCATCCGGACATTGCAGGACATACAGATGGGGCAG
TCGAGGCGAATCGCGTACCTGGATCTTGCCGCCAGAACGAAAGCACCCAACTTGCGGAGG
TTCCTTCGGGCCGTCATCCAAGCCGACGAGTACGGCGTGGCCATCGCCGAGGTCCTGCGG
ACCCAGGCCTCGGAGATGCGTCTGAAACGCCGTCAGAGTGCTGAGGAGAAGGCGATGAAG
GTTCCGGTGAAGGTGCTGTTTCCGTTGATGACCTGCATCCTGCCGACCATCTTCATCGTG
ATCCTGGGTCCGGCGGTGATCAACATGATGGAGGTCTTGGGCGGTATGTAA

>RplI_PAM1953 (SEQ ID NO 72):
GTGATTCCACCGCTGGTGCTCATGGCGGCGCTGTCCGTCGGCGGGGCGTTGGGTGTTCTG
GTGTGGTTGACGGCCGGCGCCCGAGATCCGGAACGCGGACCCGCCCTTCAGAACCTCCAG
TCGCAGCTGGCGCTGCCGATTCCGGAGTCGGGAGGCGCGCCACCGATTTCGCTCGGCCGA
TTCGTGAAGCTGCTGTCGCCACCCGGGACGATGGCCCGGTTGGAACGACTGCACATCCTT
GCCGGTCGTCCAGCGGCGTGGGTTCCGGAACGGGCCGCGATGGCGAAGATCGTTCTCGCC
GCGGCCGCCGCCCTGCTCGGCCTTCTCGCGGCGGGTGCGTCGCCTGGCGTCGGCCGGGTG
CTGTTCGCTGCGGCCGCCGTCGCGCTGGCGTATTTCGTCCCGGAACTTCTCCTGCAGAGC
AGGGTGCAGGAGCGCCAAGCCGCGATCGAACTGGCGCTTGCCGACACCCTCGACCAGATG
ACGATCGCAGTCGAGGCGGGCCTGGGGTTCGAAGCCGCAATGCAGCGGGCCGCGAAGAAC
GGAAAGGGGCCGCTGGCCGAGGAATTCATCCGGACATTGCAGGACATACAGATGGGGCAG
TCGAGGCGAATCGCGTACCTGGATCTTGCCGCCAGAACGAAAGCACCGAACTTGCGGAGG
TTCCTTCGGGCCGTCATCCAAGCCGACGAGTACGGCGTGGCCATCGCCGAGGTTTTGCGG
ACCCAGGCCTCGGAGATGCGTCTGAAACGCCGTCAGAGTGCTGAGGAGAAGGCGATGAAG
GTTCCGGTGAAGGTGCTGTTTCCATTGATGACCTGCATCCTGCCGACCATCTTCATCGTG
ATCCTGGGTCCGGCGGTGATCAACATGATGGAGGTCCTGGGCGGTATGTAA

Figure 10 I (ii)

>RplI_ATCC33707 (SEQ ID NO 73):
gtgattccaccgctggtgctcgtggcggcgctgtccgtcggcggggcgttgggtgttctg
gtgtggttgacggccggcgcccgagatccggaacgcggacccgcccttcagaacctccag
tcgcagctggcgttgccgattccggtgtcgggaggcgcgccaccgctttcgctcggccga
ttcgtgaagctgctgtcgccgcccgggacgatggcccgcttggaacgactgcacatcctt
gccggtcgtccagcggcgtggggttccggaacgggccgcgatggcgaagatcgttctcgcc
gcggccgccgccctgctcggccttctcgcggtgggtgcgtcgcctggcgtcggccgggtg
ctgttcgctgcggccgccgtcgcgctggcgtatttcgtcccggaacttctcctgcagagc
aggggcaggagcgccaagccgcgatcgaactggcgcttgccgacaccctcgaccagatg
acgatcgcagtcgaggcgggcctggggttcgaagccgccatgcagcgggccgcgaagaac
ggaaaggggccgctggccgaggaattcatccggacattgcaggacatacagatggggcag
tcgaggcgaatcgcgtacctggatcttgccgccagaacgaaagcacccaacttgcggagg
ttccttcgggccgtcatccaagccgacgagtacggcgtggccatcgccgaggtcctgcgg
acccaggcctcggagatgcgtctgaaacgccgtcagagtgctgaggagaaggcgatgaag
gttccggtgaaggtgctgtttccgttgatgacctgcatcctgccgaccatcttcatcgtg
atcctgggtccggcggtgatcaacatgatggaggtcttgggcggtatgtaa

IMMUNE SYSTEM MODULATING COMPOSITION

FIELD OF THE INVENTION

The present invention relates to polypeptides encoded by *Rhodococcus (Corynebacterium) equi (R. equi)*, compositions including such polypeptides (Rpl) and antibodies to such polypeptides, which can be useful in the treatment of animals, specifically horses and foals, to minimise infection of animals, by *R. equi*. The invention further relates to methods of detection of *R. equi* using polypeptides (Rpl), antibodies with binding specificity to said polypeptides or nucleic acids or the like with binding specificity to nucleic acids encoding such polypeptides using, for example, PCR.

BACKGROUND TO THE INVENTION

*Rhodococcus equi* is a Gram-positive, facultative intracellular coccobacillus classified in the order of Acitnomycetales. It is primarily a soil organism. It has been recognised as a positive agent of a debilitating and potentially fatal bronchopneumonia affecting foals worldwide. *R. equi* is considered to be one of the most significant pathogens in the equine breeding industry.

The successful early diagnosis and treatment of Rhodococcus equi in foals and management of the foals environment to reduce the risk of contracting the disease are, arguably, among the most challenging experiences currently facing equine stud farms. Presently the treatment of *R. equi* disease is by the prolonged administration of a combination of antimicrobials, macrolides, i.e. erythromycin, azithromycin or clarithromycin, and rifampicin. However, as this therapy risks antibiotic resistance and adverse drug reactions in the foal and the dam, improved means of therapy and prophylactic treatment are required.

*R. equi* can also affect non-equine species. In pigs *R. equi* is associated with granulomatous lymphadenitis of cervical lymphatic tissue and in man *R. equi* can cause cavitary pneumonia, predominantly in immunocompromised individuals especially those with acquired immune deficiency syndrome (AIDS). As a consequence of the AIDS pandemic, *R. equi* pneumonia has become a disease of increasing significance in human medicine. *R. equi* infections have also been described in cattle, sheep, goats, lama, cats and dogs, but disease in these species is rare with lesions confined to lymph node abscessation or wound infection.

Infection by *R. equi* relies on the ability of *R. equi* to colonise the airways and replicate inside macrophages which is dependent on its capacity to interfere with endosomal maturation following phagocytosis and to prevent acidification of the vacuole in which it resides. Eventually, intracellular proliferation of the pathogen leads to the necrotic death of the marcophages accompanied by massive damage to lung tissue characterised by cavitation and granuloma formation.

Studies of the virulent strains of *R. equi* have determined that such strains possess an extra chromosomal DNA element known as a plasmid, which is associated with virulence. Plasmids isolated from regular strains infecting foals have been proposed to include a region that represents a pathogenicity island, which is a DNA fragment containing genes required for virulence. The pathogenicity island identified contains a family of nine virulence associated protein (Vap) chains (VapA-VapC-Vap-I, pseudo-VapE). Killed/inactivated *R. equi* organisms do not illicit protective immunity, and there is no consistent evidence that protein or DNA vaccines, based on the highly immunogenic VapA surface antigen, are efficacious in producing protection against a Rhodococcal pneumonia in foals. In view of the lack of an efficacious vaccine, *R. equi* infection is a major cause of mortality in young foals and the heavy economic losses incurred due to *R. equi* has a major economic impact in countries where thoroughbred racing and breeding is important (USA, Australia, Ireland, Argentina, UK, France, Spain, Germany, Austria, Japan etc.). There is a need for treatment regimes and a vaccine to be developed which can be used to control *R. equi* on farms, in particular stud farms.

SUMMARY OF THE INVENTION

The inventors have determined a novel diagnostic marker and vaccine candidate for *Rhodococcus equi* in horses and other susceptible species and treatment means. Specifically, the inventors have identified a rpl pathogenicity island that differs from the yap pathogenicity island and the inventors have determined the rpl pathogenicity island, in particular RplB, encodes a major adhesion factor of *R. equi* which enables host colonisation. The proteins (Rpl) encoded by the rpl pathogenicity island are considered to be major immunodominant antigens. The inventors have further determined that the rpl pathogenicity island is absent from non-pathogenic *Rhodococcus* species. These findings allow the use of probes to proteins or nucleic acid of the rpl pathogenicity island and antibodies with binding specificity to the proteins encoded by the rpl pathogenicity island in methods of detection of *R. equi*. Further, it enables the use of nucleic acids encoding proteins or proteins of the rpl pathogenicity island as immune system modulators, in particular to provoke a protective immune response to subsequent antigen challenge in an animal.

Accordingly, a first aspect of the invention provides at least one immunogenic *R. equi* polypeptide having an amino acid sequence, encoded by a polynucleotide sequence comprising a polynucleotide sequence of a gene selected from a gene as listed at table one, or a fragment, derivative or variant of such a polypeptide.

TABLE ONE

| rpl locus | Identifier | Proposed function of encoded protein | Position in *R. equi* 103S | SEQ ID NO |
|---|---|---|---|---|
| rplA | REQ_18350 | Prepilin peptidase | Position 1938280-1939068 (complement) in 103S genome | 1 |
| rplB | REQ_18360 | Pilin subunit | Position 1939395-1939601 in 103S genome | 2 |
| rplC | REQ_18370 | Minor pilin protein | Position 1939683.-1940084 in 103S genome | 3 |
| rplD | REQ_18380 | Putative lipoprotein | Position 1940093-1941037 1940084 in 103S genome | 4 |
| rplE | REQ_18390 | Pilus assembly protein | Position 1941047-1941784 in 103S genome | 5 |
| rplF | REQ_18400 | Pilus assembly ATPase | Position 1941781-1942980 in 103S genome | 6 |
| rplG | REQ_18410 | Secretion apparatus ATPsae | Position 1942977-1944374 in 103S genome | 7 |

TABLE ONE-continued

| rpl locus | Identifier | Proposed function of encoded protein | Position in R. equi 103S | SEQ ID NO |
|---|---|---|---|---|
| rplH | REQ_18420 | Secretion apparatus integral membrane protein | Position 1944371-1946239 in 103S genome | 8 |
| rplI | REQ_18430 | Secretion apparatus integral membrane protein | Position 1946262-1947152 in 103S genome | 9 |

In embodiments of the invention, the polypeptide or derivative or variant or fragment thereof can be encoded by a polynucleotide sequence comprising a polynucleotide sequence of a gene as listed in Table 2

TABLE TWO

| rpl locus | Identifier | Proposed function of encoded protein | Position in R. equi 103S | SEQ ID NO |
|---|---|---|---|---|
| rplA | REQ_18350 | Prepilin peptidase | Position 1938280-1939068 (complement) in 103S genome | 1 |
| rplB | REQ_18360 | Pilin subunit | Position 1939395-1939601 in 103S genome | 2 |
| rplC | REQ_18370 | Minor pilin protein | Position 1939683.-1940084 in 103S genome | 3 |
| rplD | REQ_18380 | Putative lipoprotein | Position 1940093-1941037 1940084 in 103S genome | 4 |
| rplE | REQ_18390 | Pilus assembly protein | Position 1941047-1941784 in 103S genome | 5 |
| rplH | REQ_18420 | Secretion apparatus integral membrane protein | Position 1944371-1946239 in 103S genome | 8 |
| rplI | REQ_18430 | Secretion apparatus integral membrane protein | Position 1946262-1947152 in 103S genome | 9 |

In particular embodiments the polypeptide or a derivative or variant or fragment thereof can be encoded by a polynucleotide sequence comprising a polynucleotide sequence of a gene selected from rplB (SEQ ID NO 2), rplC (SEQ ID NO 3), or rplD (SEQ ID NO 4). In an alternative embodiment, the polypeptide or a derivative can be encoded by a polynucleotide sequence comprising a polynucleotide sequence of a gene selected from rplB (SEQ ID NO 2), rplA (SEQ ID NO 1) or rplE (SEQ ID NO 5).

In embodiments of the invention, the polypeptide or a derivative or fragment thereof is encoded by a polynucleotide sequence comprising a polynucleotide sequence of a gene selected from the list of genes of Table 1, more preferably selected from the list of genes of Table 2.

In embodiments of the invention, the polypeptide or a derivative or fragment or variant thereof is encoded by a polynucleotide sequence consisting essentially of or consisting of a polynucleotide sequence of a gene selected from the list of genes of Table 1, more preferably selected from the list of genes of Table 2.

In embodiments, the polypeptide is encoded by a polynucleotide sequence comprising the polynucleotide sequence of a gene encoding Rpl pilin ATGAACCTCTTCTTCGCGAACCTGTACCTCATGGGCTTAGACGTCAA GGACCGTCTGACCCGTGACGACCGCGGCGCCACTGCGGTCGAGTAC GGACTGATGGTCGCCGGCATCGCGATGGTGATCATTGTTGCGGTTTT CGCCTTCGGCGATAAGATTACCGACCTCTTCGATGGCTTCAACTTCG ACGATCCCGGCGGCGAGTAG (SEQ ID NO 2).

In embodiments, the polypeptide is encoded by a polynucleotide sequence consisting essentially of or consisting of the polynucleotide sequence of a gene encoding Rpl pilin ATGAACCTCTTCTTCGCGAACCTGTACCTCATGGGCTTAGACGTCAA GGACCGTCTGACCCGTGACGACCGCGGCGCCACTGCGGTCGAGTAC GGACTGATGGTCGCCGGCATCGCGATGGTGATCATTGTTGCGGTTTT CGCCTTCGGCGATAAGATTACCGACCTCTTCGATGGCTTCAACTTCG ACGATCCCGGCGGCGAGTAG (SEQ ID NO 2).

In embodiments, the polypeptide is encoded by a polynucleotide sequence comprising a fragment of the polynucleotide sequence of a gene encoding Rpl pilin ATGAACCTCTTCTTCGCGAACCTGTACCTCATGGGCTTAGACGTCAA GGACCGTCTGACCCGTGACGACCGCGGCGCCACTGCGGTCGAGTAC GGACTGATGGTCGCCGGCATCGCGATGGTGATCATTGTTGCGGTTTT CGCCTTCGGCGATAAGATTACCGACCTCTTCGATGGCTTCAACTTCG ACGATCCCGGCGGCGAGTAG (SEQ ID NO 2) wherein the polypeptide encoded by the fragment is a biologically active immunogenic fragment of a polypeptide encoded by the polynucleotide sequence comprising the polynucleotide sequence of the gene encoding Rpl pilin ATGAACCTCTTCTTCGCGAACCTGTACCTCATGGGCTTAGACGTCAA GGACCGTCTGACCCGTGACGACCGCGGCGCCACTGCGGTCGAGTAC GGACTGATGGTCGCCGGCATCGCGATGGTGATCATTGTTGCGGTTTT CGCCTTCGGCGATAAGATTACCGACCTCTTCGATGGCTTCAACTTCG ACGATCCCGGCGGCGAGTAG (SEQ ID NO 2).

In embodiments, a derivative or fragment or variant can be an immunogenic derivative or fragment or variant that can provide an immune response in which antibodies with binding specificity to at least one of SEQ ID NO 1, 2, 3, 4, 5, 6, 7, 8, and 9 are generated for example antibodies cross-reactive to the biologically active immunogenic fragment and at least one of SEQ ID NO 1, 2, 3, 4, 5, 6, 7, 8 and 9.

In particular embodiments such fragments, derivatives or variants can functionally provide a pilus in R. equi. Such derivatives, fragments or variants can be biologically active derivatives, fragments or variants.

In embodiments the Rpl pilin polypeptide (RplB) can comprise an amino acid sequence MNLFFANLYLMGLDVKDRLTRDDRGATAVEYGLMVAGIAMVIIVAVFAFG DKITDLFDGFNFDDPGGE (SEQ ID NO 10).

In embodiments, a polypeptide of the invention can consist of an amino acid sequence MNLFFANLYLMGLDVKDRLTRDDRGATAVEYGLMVAGIAMVIIVAVFAFG DKITDLFDGFNFDDPGGE (SEQ ID NO 10).

In embodiments a polypeptide of the invention can comprise DKITDLFDGFNFDDPGGE (SEQ ID NO 11) or can be a variant thereof wherein such variant has at least 1, at least 2, at least 3, at least 4, at least 5, at least 6, at least 7, at least 8, at least 9, at least 10 amino acids different to that of SEQ ID NO 11. Substituted amino acids may suitably be conservative or non conservative amino acids. Alternatively, the variant may include insertions or deletions. Suitably, in embodiments a variant can demonstrate analogous biological function as a RplB pilin subunit or SEQ ID NO 11. In embodiments, a conserved variant may be provided by amino acid sequences comprising DKITDLFDGFNFDDPGGE (SEQ ID NO 11) wherein amino acids as shown are replaced by amino acids which are structurally conservative. For example, an aliphatic amino acid (alanine, serine, valine, leucine, isoleucine or the like) can be substituted with another suitable aliphatic amino acid, a hydrophobic amino acid (tyrosine, phenylalanine, tryptophan) can be substituted by another hydrophobic amino acid or a charged amino acid can be substituted by another charged amino acid. In such conserved variants, additional amino acids may be substituted.

In embodiments a polypeptide of the invention can comprise the amino acid sequence DKITDLFDGFNFDDPGGE (SEQ ID NO 11). In embodiments a polypeptide of the invention consists of, or consists essentially of the amino acid sequence DKITDLFDGFNFDDPGGE (SEQ ID NO 11).

A polypeptide of the invention may be provided using recombinant means or may be a synthetic polypeptide or may be extracted from R. equi bacteria, R. equi culture supernatant or from biological material infected with R. equi. In embodiments an isolated immunogenic polypeptide of the invention is expressed at the bacterial cell surface of a R. equi, or is secreted from R. equi.

In embodiments, a polypeptide of the invention, or a fragment, derivative or variant thereof comprises an amino acid sequence of at least one polypeptide selected from the group consisting of the list provided by Table 3 or as set out in the sequences of FIG. 9.

TABLE THREE

| Rpl protein | Identifier | Proposed function | SEQ ID NO |
|---|---|---|---|
| RplA | REQ_18350 product | Prepilin peptidase | 12 |
| RplB | REQ_18360 product | Pilin subunit | 13 |
| RplC | REQ_18370 product | Minor pilin protein | 14 |
| RplD | REQ_18380 product | Putative lipoprotein | 15 |
| RplE | REQ_18390 product | Pilus assembly protein | 16 |
| RplF | REQ_18400 product | Pilus assembly ATPase | 17 |
| RplG | REQ_18410 product | Secretion apparatus ATPsae | 18 |
| RplH | REQ_18420 product | Secretion apparatus integral membrane protein | 19 |
| RplI | REQ_18430 product | Secretion apparatus integral membrane protein | 20 |

All of the polypeptides shown in Table 3 are encoded in the rpl locus and are part of the R. equi Rpl pilus biogenesis machinery.

In embodiments a polypeptide of the invention can be encoded by an R. equi. strain isolated from horses. In embodiments the polypeptide can be isolated from horses and can be from a virulent strain of R. equi. In embodiments, polypeptides of the invention can be made synthetically or recombinantly using techniques which are widely available in the art.

The polypeptide of the invention may be optionally linked to an immunogenic carrier. Said immunogenic carrier may be a heterologous polypeptide, lipid, liposome, or another acceptable carrier molecule. Suitably, a polypeptide of the invention may be linked to the immunogenic carrier by chemical coupling or a polypeptide of the invention may be expressed as a fusion protein with the immunogenic carrier. A polypeptide of the invention, and/or a biologically active and/or immunogenic fragment, or derivative, or variant thereof, can be provided in an immunogenic composition, for example to raise antisera or monoclonal antibodies for passive immunisation, or as a vaccine. Alternatively, a polypeptide of the invention, fragment, derivative or variant thereof may be useful in an assay to detect antibodies specific for the polypeptide, including diagnostic assays. As set out herein, in embodiments, a derivative of a polypeptide of the invention can be a composite of specific polypeptide sequences of the invention, for example composites of SEQ ID NO 10, SEQ ID NO 11 and a polypeptide as set out in Table 3 or fragments thereof, or nucleotide sequences for example as set out at Table 1 or Table 2 disclosed herein. In embodiments, the nucleic acid sequences can be used to form concatemers and may be used to provide polypeptide sequences, for example relevant epitopes may be put in tandem or provided in multiples of 3, 4, 5, 6, or greater than 10, greater than 20 or more. Further, in embodiments a derivative can include a scrambled or chimeric polypeptide containing combinations of different relevant Rpl polypeptides. In such embodiments the combinations of relevant Rpl polypeptides can be provided in multiples of 2, 3, 4, 5, 6, or greater than 10, greater than 20 or more.

It is important to note that even with knowledge of the genome of R. equi strain 103S, it would not be apparent that R. equi produced pili appendages or that the nine-gene locus encompassing nucleotide positions 1,938,280 to 1,947,152 (locus tags REQ18350-430) encoded a pilus biogenesis apparatus responsible for the production of R. equi pili involved in virulence and host colonisation. Pili are widespread among bacteria and can serve many functions unrelated to virulence. For example pili can facilitate attachment of bacteria to environmental surfaces such as soil particles, biofilm formation, be mediators of bacterial motility or enable adhesion to other bacteria. As will be appreciated, depending on pili function, in some instances, pili may not provide an immunogenic determinant suitable for vaccine development or be able to act as a diagnostic marker.

Using visualisation by electron microscopy and genetic molecular analysis, the inventors demonstrated for the first that R. equi produces pili appendages or fimibriae, identified that the rpl locus R. equi encodes the pilus biogenesis apparatus, and further determined that proteins of R. equi pili are major virulence factors involved in host colonisation and that they are major immunodominant antigens. The latter determination would not have been suggested from sequence data alone.

According to a second aspect of the present invention there is provided an isolated or recombinant nucleic acid encoding a polypeptide associated with pilus formation in R. equi. In embodiments of the invention there is provided an isolated or recombinant nucleic acid comprising a polynucleotide sequence comprising or consisting of a sequence as set forth in any one of SEQ ID NO 1, SEQ ID NO 2, SEQ ID NO 3, SEQ ID NO 4, SEQ ID NO 5, SEQ ID NO 6, SEQ ID NO 7, SEQ ID NO 8, and SEQ ID NO 9 or a variant or derivative or fragment thereof, for example as illustrated in the sequences of FIG. 10.

Due to the known degeneracy of the genetic code, a polynucleotide sequence which differs from those indicated by any one of SEQ ID 1, 2, 3, 4, 5, 6, 7, 8 or 9 can encode an active immunogenic derivative, variant or fragment and/or a biologically active derivative, variant or fragment of a polypeptide of the invention. In embodiments, a polynucleotide sequence which encodes such a derivative, fragment or variant sequence or an immunogenic biologically active derivative or fragment can result from silent mutations (e.g., occurring during PCR amplification), or nucleotide substitutions, deletions or insertions or the like or can be the product of deliberate mutagenesis of a native sequence. Variant polypeptides may be encoded by variant polynucleotide sequences having sequence homology (identity) of greater than at least 85%, 86%, 87%, 88%, 89%, preferably at least 90%, 91%, 92%, 93%, 94%, and more preferably 95%, 96%, 97%, 98%, 99% but less than 100% contiguous nucleotide sequence homology to any one of SEQ ID NO 1, 2, 3, 4, 5, 6, 7, 8, or 9 or fragments thereof. A variant polypeptide may be encoded by a polynucleotide sequence including nucleotide bases not present in the corresponding wild type nucleic acid molecule and/or internal deletions relative to the corresponding wild type nucleic acid molecule, such as SEQ ID NOs 1, 2, 3, 4, 5, 6, 7, or 8. Polynucleotide sequences encoding fragments of a polypeptide of the invention may be greater than 30 nucleotides in length, greater than 50 nucleotides in length, greater than 100 nucleotides in length, or greater than 150 nucleotides in length. The invention also provides isolated nucleic acids useful in the production of polypeptides. Suitably said biologically active immunogenic derivative, fragment or variant can elicit an immune response wherein the antibodies generated to said derivative, fragment or variant have a binding specificity to any one of SEQ ID NO 1, 2, 3, 4, 5, 6, 7, 8 or 9. In embodiments, there can be provided a polynucleotide sequence comprising or consisting of a sequence as set out in any one of SEQ ID NO 1, SEQ ID NO 2, SEQ ID NO 3, SEQ ID NO 4, SEQ ID NO 5, SEQ ID NO 6, SEQ ID NO 7, SEQ ID NO 8, and SEQ ID NO 9.

In further embodiments there is provided an isolated or recombinant nucleic acid comprising a polynucleotide sequence comprising or consisting of a sequence as set forth in any one of SEQ ID NO 1, SEQ ID NO 2, SEQ ID NO 3, SEQ ID NO 4, SEQ ID NO 5, SEQ ID NO 8, and SEQ ID NO 9. In additional embodiments, there is provided an isolated or recombinant nucleic acid comprising a polynucleotide sequence comprising or consisting of a sequence as set forth in any one of SEQ ID NO 2, SEQ ID NO 3, and SEQ ID NO 4. In specific embodiments there is provided an isolated or recombinant nucleic acid comprising a polynucleotide sequence comprising or consisting of a sequence as set forth in SEQ ID NO 2.

Polypeptides of the invention or a biologically active immunogenic fragment, derivative, or variant thereof may be prepared as a pharmaceutical preparation or composition. Such preparations will comprise the polypeptide or a biologically active immunogenic fragment, derivative, or variant thereof and a suitable carrier, diluent or excipient. These preparations may be administered by a variety of routes, for example, oral, buccal, topical, intramuscular, intravenous, subcutaneous, intranasal or the like.

In a third aspect of the present invention, there is provided a composition comprising a polypeptide or antibody according to the invention, or a biologically active immunogenic fragment, derivative, or variant thereof, together with a pharmaceutically acceptable carrier. A carrier and/or excipient useful in a composition of the present invention will generally not inhibit to any significant degree a relevant biological activity of the polypeptide or antibody of the invention. Alternatively, or in addition, the carrier or excipient can comprise a compound that enhances uptake and/or delivery and/or efficacy of the polypeptide and/or antibody as described herein. Alternatively, or in addition, the carrier or excipient can comprise a compound that enhances the activity of a polypeptide and/or antibody as described herein and/or reduces inhibition of said polypeptide or antibody by degradative enzymes in the site of administration and/or on route to the site of action and/or at the site of action. For example, the carrier or excipient may comprise a protease inhibitor and/or a DNase inhibitor and/or an RNase inhibitor to thereby enhance the stability of a polypeptide and/or antibody as described herein above or nucleic acid encoding same.

As will be apparent to the person skilled in the art based on the foregoing description, the methods of the present invention further comprise providing, producing or obtaining a composition comprising a polypeptide and/or an antibody or nucleic acid encoding said polypeptide. Suitable methods for producing such compositions will be apparent to the skilled artisan based on the disclosure herein. A polypeptide can also be delivered with other relevant antigens in a polyvalent protein vaccine.

In certain further aspects, the present invention provides an antibody which has binding specificity to at least one of the polypeptides of the invention or a fragment, derivative, or variant thereof, or an antigen binding fragment of said antibody. Accordingly, in a fourth aspect of the invention there is provided an antibody which specifically binds to a polypeptide of the invention or an epitope, fragment, derivative or variant thereof. Antibodies of the present invention may confer protection against infection with *R. equi*. Additionally or alternatively, an antibody can specifically bind to a polypeptide of the invention or can bind to an epitope of the pili provided on *R. equi* or an *R. equi* antigen of the pili and whilst not conveying protection against infection with *R. equi*, may be a useful in an immunoassay for the detection of polypeptides of the invention or for diagnosis of *R. equi* infection.

In certain embodiments, the antibody can be a polyclonal antibody. Alternatively, the antibody can be a monoclonal antibody, a chimeric antibody, or a synthesized or a synthetic antibody. Methods for producing a polyclonal and monoclonal antibodies are well known in the art and an antibody provided against a polypeptide of the pili is described herein.

In certain further aspects, the present invention further extends to a method of producing an antibody which specifically binds to at least one polypeptide of the present invention, or a biologically active and/or immunogenic fragment, derivative or variant thereof, said method comprising:
  (i) immunising a host with a polypeptide or a fragment, derivative, or variant thereof as described herein according to any embodiment, and
  (ii) recovering antibodies generated by the host against said polypeptide or a fragment, derivative, or variant thereof.

The present invention also provides a method for producing an antibody that binds to an antibody which specifically binds to at least one polypeptide of the present invention or a fragment, derivative, or variant thereof (i.e., a method for producing an anti-idiotypic antibody), said method comprising:
  (i) immunising a host with an antibody that binds to a polypeptide of the invention or a fragment, derivative, or variant thereof or an antigen binding fragment of said antibody,
  (ii) identifying antibodies generated by the host against an antigen binding site of said antibody; and
  (iii) recovering the antibodies identified at (ii).

The present invention also provides an anti-idiotypic antibody that selectively binds to an antibody that binds to a polypeptide or a fragment, derivative, or variant thereof as described herein or an antigen binding fragment of said antibody.

In a fifth aspect of the present invention there is provided a composition comprising an antibody of the invention together with a pharmaceutical carrier.

The invention also provides vectors comprising nucleic acids of the invention and cells comprising such vectors.

In the sixth aspect of the invention there is provided a construct comprising a nucleic acid molecule which encodes a polypeptide of the invention, for example an isolated nucleic acid, or a fragment, derivative, or variant thereof operably linked to a promoter which is functional to allow transcription of the nucleic acid sequence and the expression of an R. equi polypeptide of the invention.

The present invention also provides a process for producing a polypeptide or a fragment, derivative, or variant thereof as described herein according to any embodiment, said method comprising culturing a cell comprising a nucleic acid encoding a polypeptide or a fragment, derivative, or variant thereof of the present invention operably linked to a promoter under conditions suitable for expression of the polypeptide or a fragment, derivative, or variant thereof. A suitable nucleic acid may comprise a polynucleotide sequence or fragment thereof of a gene selected from Table 1, or more preferably Table 2. In one example, the method additionally comprises recovering the polypeptide from the cell culture, e.g., from the medium in which the cell is cultured.

In embodiments the present invention provides a method of producing a polypeptide or a fragment, derivative, or variant thereof of the invention, said method comprising the steps of:
 (i) culturing a host cell comprising a nucleic acid encoding a polypeptide of the present invention or a vector encoding the same, and
 (ii) recovering the polypeptide of the present invention from the host cell or culture medium.

In embodiments, the construct comprises an isolated nucleic acid which encodes a polypeptide of the invention or a fragment, derivative, or variant thereof operably linked to a promoter which is functional in a host cell to allow transcription of the nucleic acid sequence and the expression of a R. equi polypeptide of the invention.

In alternative embodiments, the construct comprises an isolated nucleic acid which encodes a polypeptide of the invention or a fragment, derivative, or variant thereof operably linked to a promoter which is functional in a heterologous host system, for example an attenuated vaccinal strain, including, but not limited to, a microbial system, a virus, a parasite, an attenuated pathogen or normal or immuno-stimulating microbiota. Suitably, the heterologous host system construct may be delivered as a live vaccine alone or in combination with other relevant protective antigens in a polyvalent vaccine.

In embodiments, the construct can comprise a nucleic acid comprising a polynucleotide sequence of a gene selected from at least one gene identified by Table 1, more preferably a gene selected from Table 2, operably linked to a promoter.

In embodiments, the construct can comprise a nucleic acid sequence comprising a polynucleotide sequence of SEQ ID NO 1, 2, 3, 4, 5, 6, 7, 8 or 9, more preferably a polynucleotide sequence which can encode SEQ ID NO 10 or 11.

In a seventh aspect of the invention there is provided a construct of the sixth aspect of the present invention in combination with a pharmaceutical carrier.

In an eighth aspect of the present invention there is provided a composition capable of treating or preventing a disease caused by R. equi, comprising one or more surface-associated (a polypeptide naturally associated to the surface structures or on the outer surface of R. equi.) or secreted polypeptides of R. equi wherein said polypeptides form pili of R. equi. In embodiments the composition can be a vaccine capable of preventing a disease caused by R. equi, which results in the production of antibodies against a polypeptide of R. equi which can form the pili of R. equi and wherein the polypeptide is reactive against antibodies or immune cells recovered from animals repeatedly infected with R. equi.

In embodiments, the polypeptide of R. equi which can form the pili of R. equi, wherein the polypeptide is reactive against antibodies and/or immune cells recovered from animals repeatedly infected with R. equi comprises the amino acid sequence encoded by a polynucleotide sequence of a gene selected from Table 1, or more preferably Table 2 or is an immunogenic fragment or variant or derivative of such a polypeptide.

In embodiments of the invention, the subject for which the vaccine can be administered is a foal and immunisation results in an immune response which inhibits or prevents R. equi infection and results in the production of antibodies employed as an immunogen.

In embodiments the subject to which the vaccine is administered can be a horse and immunisation results in an immune response which inhibits or prevents R. equi., or in the production of antibodies to the polypeptide employed as an immunogen.

While the invention is particularly directed to polypeptide suitable as antigen in a vaccine for use in horses or foals, it will be clearly understood that it is applicable to any other animal which is susceptible to infection with R. equi, including humans, pigs, cattle, sheep, goats, lama, cats or animals which have a similar biology and would be understood to share a high degree of genomic similarity to horses. It will also be appreciated that the diagnostic, therapeutic and prophylactic aspects of the invention are also applicable to subjects which have been exposed to an animal infected with R. equi, or an environmental source contaminated with R. equi such as faeces, soil, or the like.

According to a ninth aspect of the present invention there is provided a method of treating or preventing a disease or condition caused by R. equi comprising the step of administering a polypeptide of the invention or a fragment, derivative, or variant, an antibody, a nucleic acid, composition and/or a vaccine of the invention to subjects suffering from, or suspected to be suffering from, or at risk of a condition mediated by R. equi.

There is provided the use of a polypeptide of the invention or a biologically active and/or immunogenic fragment, derivative, or variant, an antibody, a nucleic acid, composition and/or a vaccine of the invention in the preparation of a medicament for the treatment of a condition mediated by R. equi. In embodiments the treatment may be prophylactic treatment to prevent or inhibit infection.

There is provided a polypeptide of the invention or a fragment, derivative, or variant, an antibody, a nucleic acid, composition and/or a vaccine of the invention for use in the treatment of a condition mediated by R. equi. In embodiments the treatment may be prophylactic treatment to prevent or inhibit infection.

According to a tenth aspect of the present invention there is provided a method of detecting R. equi comprising the step of detecting a polypeptide of the invention or a fragment, derivative, or variant, or an antibody of the invention in a sample, or a polynucleotide of the invention which can encode a polypeptide of the invention or fragment thereof. In embodiments, a sample may be a soil sample.

In embodiments, there is provided a method of diagnosing a disease or condition caused by R. equi comprising the step of detecting a polypeptide of the invention or a fragment, derivative, or variant, or an antibody of the invention in a biological sample from a subject suffering from, suspected to be suffering from, or at risk of such a condition, or a polynucleotide of the invention which can encode a polypeptide of the invention or fragment thereof.

Detection of a polypeptide or an antibody of the invention may be achieved by a variety of methods, including but not limited immunoassay methods such as radioimmuno assay, enzyme linked immunoabsorbent assays (ELISA), chemiluminescence assays, immunohistochemistry, immunoblotting, for example Western blotting, immunofluorescence and mass spectrometry. An example of use of an antibody to detect a polypeptide of a R. equi pili (RplB) is provided in the Examples herein.

Suitably, detection of antibodies with binding specificity to a polypeptide encoded by any one of SEQ ID NO 1, 2, 3, 4, 5, 6, 7, 8, or 9 may be used as a test for R. equi in horses. In embodiments, PCR testing for nucleic acids encoding a polypeptide of the pili, for example as encoded by any one of SEQ ID NO 1, 2, 3, 4, 5, 6, 7, 8, or 9 may be used as a test for R. equi, particularly where a quantitative detection is preferred. Based on the nucleic acid sequence data provided herein, suitable primers or probes for use in the detection of nucleic acid sequences which can encode polypeptides of the pili of R. equi could be provided as would be understood in the art. As will be understood, suitably, in embodiments, said probes or primers can hybridise to the nucleic acid sequences encoding peptides associated with pilus formation, preferably any one of SEQ ID NO 1, 2, 3, 4, 5, 6, 7, 8, or 9, under stringent conditions. Hybridisation refers to the binding, duplexing, or hybridizing of a molecule only to a particular nucleotide sequence under stringent conditions when that sequence is present in a complex mixture (e.g., total cellular) DNA or RNA. Stringent hybridisation occurs when a nucleic acid binds the target nucleic acid with minimal background. Typically, to achieve stringent hybridisation, temperatures of around 1° C. to about 20° C., more preferably 5° C. to about 20° C. below the Tm (melting temperature at which half the molecules dissociate from their partner) are used. However, it is further defined by ionic strength and pH of the solution. An example of highly stringent wash conditions is 0.15 M NaCl at 72° C. for about 15 minutes. An example of a stringent wash condition is a 0.2×SSC wash at 65° C. for 15 minutes (see, Sambrook and Russell, infra, for a description of SSC buffer). Often, a high stringency wash is preceded by a low stringency wash to remove background probe signal. An example of a medium stringency wash for a duplex of, for example, more than 100 nucleotides, is 1×SSC at 45° C. for 15 minutes. An example of a low stringency wash for a duplex of for example more than 100 nucleotides, is 4-6×SSC at 40° C. for 15 minutes. For short probes (for example about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (for example, >50 nucleotides). Detection of a polynucleotide of the invention may be by any suitable means, for example using PCR, a microarray or the like as would be known in the art.

In an eleventh aspect of the present invention there is provide a kit to detect R. equi wherein the kit comprises a polypeptide or antibody of the invention or a nucleic acid probe. In embodiments a kit can comprise a polypeptide or antibody of the invention.

In embodiments, the kit is for use in the method of diagnosing a disease or condition caused by R. equi wherein the kit comprises a polypeptide or antibody of the invention or a nucleic acid probe. In embodiments a kit can comprise a polypeptide or antibody of the invention.

In embodiments, the kit can include a solid support, for example a test strip, plastic bead or the like to which polypeptide or antibody of the invention can be coated. The kit may include a detection antibody capable of binding to a polypeptide or antibody of the invention which comprises a detectable label or binding site for a detectable label. Suitably a labelling molecule can include an enzyme, fluorescent label or radiolabel. Binding sites for detectable labels include avidin, biotin, streptavidin and the like.

Additionally, the kit can include instructions for using the kit to practise the present invention. The instructions should be in writing in a tangible form or stored in an electronically retrievable form. A further aspect of the present invention provides a method of screening immunogenic R. equi polypeptides of the invention or a fragment, derivative, or variant thereof to determine if a test agent can bind to said polypeptide comprising the steps: providing a candidate immunogenic R. equi polypeptide of the invention or a fragment, derivative, or variant thereof, providing a test agent to the candidate immunogenic R. equi polypeptide and determining whether said test agent can bind to said candidate immunogenic R. equi polypeptide.

A test agent which can bind to a R. equi polypeptide of the invention may inhibit the activity of said polypeptide, minimise its secretion or inhibit its ability to form functional pili. In embodiments, such a test agent may be a useful therapeutic.

The present invention also provides the use of a polypeptide or a fragment, derivative, or variant thereof or an antibody as described herein in medicine.

In a twelfth aspect, the present invention provides the use of a polypeptide of the invention or a fragment, derivative, or variant thereof, an antibody, composition and/or vaccine of the invention in the treatment or prevention of a disease or condition caused by R. equi.

In one embodiment of the invention, a method of treatment comprises the steps:
 (i) identifying a subject suffering from a disorder associated with or R. equi or at risk of developing R. equi;
 (ii) administering a polypeptide, or composition as described herein to said subject.

In another embodiment, the invention provides a method of treatment comprising administering or recommending a polypeptide, or a fragment, derivative, or variant thereof or an antibody or composition as described herein to a subject previously identified as having R. equi infection or suffering from a condition associated with R. equi infection. The invention may also provide a method of treatment of a subject in need thereof, said method comprising:
 (i) identifying a subject suffering from a disorder associated with or R. equi or at risk of developing R. equi;
 (ii) obtaining a polypeptide or a fragment, derivative, or variant thereof as described herein according to any embodiment,
 (iii) formulating the polypeptide or antibody with a suitable carrier and/or excipient to form a composition wherein said composition is in an amount sufficient to reduce or prevent or inhibit R. equi infection or suffering from a condition associated with R. equi infection and
 (iv) administering said composition to said subject.

In a further embodiment there is provided a method of treatment of a subject in need thereof, said method comprising:
(i) identifying a subject suffering from a disorder associated with or *R. equi.* or at risk of developing *R. equi.;*
(ii) obtaining a polypeptide or a fragment, derivative, or variant thereof or an antibody as described herein according to any embodiment,
(iii) formulating the polypeptide or antibody with a suitable carrier and/or excipient to form a composition wherein said composition is in an amount sufficient to reduce or prevent or inhibit *R. equi* infection or suffering from a condition associated with *R. equi* infection and
(iv) recommending administration of a composition at (iii).

In embodiments a polypeptide on the invention can be provided to a subject to generate a protective immune response in the subject. In particular embodiments the polypeptide may act as a vaccine.

Sequences identified in the patent application include:

SEQ ID NO 1
rpIA REQ_18350> - 3104103:3104891
```
GTGATCGTCGCAGCGGGCGTCGGCGCCGCACTCCTGGGTATCCTCG

CCGGGGCGTTCGCGAACAGTGCGATCGACCGCGTGCGCCTGGAGA

CCGCGTGCGCCGAGCCGAAGTCGACCCCCACCGGCTCAACCCCGC

CGCCCCCCTCCCCTGCGTCCGCGGTAGCCACCCGGATCGCGATGAT

CGACACCATCACGCGACGACACGACATCAGTGCCCGCCGCGTGCTC

GTCGAACTCGCAACGGCCCTCCTGTTCGTCGGGATCACTCTCCGTCT

CGCCGCTCTCGGTCTTCTCCCGGCAACACCGGCCTATCTCTTGCAAA

CGGCTGCCGAACTTCCTCGTCGTACCGTCGTACCCGATCGTATTCGC

CTGCCTTTCAGTGGGTTCCGTCGTGCCGTTCTGTTCGGGGTCTACTT

CGTACTAGCCCTGATCTATCCGGCCGGCATGGGGTTCGGCGACGTC

AAACTTGCCGGCGTCATCGGCGCCGTCCTCGCCTACCTGTCGTACG

GCACATTGCTCGTCGGGGCGTTTCTCGCGTTCCTGGTGGCCGCACT

CGTCGGCCTGATCATCCTGGTCACCCGTCGCGGTCGGATCGGGACC

ACGATTCCCTTCGGGCCGTACATGATTGCGGCGGCCATCGTTGCGAT

CCTGGCGGCCGATCCGCTGGCGCGCGCGTATCTGGACTGGGCCGC

CGCGGCCTGA
```

SEQ ID NO 2
rpIB REQ_18360> - 1939395:1939601
```
ATGAACCTCTTCTTCGCGAACCTGTACCTCATGGGCTTAGACGTCAA

GGACCGTCTGACCCGTGACGACCGCGGCGCCACTGCGGTCGAGTAC

GGACTGATGGTCGCCGGCATCGCGATGGTGATCATTGTTGCGGTTTT

CGCCTTCGGCGATAAGATTACCGACCTCTTCGATGGCTTCAACTTCG

ACGATCCCGGCGGCGAGTAG
```

SEQ ID NO 3
rpIC REQ_18370> - 1939683:1940084
```
ATGAAGCGCCTCACTTCCGATTCAGGGGTCGCCGCAGTCGAATTCGC

TCTCGTCGTTCCGATCCTGATCACACTGGTCCTCGGCATCGTGGAGT

TCGGTCGGGGTTACAACGTCCAGAACGCGGTCAGCGCTGCTGCCCG

CGAGGGTGCACGGACGATGGCGATCAAGAAGGATCCGGCGGCGGC
```

GCGTGCTGCCGTGAAGGGCGCGGGTGTGTTCAGTCCGGCGATCACC

GATGCGGAGATCTGCATCAGCACTTCGGGAACGCAGGGCTGTTCGG

CAACGTCGTGTCCGAGCGGAAGTACCGTGACGCTCACGGTCAGCTA

TCCACTCGAGTACATGACGGGACTCTTTCCCGGTAAGCCGACGCTCA

CCGGCACGGGGGTCATGCGATGCGGTGGGTGA

SEQ ID NO 4
rpID REQ_18380> - 1940093:1941037
```
ATGTCGAATGACGAGCGCGGGGTCGTCGCCGTGCTCGTTGCGATCC

TCATGGTCGTGCTCCTGGGATGTGCTGCGATCTCGGTCGACATCGGT

GCGAACTATGTCGTCAAACGTCAGTTGCAGAACGGGGCCGATGCGG

CTGCGCTCGCCGTAGCTCAGGAATCCAGTTGCAAGGCAGGATCTTCC

GCCTCATCCGTGTCGAGCCTTGTCCAGGCGAACGTCAACAGCTCGTC

GGCTGCAAGTGCGGCGGTGATCGACGGTGTGAAGCGGAAGGTGAC

GGTCACTGCGTCGGCGGTGGGTGACGACGGCCTCGCCGGCCGGAG

GAACGTGTTCGCTCCGGTCCTCGGAGTCGACCGCAGCGAGATCTCG

GCGTCTGCGACTGCAAGCTGCGTGTTTCCCCTCGGGGGGACCGCGG

AACTCCCGCTCACGTTCCACAAGTGCCATTTCGACGAATCCCGCAGT

CTGGACGTGAAGATCCTCGTCGCCTACAACGTGACGGCGCCGCGCT

GCAATGGAACCTCGGGAAATGCGGCACCGGGCAATTTCGGCTGGCT

GCAGGGGGCGAACGGTCGATGCCCGGCGAAGATCGACGCCGCCGT

CTACGCAACACCGGGCGACACCGGTAACAACATTCCGGGGCCGTGC

AAGGACACCATCAAGCAGTTTCAGAATGCCGTCGTGCGGGTCCCGAT

CTACGACGTCGCAGGTGGAACCGGAAGCGGTGGATGGTTTCACGTC

GTCGGTTTGGCTGCCTTCAAGATTCAGGGCTACCGGCTGAGCGGCA

ACCCGGAGTTCAACTGGAACAACGATGTTCACGGGGCGCTGAGTTG

CACCGGCAGCTGTCGCGGCATCATCGGCACCTTCGTGAAGATTGTCA

GCCTCGATTCGGATCTGACGCCGGGAGGGATCGATTTCGGCGTGAG

TACGATCAGCTTGCTCGATTAG
```

SEQ ID NO 5
rpIE REQ_18390> - 1941047:1941784
```
TTGAGAACCCGAATCATTGCTGCGATCTGTGCGATCGTTCTCGCGGT

CGCGGGAACCCTCGCCCTGATCTCGTATGTACGCGGGCCGATGCC

CGCGCCCTGGCGGGTACACGCACCGTCGATGTGCTCGTCGCCGATC

AGACGATTCCGAAGAACACTCCCGCTGATTCGCTCGTGGGAATGGTT

GTGGTCAAGAAACTTCCGGAAATGGCGGTGCTACCCGATCGGGTGA

CCAGTCTCGACCAACTGTCCGGCAAGGTCGCGCTGACCGACCTCCT

GCCTGGCGAACAACTGGTCTCGGCGCGATTCGTCGACCCGGCGACC

GCCCGAAGTCAGGACCAGGGAGGAATCCCCGAGGGGATGCAGGAG

GTGACGGTTCTTCTCGAGCCGCAACGCGCACTGGGAGGCCACATCG

CGTCGGGCGATACCGTCGGCGTCTTCATGTCCTTCTCGCCGCCCGT

CAAGAACTACGAAACACATCTGAGATTGCAGAAAGTGCGAGTCACGC

GGGTCCAGGGAACGTTCTCCAACGCCGACGAAGGGGATTCGGCCAC

GGTCGACTCGTCGCCGAGCCCTGCTCCCACCGAGGCCTTTCTCGTC
```

-continued
```
TCGCTGGCGGTCGACGTGCCGATGGCGGAGCGCGTCGTTTTCGCCG
CGGAGCACGGGACCATCTGGCTTTCCAATGAGCCGCCGAGTTCGAA
CGAGGCCGGGGCATCCGTGGTCTCCCCGGAAGGAGTGTTCCGATGA
```

SEQ ID NO 6
rpIF REQ_18400> - 1941781:1942980
```
ATGAGCCGCATCGTCCTGCTGACCGATCGCGACGATTTCGCCCGCC
GCGTGTACCACGCCGCGGACGGCAACCTTCTGGTGTTGCCGGCGCA
GCCGGTTCCCCGGGGGCCGGCGCAGTTGGTCGGGCTCGGCGTGAC
CGTGCAACCAGAAGTTCTCGTTCTCGGTCCGGACGTGCCGGAAGTG
GAGGGCCTCTCCCTCGCCGGCCGGATCGATCATTCGACGCCCGGCA
CCACGGTGGTTCTGGCCAGTGATGCGGGCACCGACGTGTGGTTGCG
GGCGATGCGCGCCGGCGTGCGGGACGTGATGTCGCCGGAGGCGGA
GATCGCGGACGTTCGTGCGGTACTCGATCGAGCGGGCCAGGCCGCA
CTGGCGCGACGTCAGGGGGCGAGTGCACCGGCGGAGCAGCATGCG
GTTCAAGGGAAGGTCATCGTGGTCGCGTCGCCGAAAGGCGGAACCG
GAAAGACCACCGTTGCGACGAATCTTGCAGTAGGACTCGCGGCGGC
AGCGCCTCACTCGACGGTGTTGGTGGACCTCGACGTGCAGTTCGGG
GACGTTGCCAGTGCTCTCCAGTTGGTTCCGGAACATTGCCTGACCGA
CGCCGTCGCGGGCCCGGCCAGCCAGGACATGATCGTCCTCAAGACC
GTCCTGACACCCCATTCCACAGGACTGCATGCGCTGTGTGGGTCGG
ACTCGCCCGCGGCGGGCGACAGCATCACCGGCGAGCAGGTGAGCA
CTCTGCTGACGCAGTTGGCGGCCGAATTCCGGTACGTGGTCGTCGA
CACCGCGCCCGGTTTGCTCGAACACACCCTGGCGGCGCTCGACCTT
GCTACCGACGTCGTGTTGGTGTCGGGTATGGACGTGCCCAGCGTCC
GCGGGATGCACAAGGAACTGCAATTGCTGACGGAGCTGAATCTGGG
TCCGGTCGTGCGGCATGTCGTGCTCAACTTTGCGGATCGACGCGAG
GGGCTGACGGTCCAGGACATCCAGAACACCATCGGGGTCCCCGCCG
ATATCGTGATCAAGCGCTCGAAAGCCGTTGCCCTCTCGACGAACCGG
GGGGTTCCACTGCTTCAGAACCCGGGTCGGGATCGCACTGCGAAAG
AGTTGTGGCGACTCGTCGGCCGTATCGATCCGGCTCCCGATACCGC
CAAGGGTGGACGCGCGCGGCATCGGGCAGCCGAGGCGGTGGGTGC
GAAATGA
```

SEQ ID NO 7
rpIG REQ_18410> - 1942977:1944374
```
ATGAGACTGTCCCAACGGCTCGAGGCCGTGCGCGGAGCCGCACCC
GTCGAAGCCGCCGCACCGATCCCGCCGGGGAAGCAGGGGAAGGCG
AAAACGTCCCTCCCTCCGGCCGACGCTCTCGCCGAACTGAAGGACC
GTGCGAGTGCGGCCCTGTACACCCGGATCGGCACCCGCTTCAACGA
CTCCTCGTTGAGCGAGGAGCAACTGCATCCTGGTCCGTGAGGAA
CTGGCCGAAATCGTGGAGCAGGAGACGACGCCACTCACCTTCGACG
AACGGCAGCGCCTGCTCCGTGAGGTTGCCGACGAGGTACTGGGGCA
CGGACCGCTCCAGCGGCTACTGGAGGACCCGTCGGTCACCGAGATC
```
-continued
```
ATGGTCAACAGCCACGACATGGTCTACGTCGAGCGGGACGGCACCC
TCGTCCGCAGCTCCGCGCGATTCGCGGACGAGGCGCACCTGCGTCG
CGTGATCGAACGCATCGTTTCCGCCGTCGGTCGACGGATCGACGAA
TCGTCCCCGCTCGTGGATGCACGCTTGGCGGATGGCTCCCGTGTCA
ACGCGGTGATCCCACCGCTCGCATTCAACGGCTCCTCGCTCACCATT
CGAAAGTTCTCGAAAGATCCGTTCCAGGTCGACGATCTCATCGCCTT
CGGCACTCTCTCGCACGAGATGGCCGAACTGCTCGACGCGTGTGTG
CAGGCGCGACTGAACGTCATCGTCTCGGGCGGCACGGGCACGGGG
AAGACGACGCTGCTCAACGTGCTCTCGTCGTTCATTCCGGAAGGGGA
GCGGATCGTCACCATCGAGGACGCCGTGGAACTGCAACTTCAGCAG
GACCACGTCGTACGGTTGGAGAGCCGACCGCCGAACATCGAGGGCA
AGGGTGCCGTCACCATCCGCGACCTGGTGCGGAACTCGCTGCGTAT
GCGTCCCGACCGCATCGTGGTGGGGAGTGTCGCGGAGGCGAGAG
TCTCGACATGCTGCAAGCGATGAACACCGGTCACGACGGGTCGCTG
TCGACGGTGCATGCGAATTCGCCCCGTGACGCCATCGCGCGCTTGG
AGACGCTCGTGTTGATGGCCGGCATGGACCTGCCGTTGCGGGCGAT
CCGGGAGCAGATTGCTTCGGCGGTCGACGTGATCGTGCAGCTCACT
CGACTACGTGACGGCACTCGGCGAGTGACCCACGTGACCGAGGTCC
AGGGCATGGAGGGTGAGATCGTCACCCTGCAGGATGCCTTCCTGTT
CGACTACAGCGCCGGCGTCGACGCGCGCGGGCGATTCCTCGGCAG
ACCGCAGCCGACCGGAGTGCGGCCGCGGTTCACCGACAGATTCCGA
GATCTCGGTATTGCTTTGTCGCCGAGTGTTTTCGGGGTGGGAGAACC
CTCCCGGGGCGGGTATGA
```

SEQ ID NO 8
rpIH REQ_18420> - 1944371:1946239
```
ATGAGCCGGTGCGTGGTGGCCGTCGTGCTCGCCCTCGGTGCGGGT
GTTCTGGGAATTCCCGCCGTAGCCGCGGCGGCCGAGGAGGCTGTCC
AGGTCTCGGCGGTCGACACGACCCGGTTTCCCGACATCGAGGTGTC
CATCCTCGCGCCGCCCGGTATCGAAGGGCAGGCGATCGATCCGGGA
ACGTTCGCGCTCACCGAGGGCGGCGTGCCGCGAGAGATCGAGGTC
AGGCAGCAGCCGGGTTCCGAGCAGGACATCGTGCTCGCAATCGACG
TGTCCGGGGGCATGTCGGGTCCGGCGCTGGACGACGTGAAGCGCG
CCGCATCGGATTTCGTGCGGCAGGCGCCGGCCGGCGCCCACATCG
GAATCGTCGCGATCTCGTCGACGCCACAGGTGCTCTCGGAACTGAC
GACGGACTCCGAGGACCTGCTCCGCAGGATCGACGGACTGAAGGCG
GGCGGCAACAGCGCGATCGCAGATTCGGTGGTGACCGCCGCCGAG
ATGCTCGAGCGCGGCGAAGCGGCCAACAACATCCTGCTTCTGTTGA
CGGACGGCGCCGACACGTCGAGTGCACACTCGATGTCGGAACTCCC
GTCCGTCCTGAGTCGGTCGCGCGCGTCGCTGTACGCCGTGCAGATG
TCGACACCCGAGACGAACTCTGCTCTCCTGCAGCAGGTTGCGCGGG
AGTCGCGCGGTCAGTACGCGTCTGCGGGTGATACGGCGGCGCTGG
GTGCGATCTACCAGTCGGCCGCTCGCGCGCTCGGAAACCTGTACGT
```

-continued
```
CGTCCGATACCGATCGGAAGCGAATGGCGATACCCAGGTGGTGGCG
AGCGTGCGCAGCGGCGCAGCCGGCCGAGTGAGCGATCCGTTCCCG
GTGACATTGCCCGGTGTGGTGCCGACGCCGAGCGTCGTCGCCGGG
ACCGTCGACGGTTTCTTCACGTCTTCGACGGGGCTGGTGATCGGC
TCCTAGCGTGCTACTCGGCGCTTGCGGGAGGCGTGCTGGCGGTCGC
CGGTAGAGCGCCCGCGAGGATTTCGGCAGCACGTCGTGGGCGGCA
GGACGGACGGGACTCGATGCTGTCCCGATTCGCGGAACGGCTGGTG
CAGTGGATCGATCAGAACCTGAGGAGACGCGGACGCATCGCTGCCC
GCACCCAGGCGCTACAGGAGGCGGGGCTGAAGCTTCGTCCAGGTGA
CTTCATCGCCCTGGTCGGTGCTGCGGCGATCACCGCTGCGGCGATC
GGTCTCCTGGCTTCGGGCATCGTGGCGGCGCTCTTGCTCGCGGCGA
TCACAGTGGATTGTCGAGAATCTATCTCCGTGTGATGGCCGGTAGG
CGTCGGGCCGCGTTCGCTGATCAGCTCGACGATTCCCTGCAGCTGC
TGGCCAGCAATCTCCGAGCCGGGCACAGCATGCTCCGAGCGCTCGA
TTCCCTTTCCCGAGAGGCGGAGGTGCCGACTTCGGAGGAGTTCGCT
CGGATCGTCAACGAGACTCGGGTGGGACGTGATCTCAACGAGTCTC
TCGACGACGTGGCCCGGCGGATGCGAAGTGACGATTTCAACTGGAT
AGCTCAGGCAATCGCCATCAACCGTGAGGTCGGAGGCGACCTCGCG
GAAGTCCTCGACCAGGTGGGCAACACCATTCGAGAGCGAAATCAGAT
TCGACGGCAGGTGAAAGCCCTTGCTGCCGAGGGGAAACTGTCCGCC
TACGTGCTGATGGCGCTGCCCTTCGGTCTCACCGCATTTCTGCTCGT
CTCGAATCCGGACTACCTGTCGAAGTTGACGGGTAGCGCCATCGGC
TACGTGATGATCGCGGTGGGGCTCGTCATGCTGACCGTCGGTGGGC
TGTGGATGAACAAGGTTGTCTCGGTCAAGTTCTAG
                                          SEQ ID NO 9
rpII REQ_18430> - 1946262:1947152
GTGATTCCACCGCTGGTGCTCATGGCGGCGCTGTCCGTCGGCGGGG
CGTTGGGTGTTCTGGTGTGGTTGACGGTCGGCGCCCGAGATCCGGA
ACGCGGACCCGCCCTTCGGAACCTGCAGTCGCAGCTGGCGTTGCCG
ATTCCGGAGTCGGGAGGCGCGCCACCGCTTTCGCTCGGCCGATTCG
TGAAGCTGCTGTCGCCGCCCGGGACGATGGCCCGCTTGGAACGACT
GCACATCCTTGCCGGTCGTCCAGCGGCGTGGGTTCCGGAACGGGCC
GCGATGGCGAAGATCGTTCTCGCCGCGGCCGCCGCCCTGCTCGGC
CTTCTCGCGGTGGGTGCGTCGCCTGGCGTCGGCCGGGTGCTGTTCG
CTGCGGCCGCCGTCGCGCTGGCGTATTTCGTCCCGGAACTTCTCCT
GCAGAGCAGGGGGCAGGAGCGCCAAGCCGCGATCGAACTGGCGCT
TGCCGACACCCTCGACCAGATGACGATCGCAGTCGAGGCGGGCCTG
GGGTTCGAAGCCGCCATGCAGCGGGCCGCGAAGAACGGAAAGGGG
CCGCTGGCCGAGGAATTCATCCGGACATTGCAGGACATACAGATGG
GGCAGTCGAGGCGAATCGCGTACCTGGATCTTGCCGCCAGAACGAA
AGCACCCAACTTGCGGAGGTTCCTTCGGGCCGTCATCCAAGCCGAC
GAGTACGGCGTGGCCATCGCCGAGGTCCTGCGGACCCAGGCCTCG
GAGATGCGTCTGAAACGCCGTCAGAGTGCTGAGGAGAAGGCGATGA
AGGTTCCGGTGAAGGTGCTGTTTCCGTTGATGACCTGCATCCTGCCG
ACCATCTTCATCGTGATCCTGGGTCCGGCGGTGATCAACATGATGGA
GGTCTTGGGCGGTATGTAA
                                          SEQ ID NO 12
RpIA:
VIVAAGVGAALLGILAGAFANSAIDRVRLETACAEPKSTPTGSTPPPPSP
ASAVATRIAMIDTITRRHDISARRVLVELATALLFVGITLRLAALGLLPA
TPAYLWFAAVGIALAVIDIDCKRLPNFLVVPSYPIVFACLSVGSVVTGDW
SALLRAAIGAAVLFGVYFVLALIYPAGMGFGDVKLAGVIGAVLAYLSYGT
LLVGAFLAFLVAALVGLIILVTRRGRIGTTIPFGPYMIAAAIVAILAADP
LARAYLDWAAAA
                                          SEQ ID NO 13
RpIB:
MNLFFANLYLMGLDVKDRLTRDDRGATAVEYGLMVAGIAMVIIVAVFAFG
DKITDLFDGFNFDDPGGE
                                          SEQ ID NO 14
RpIC:
MKRLTSDSGVAAVEFALVVPILITLVLGIVEFGRGYNVQNAVSAAAREGA
RTMAIKKDPAAARAAVKGAGVFSPAITDAEICISTSGTQGCSATSCPSGS
TVTLTVSYPLEYMTGLFPGKPTLTGTGVMRCGG
                                          SEQ ID NO 15
RpID:
MSNDERGVVAVLVAILMVVLLGCAAISVDIGANYVVKRQLQNGADAAALA
VAQESSCKAGSSASSVSSLVQANVNSSSAASAAVIDGVKRKVTVTASAV
GDDDGLAGRRNVFAPVLGVDRSEISASATASCVFPLGGTAELPLTFHKCH
FDESRSLDVKILVAYNVTAPRCNGTSGNAAPGNFGWLQGANGRCPAKI
DAAVYATPGDTGNNIPGPCKDTIKQFQNAVVRVPIYDVAGGTGSGGWF
HVVGLAAFKIQGYRLSGNPEFNWNNDVHGALSCTGSCRGIIGTFVKIVSL
DSDLTPGGIDFGVSTISLLD
                                          SEQ ID NO 16
RpIE:
LRTRIIAAICAIVLAVAGTLALISYVRGADARALAGTRTVDVLVADQTIP
KNTPADSLVGMVVVKKLPEMAVLPDRVTSLDQLSGKVALTDLLPGEQLVS
ARFVDPATARSQDQGGIPEGMQEVTVLLEPQRALGGHIASGDTVGVFMSF
SPPVKNYETHLRLQKVRVTRVQGTFSNADEGDSATVDSSPSPAPTEAFL
VSLAVDVPMAERVVFAAEHGTIWLSNEPPSSNEAGASVVSP
EGVFR
                                          SEQ ID NO 17
RpIF:
MSRIVLLTDRDDFARRVYHAADGNLLVLPAQPVPRGPAQLVGLGVTVQP
EVLVLGPDVPEVEGLSLAGRIDHSTPGTTVVLASDAGTDVWLRAMRAGV
RDVMSPEAEIADVRAVLDRAGQAALARRQGASAPAEQHAVQGKVIVVA
SPKGGTGKTTVATNLAVGLAAAAPHSTVLVDLDVQFGDVASALQLVPEH
CLTDAVAGPASQDMIVLKTVLTPHSTGLHALCGSDSPAAGDSITGEQVST
LLTQLAAEFRYVVVDTAPGLLEHTLAALDLATDVVLVSGMDVPSVRGMH
```

-continued

KELQLLTELNLGPVVRHVVLNFADRREGLTVQDIQNTIGVPADIVIKRSK

AVALSTNRGVPLLQNPGRDRTAKELWRLVGRIDPAPDTAKGGRARHRAA

EAVGAK

SEQ ID NO 18
RpIG:
MRLSQRLEAVRGAAPVEAAAPIPPGKQGKAKTSLPPADALAELKDRASA

ALYTRIGTRFNDSSLSEEQLHLLVREELAEIVEQETTPLTFDERQRLLRE

VADEVLGHGPLQRLLEDPSVTEIMVNSHDMVYVERDGTLVRSSARFADEA

HLRRVIERIVSAVGRRIDESSPLVDARLADGSRVNAVIPPLAFNGSSLTI

RKFSKDPFQVDDLIAFGTLSHEMAELLDACVQARLNVIVSGGTGTGKTTL

LNVLSSFIPEGERIVTIEDAVELQLQQDHVVRLESRPPNIEGKGAVTIRD

LVRNSLRMRPDRIVVGECRGGESLDMLQAMNTGHDGSLSTVHANSPRDAI

ARLETLVLMAGMDLPLRAIREQIASAVDVIVQLTRLRDGTRRVTHVTEVQ

GMEGEIVTLQDAFLFDYSAGVDARGRFLGRPQPTGVRPRFTDRFRDLGI

ALSPSVFGVGEPSRGRV

SEQ ID NO 19
RpIH:
MSRCVVAVVLALGAGVLGIPAVAAAAEEAVQVSAVDTTRFPDIEVSILAP

PGIEGQAIDPGTFALTEGGVPREIEVRQQPGSEQDIVLAIDVSGGMSGPA

LDDVKRAASDFVRQAPAGAHIGIVAISSTPQVLSELTTDSEDLLRRIDGL

KAGGNSAIADSVVTAAEMLERGEAANNILLLLTDGADTSSAHSMSELPSV

LSRSRASLYAVQMSTPETNSALLQQVARESRGQYASAGDTAALGAIYQSA

ARALGNLYVVRYRSEANGDTQVVASVRSGAAGRVSDPFPVTLPGVVPT

PSVVAGTVDGFFTSSTGLVIGLLACYSALAGGVLAVAGRAPARISAARRG

RQDGRDSMLSRFAERLVQWIDQNLRRRGRIAARTQALQEAGLKLRPGD

FIALVGAAAITAAAIGLLASGIVAALLLAAITVGLSRIYLRVMAGRRRAA

FADQLDDSLQLLASNLRAGHSMLRALDSLSREAEVPTSEEFARIVNETRV

GRDLNESLDDVARRMRSDDFNWIAQAIAINREVGGDLAEVLDQVGNTIRE

RNQIRRQVKALAAEGKLSAYVLMALPFGLTAFLLVSNPDYLSKLTGSAIG

YVMIAVGLVMLTVGGLWMNKVVSVKF

SEQ ID NO 20
RpII:
VIPPLVLMAALSVGGALGVLVWLTVGARDPERGPALRNLQSQLALPIPES

GGAPPLSLGRFVKLLSPPGTMARLERLHILAGRPAAWVPERAAMAKIVLA

AAAALLGLLAVGASPGVGRVLFAAAAVALAYFVPELLLQSRGQERQAAIE

LALADTLDQMTIAVEAGLGFEAAMQRAAKNGKGPLAEEFIRTLQDIQMG

QSRRIAYLDLAARTKAPNLRRFLRAVIQADEYGVAIAEVLRTQASEMRLK

RRQSAEEKAMKVPVKVLFPLMTCILPTIFIVILGPAVINMMEVLGGM

Preferred features and embodiments of each aspect of the invention are as for each of the other aspects mutatis mutandis unless context demands otherwise.

Each document, reference, patent application or patent cited in this text is expressly incorporated herein in their entirety by reference, which means it should be read and considered by the reader as part of this text. That the document, reference, patent application or patent cited in the text is not repeated in this text is merely for reasons of conciseness. Reference to cited material or information contained in the text should not be understood as a concession that the material or information was part of the common general knowledge or was known in any country.

Throughout the specification, unless the context demands otherwise, the terms 'comprise' or 'include', or variations such as 'comprises' or 'comprising', 'includes' or 'including' will be understood to imply the includes of a stated integer or group of integers, but not the exclusion of any other integer or group of integers.

By "consisting essentially of" it is meant that a nucleic acid does not include additional, substituted or deleted nucleotide(s) to a polynucleotide sequence of the invention described herein or a polypeptide does not include additional, substituted, or deleted amino acids which significantly alter the character of a sequence of the invention such that it is not immunogenic and biologically active.

As used herein, the singular forms "a", "an", and "the" include the corresponding plural reference unless the context clearly dictates otherwise.

Where a range of values is expressed, it will be understood that this range encompasses the upper and lower limits of the range and all values in between these limits.

The terms "polypeptide", "protein" and "peptide" are herein used interchangeably.

The term "isolated" refers to materials, such as nucleic acid molecules, which are substantially free or otherwise removed from components that normally accompany or interact with the materials in a naturally occurring environment. An isolated nucleic acid typically contains less than about 50%, preferably less than about 75%, and most preferably less than about 90% of the components with which it was originally associated. Polypeptides, antibodies and nucleic acids of the invention as disclosed herein can be isolated.

The terms "polynucleotide", "polynucleotide sequence", and "nucleic acid sequence" are used interchangeably herein. A "polynucleotide" as used herein refers to purine- and pyrimidine-containing polymers of any length, either polyribonucleotides or polydeoxyribonucleotides, which can be single or double stranded, such as, for example, DNA-DNA, DNA-RNA and RNA-RNA. A polynucleotide may optionally contain synthetic, non-natural or altered nucleotide bases. A polynucleotide in the form of a polymer of DNA may be comprised of one or more strands of cDNA, genomic DNA, synthetic DNA, or mixtures thereof.

A "derivative" of a polypeptide as used herein will be understood to include polypeptides which have been subject to chemical modifications, including esterification, amidation, reduction, methylation, fusion to another peptide and the like. The polypeptide derivatives may be modified such that the modifications increase the stability and/or immunogenicity and/or bioavailability of the polypeptide derivative in comparison to the unmodified polypeptide. Covalent derivatives of the peptides or polypeptides of the invention can be prepared by linking the chemical moieties to functional groups on the amino acid side chains or at the N-terminus or C-terminus of the antigenic polypeptide. Conjugation of a polypeptide to another peptide may further be achieved by genetic means through the use of recombinant DNA techniques that are well know in the art, such as those set forth in the teachings of Sambrook et al. Molecular Cloning: A Laboratory Manual, 2 ed. Vol. 1, pp. 1.101-104, Cold Spring Harbor Laboratory Press, (1989) and F.M. Ausubel et al. Current Protocols in Molecular Biology, Eds. J.Wiley Press (2006), the relevant portions of which are incorporated herein by reference.

A "variant" polypeptide of the invention can be a polypeptide which has an amino acid sequence which differs from the polypeptide encoded by SEQ ID NO 1, 2, 3, 4, 5, 6, 7, 8 or 9 due to the presence of one or more deletions, insertions, or substitutions of amino acid residues. In embodiments, a variant has at least 85%, 86%, 87%, 88%, 89%, preferably at least 90%, 91%, 92%, 93%, 94%, and more preferably 95%, 96%, 97%, 98%, 99% but less than 100% contiguous amino acid sequence identity to the corresponding polypeptide encoded by the nucleotide sequence as disclosed herein. Percentage identity may be determined using, for example computer programs as would be known by one skilled in the art.

Variants can include polypeptides in which individual amino acids of the polypeptide of the invention are substituted by other amino acids which are closely related as understood in the art, for example, substitution of one hydrophobic residue such as isoleucine, valine, leucine or methionine for another, or the substitution of one polar residue for another, such as arginine for lysine, glutamic for aspartic acid or glutamine for asparagine.

In embodiments, a fragment of a polypeptide of the present invention can consist of a truncated version of a polypeptide of the invention which has been truncated by 1, 2, 3, 4 or more than 5, more than 10, or more than 20 amino acids. An antigenic fragment may be generated using for example C-terminal deletion of any one of the polynucleotide sequences of the genes as listed in Table 1 or Table 2 and said C-terminal deletion constructs may then be inserted into a suitable prokaryotic or eukaryotic expression plasmid. The antigenic activity of the expression products derived from the constructs may then be tested by assessing reactivity with antisera from naturally and/or experimentally infected horse or foals using immunoblotting methods. Alternatively a series of synthetic polypeptide fragments with greater than 85%, greater than 90%, greater than 95%, or 100% sequence identity to portions of any one the polypeptides encoded by a polynucleotide sequence of a gene of Table 1 or more preferably Table 2 can be generated. These peptides may then be reacted with antisera from naturally or experimentally infected horses using an ELISA method to determine which peptide fragments are antigenic. Alternatively, synthetic peptides may be used to immunise, for example, mice, rabbits, or horses and the antisera produced can be assessed for reactivity with R. equi using indirect immunofluorescence assays. In this way immunogenic fragments may be identified and R. equi-specific antisera may be produced. These two latter approaches described are particularly advantageous for small peptides that contain linear, continuous epitopes.

"Operably linked" means that a nucleic acid molecule is placed in functional relationship with another nucleic acid molecule. Generally an operably linked promoter will be linked such that it is contiguous with and in the same reading phase as the gene to be expressed.

Generally the terms "treating", "treatment" and the like are used to mean affecting a subject tissue or cell to obtain a desired pharmacological and/or physiological effect. As used herein, the term "treatment" and associated terms such as "treat" and "treating" means the reduction of the progression, severity and/or duration of infection or for the amelioration of at least one of the symptoms thereof by R. equi or may be prophylactic (preventative treatment). The term 'treatment' therefore refers to any regimen that can benefit a subject. References herein to "therapeutic" and "prophylactic" treatments are to be considered in their broadest context. The term "therapeutic" does not necessarily imply that a subject is treated until total recovery. Similarly, "prophylactic" does not necessarily mean that the subject will not eventually contract a disease condition.

As used herein, the term "subject" refers to an animal, preferably a mammal and in particular a horse.

FIGURES

Embodiments of the present invention will now be described by way of example only with reference to the accompanying figures in which:

FIG. 1 illustrates the R. equi pilus locus (rpl). (A) The 9 Kb rpl horizontally acquired (HGT) island (REQ18350-430) is absent from nonpathogenic Rhodococcus spp. (e.g. R. jostii RHA1 and R. erythropolis PR4). rpl genes have were detected in all R. equi clinical isolates (≈300 isolates tested). rpl gene products which are considered to be encoded are: A, prepilin peptidase; B, pilin subunit; C, TadE minor pilin; D, putative lipoprotein; E, CpaB pilus assembly protein; F, CpaE pilus assembly protein; GHI, Tad transport machinery. (B) Electron micrograph of R. equi 103S pili (indicated by arrowheads). Bar=0.5 µm. (C) R. equi pili visualized by immunofluorescence microscopy (×1,000 magnification). Reproduced from Letek et al. 2010, PLoS Genet. 6: e1001145).

FIG. 2 illustrates a demonstration by targeted mutant construction and genetic re-complementation analysis that the rpl locus encodes the R. equi pilus. Negative staining transmission electron micrographs of wild-type R. equi 103S (WT) (panel A), isogenic rplB deletion mutant of 103S (ΔrplB, apiliated) (panel B), rplB-complemented mutant (piliated) (panel C), and mock-complemented mutant with an empty vector (no rplB gene). Bar=0.5 µm (panel D).

Figure 5:
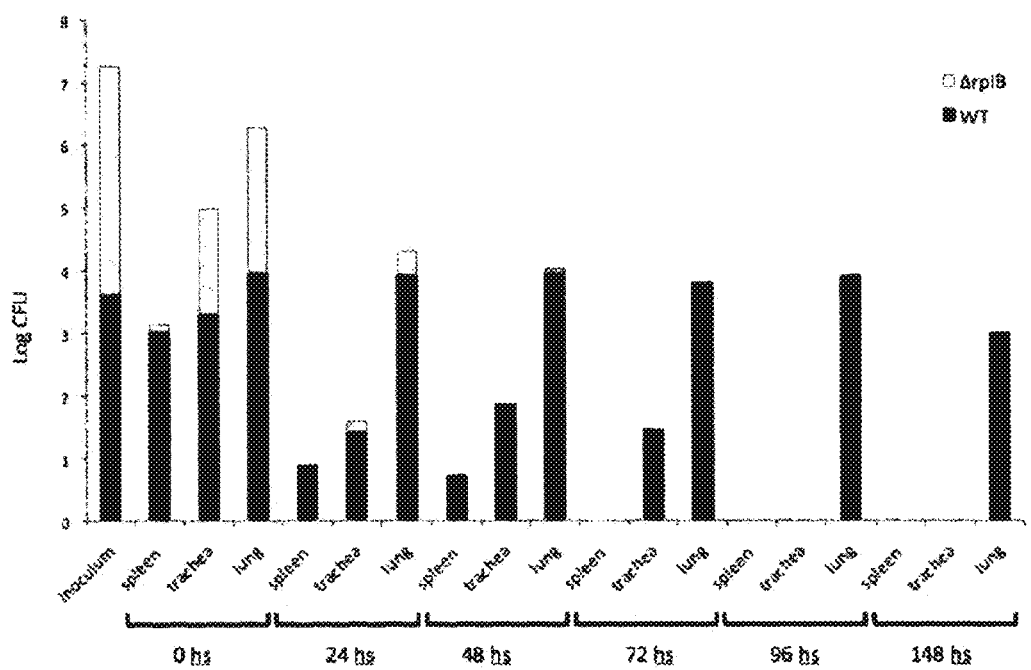

FIG. 5 illustrates Rpl pili are essential for R. equi lung colonization in mice as demonstrated using a novel in vivo lung infection model in mice developed by the inventors. It is based on a competitive virulence assay in which each mouse receives an intranasal inoculum containing 50% of wild-type (WT) R. equi bacteria and 50% of mutant (ΔrplB) R. equi bacteria. t=0 means 60 min after delivery of the intranasal inoculum.

Figure 6:
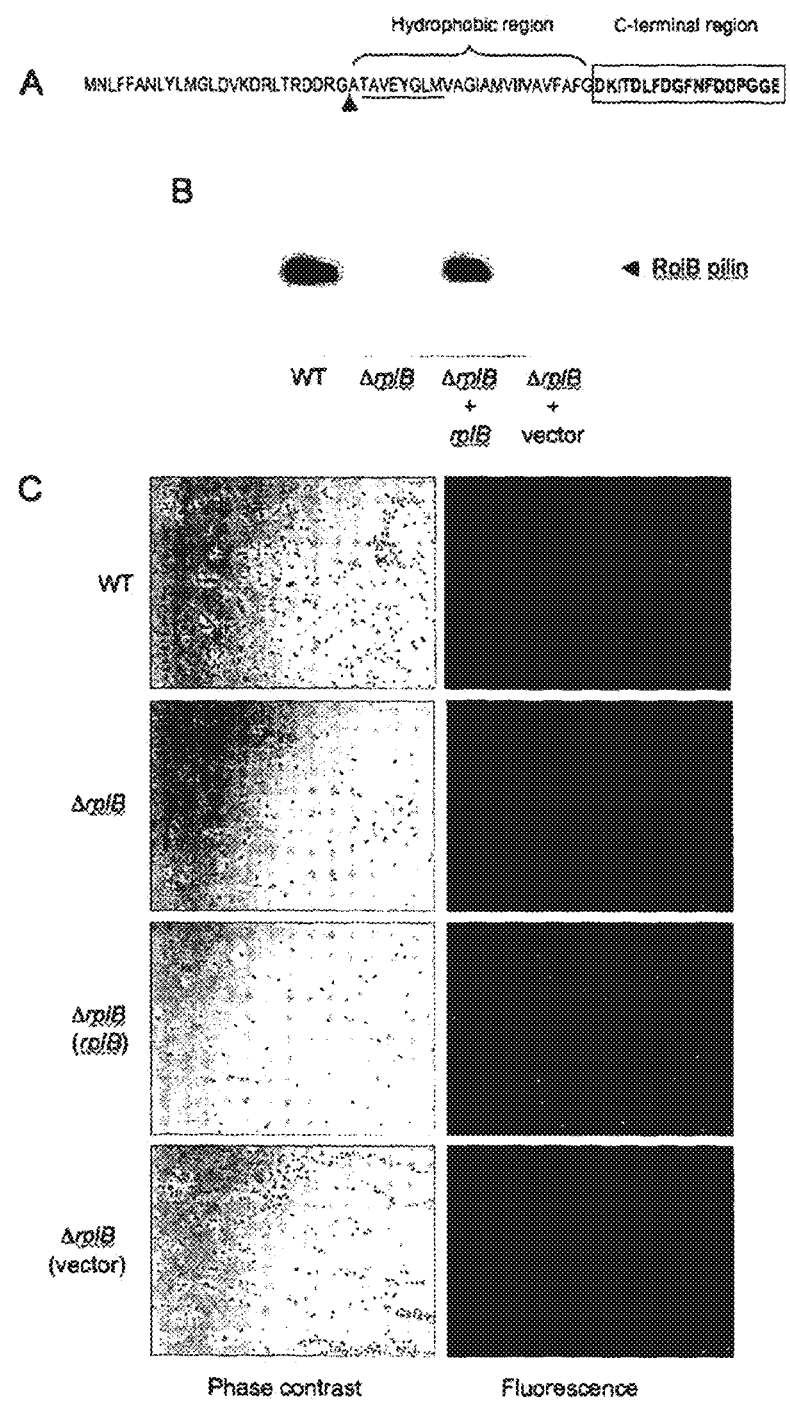

FIG. 6 illustrates production in rabbits of a specific antibody against the putative R. equi pilin subunit (RplB). (A) Amino acid sequence of putative RplB prepilin and of the C-terminal peptide used to raise a rabbit polyclonal antibody (boxed). Arrowhead indicates putative cleavage site of the prepilin. (B) Immunodetection of the RplB pilin by SDS-PAGE western blot analysis of whole cell extracts of wild-type R. equi (WT), an isogenic in-frame deletion rplB mutant (ΔrplB), the rplB-complemented mutant (ΔrplB+rplB), and a mock-complement mutant (ΔrplB+vector), using the anti-RplB peptide antibody (diluted 1:1,000; secondary antibody, alkaline phosphatase-conjugated mouse anti-rabbit monoclonal antibody, 1:10,000 diluted; reaction revealed with NBT/BCIP substrate. The anti-Rpl antibody specifically detects the Rpl pilin subunit in WT and re-completed rpl mutant, not in the apiliated rpl mutant and mock-complemented mutant. (C) Detection of Rpl pili production in *R. equi* by immunofluorescence using the anti-RplB peptide antibody and the same bacteria as in (B) (630× magnification, Leica AF6000 microscope).

Figure 7:
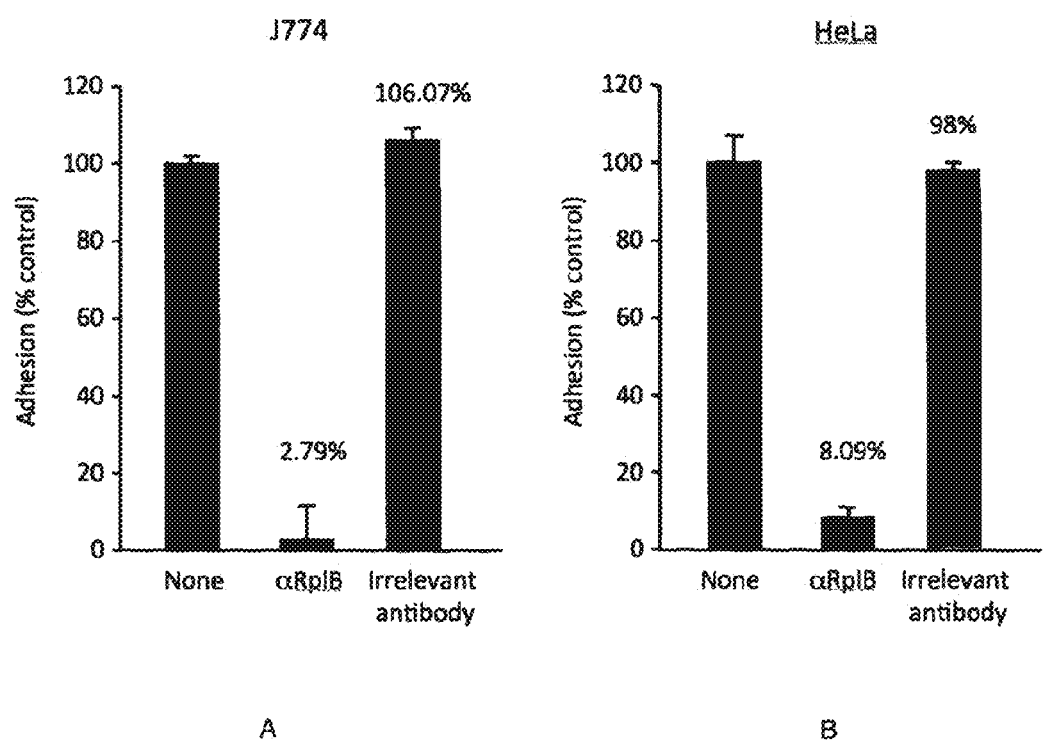

FIG. 7 illustrates Inhibition of *R. equi* attachment to (A) macrophages and (B) epithelial cells by an anti-RplB antibody. Prior to the adhesion assay, the antibody raised against the RplB (pilin subunit) peptide (see FIG. 6A) was incubated for 60 min at 37° C. (40 μl/ml of a suspension in cell culture medium of exponentially grown R. equi bacteria at a density calculated for a multiplicity of infection of 15:1). As a control, the *R. equi* bacterial cell suspension was pre-incubated with an irrelevant antiserum (anti-Listeria monocytogenes rabbit polyclonal antibody).

Figure 8:
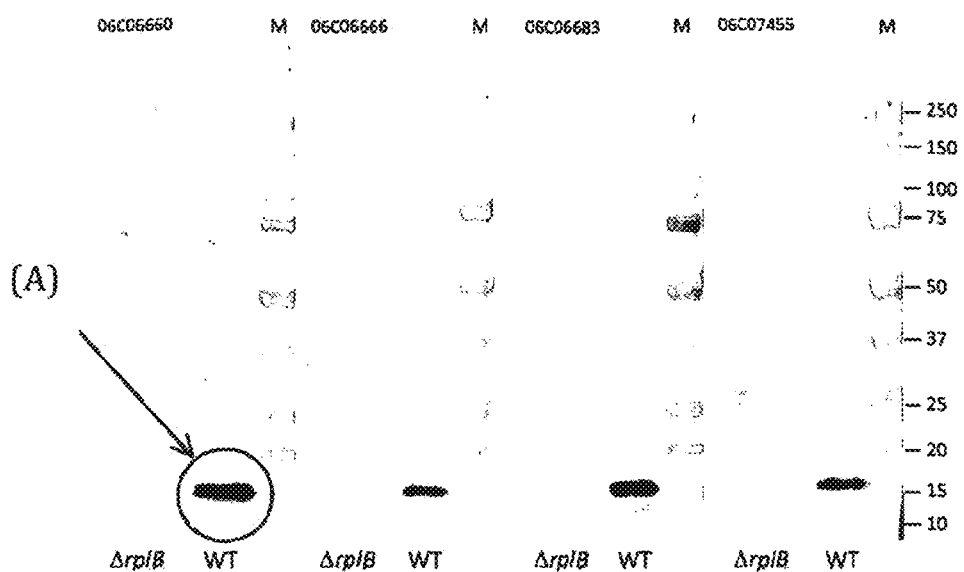

FIG. 8 illustrates RplB pilin antigens are recognized in vivo and elicit a strong antibody response in naturally infected foals. Representative example of the reactivity against the Rpl pilin of horse sera from bacteriologically confirmed cases of foal pneumonia, as determined by SDS-PAGE western blot analysis with whole cell extracts of wild-type *R. equi* (WT) and the isogenic ΔrplB mutant. All convalescent sera tested to date gave a strong reaction against the RplB pilin antigen whereas normal (non-case) sera did not. The Rpl pili dissociate into 18 kDa polypeptides that probably correspond to SDS-resistant homo-tetramers (predicted molecular mass of RplB pilin, 4.95 kDa) that remain non-covalently bound by strong monomer-monomer interactions via the N-terminal hydrophobic region of the pilin subunit. (A) indicates RplB is the first antigen detected in a curde *R. equi* protein preparation by the antibodies present in case sera.

Figure 9:
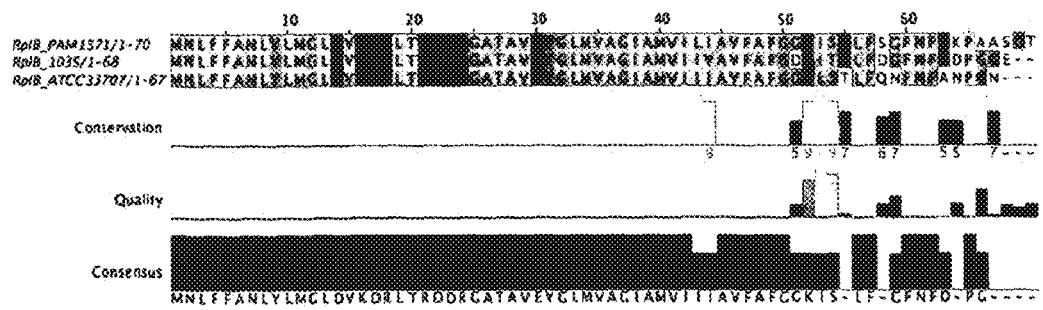
Figure 9A:
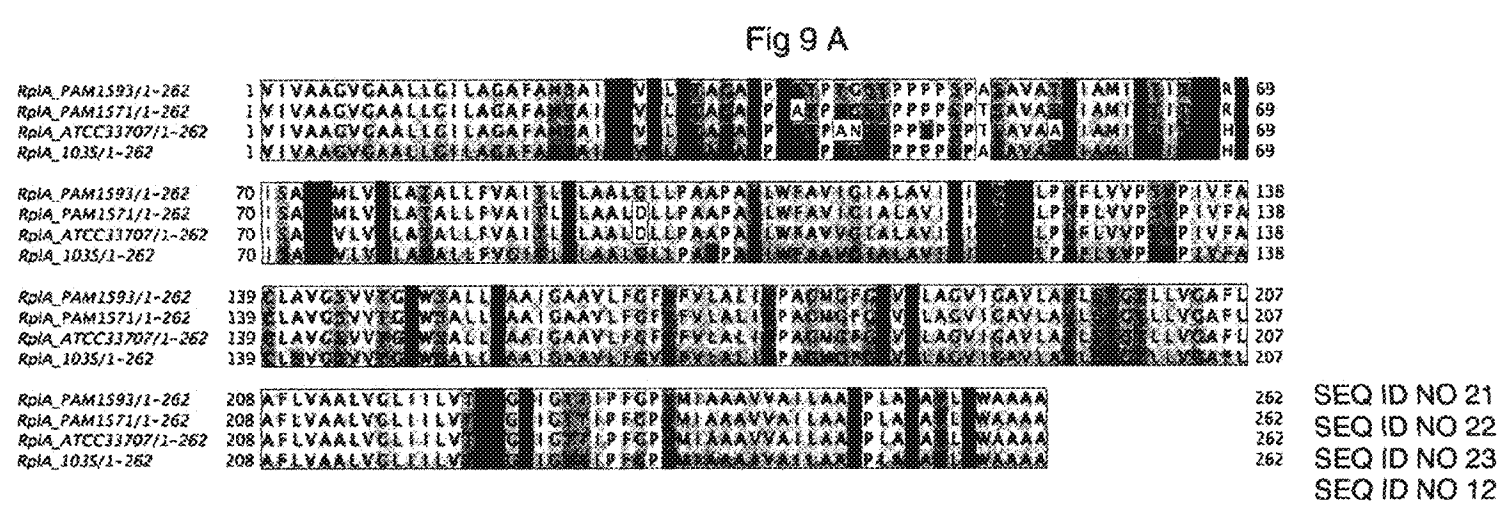
Figure 9B:
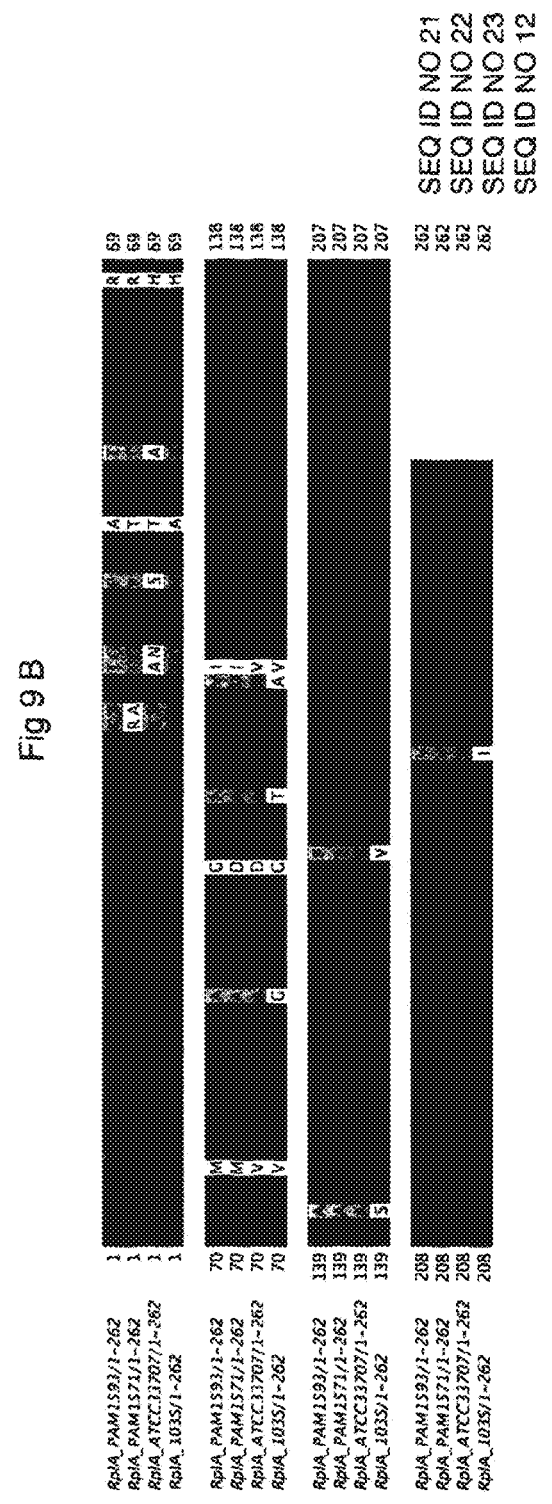
Figure 9C:
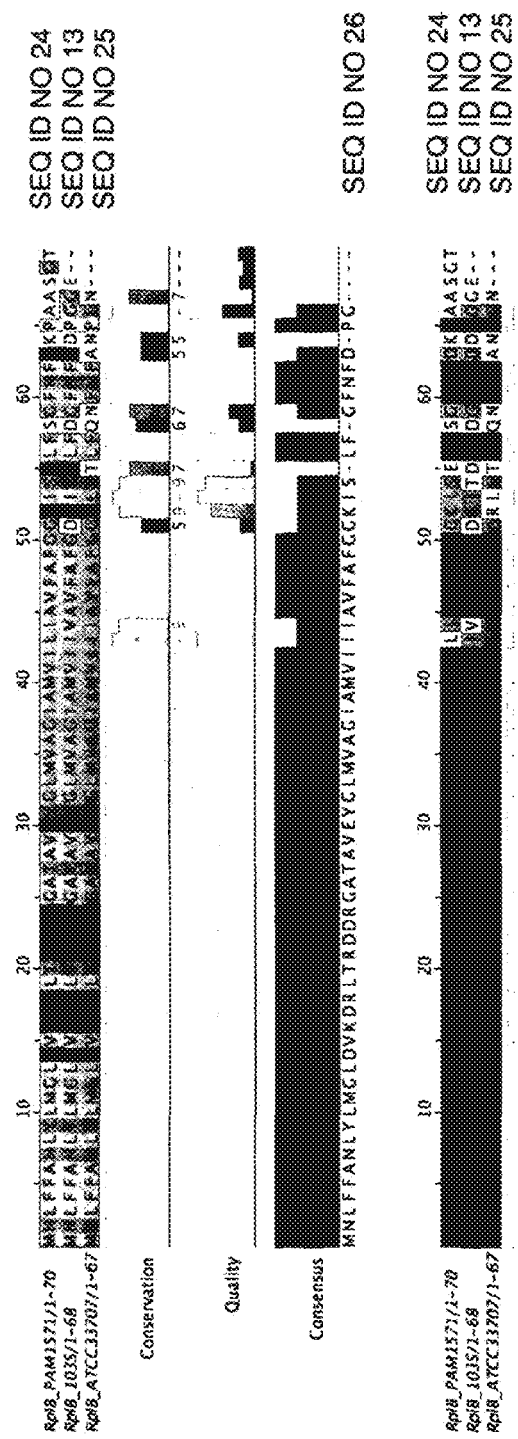
Figure 9D:
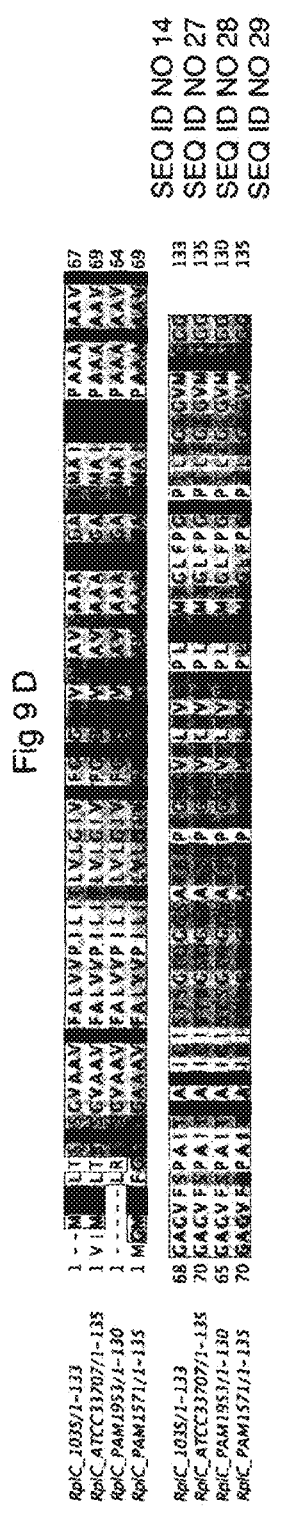
Figure 9E:
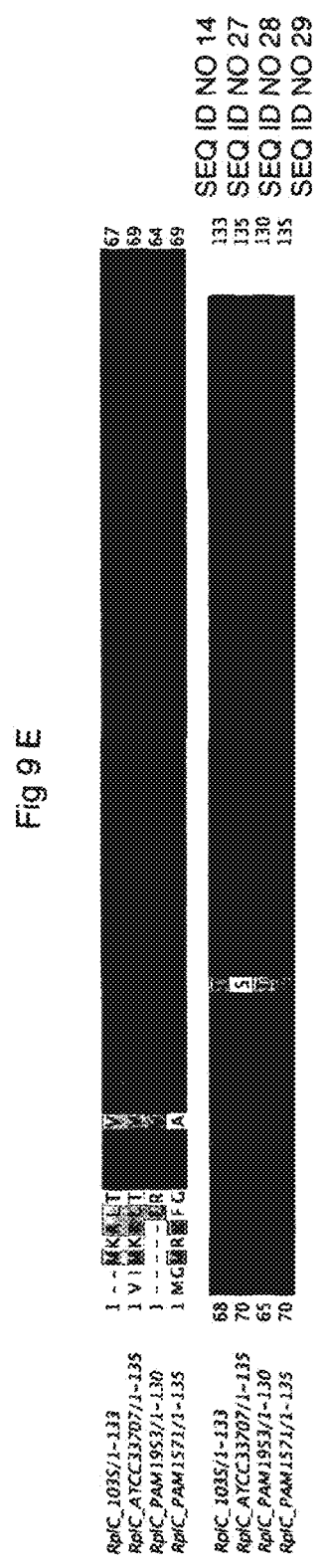
Figure 9F:
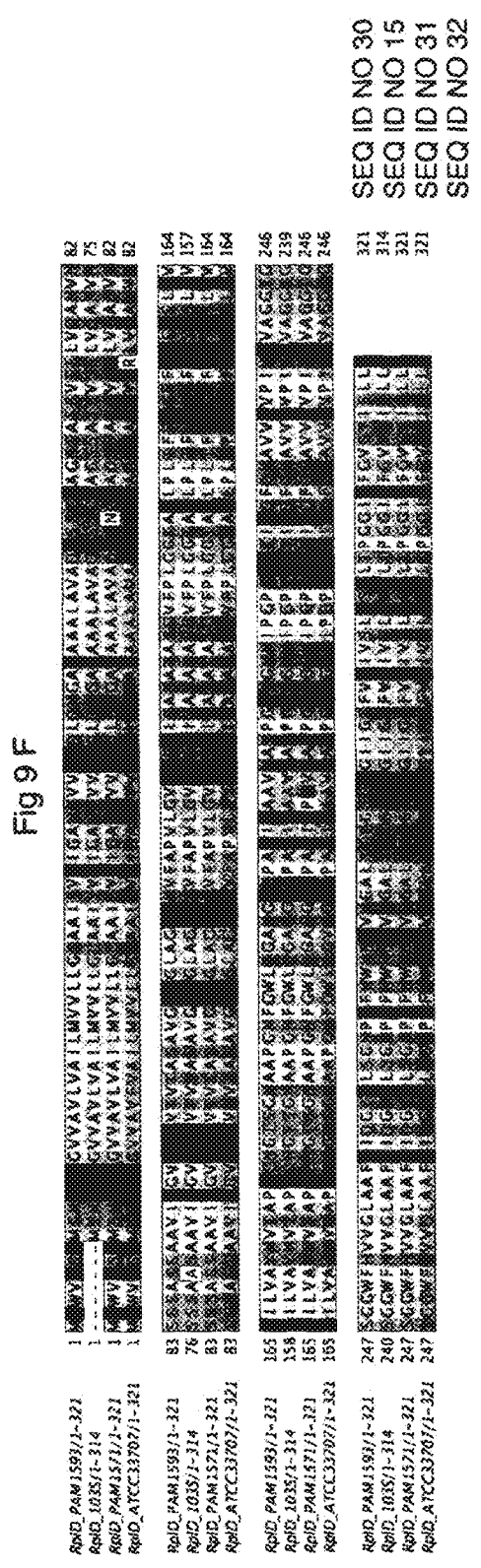
Figures 9G, 9H:
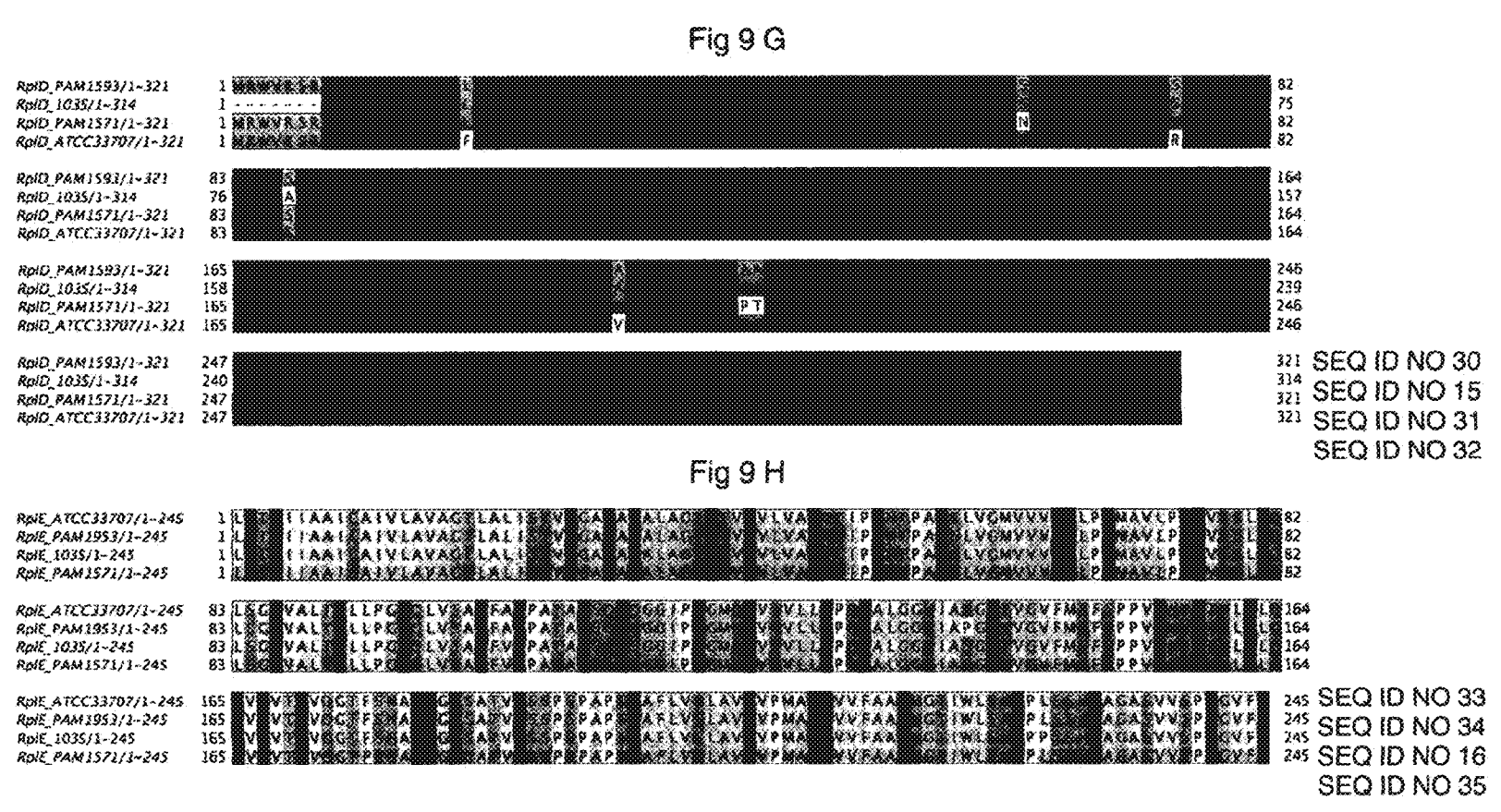
Figure 9K:
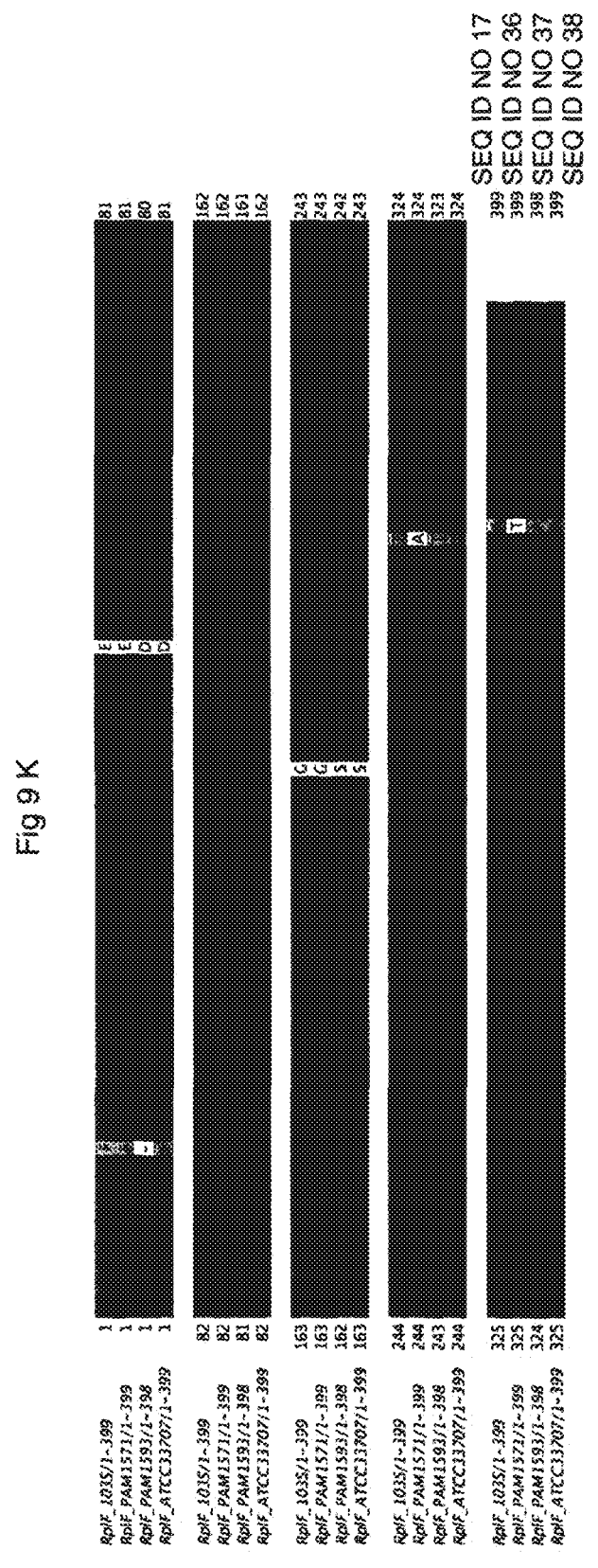
Figure 9L:
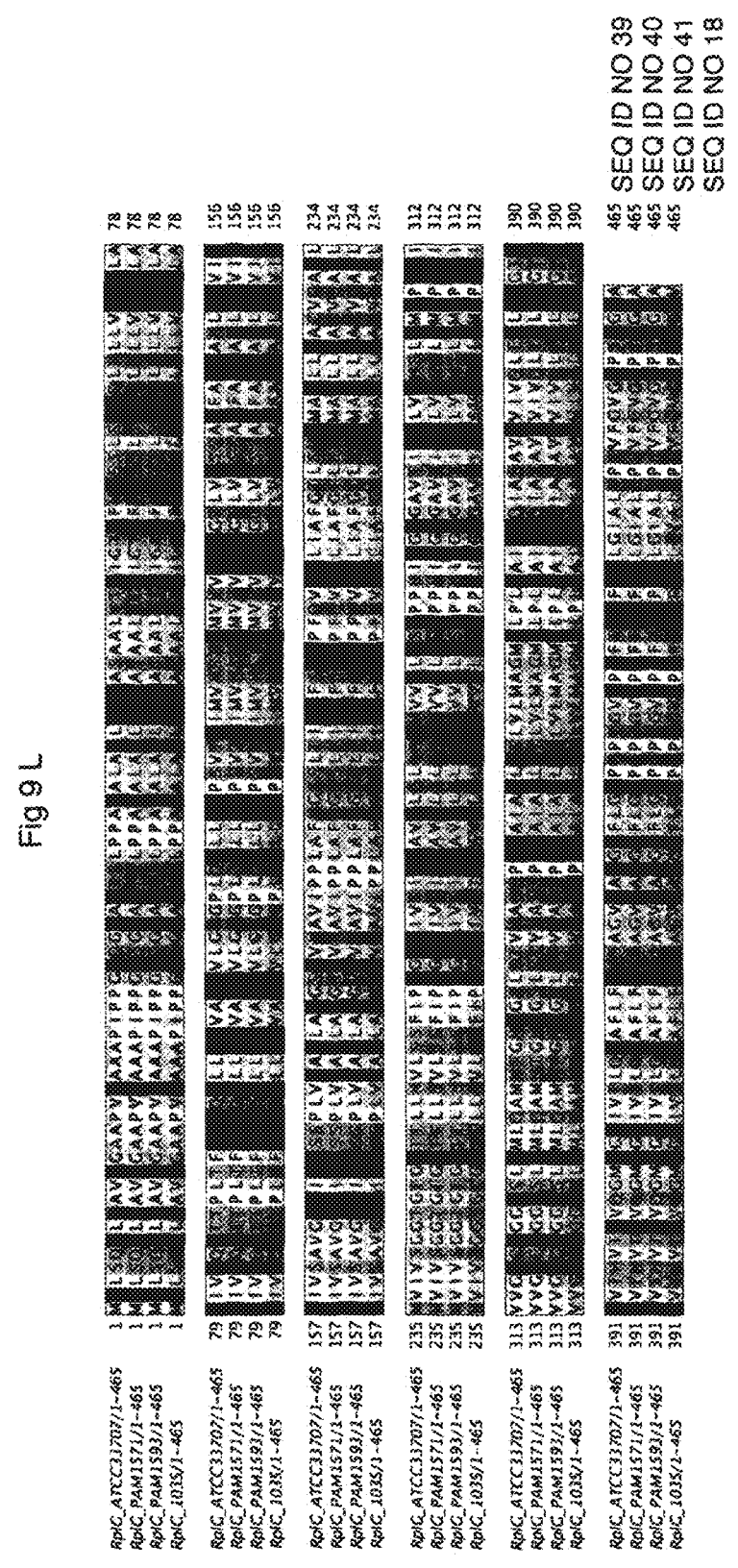
Figure 9N:
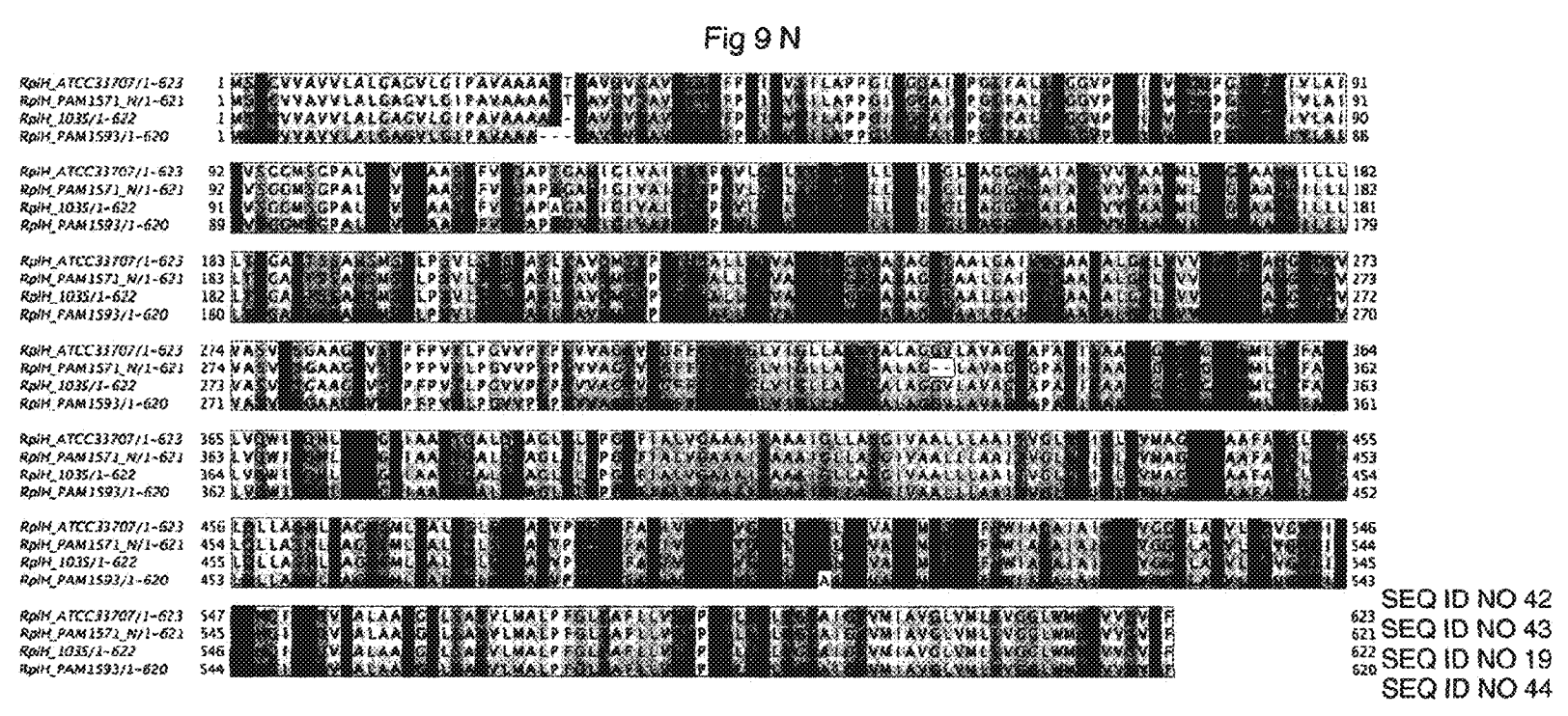
Figure 9O:
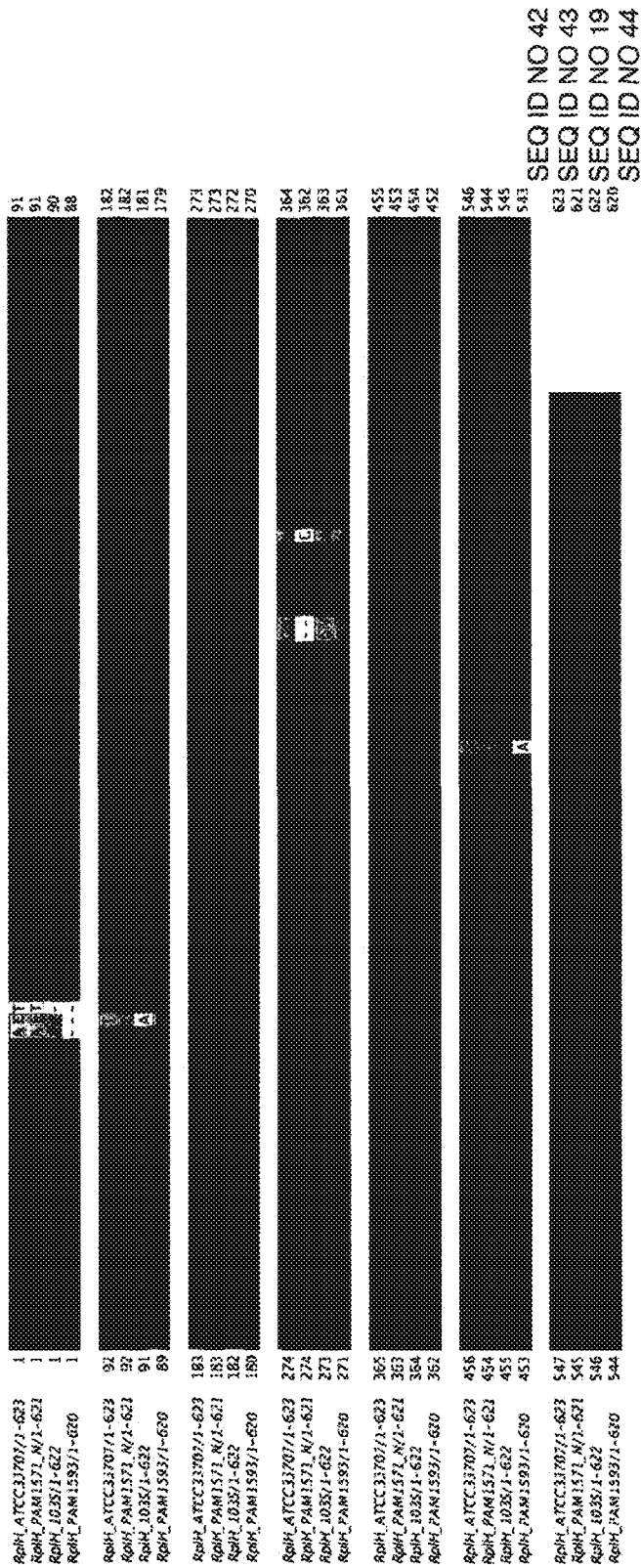
Figures 9P, 9Q:
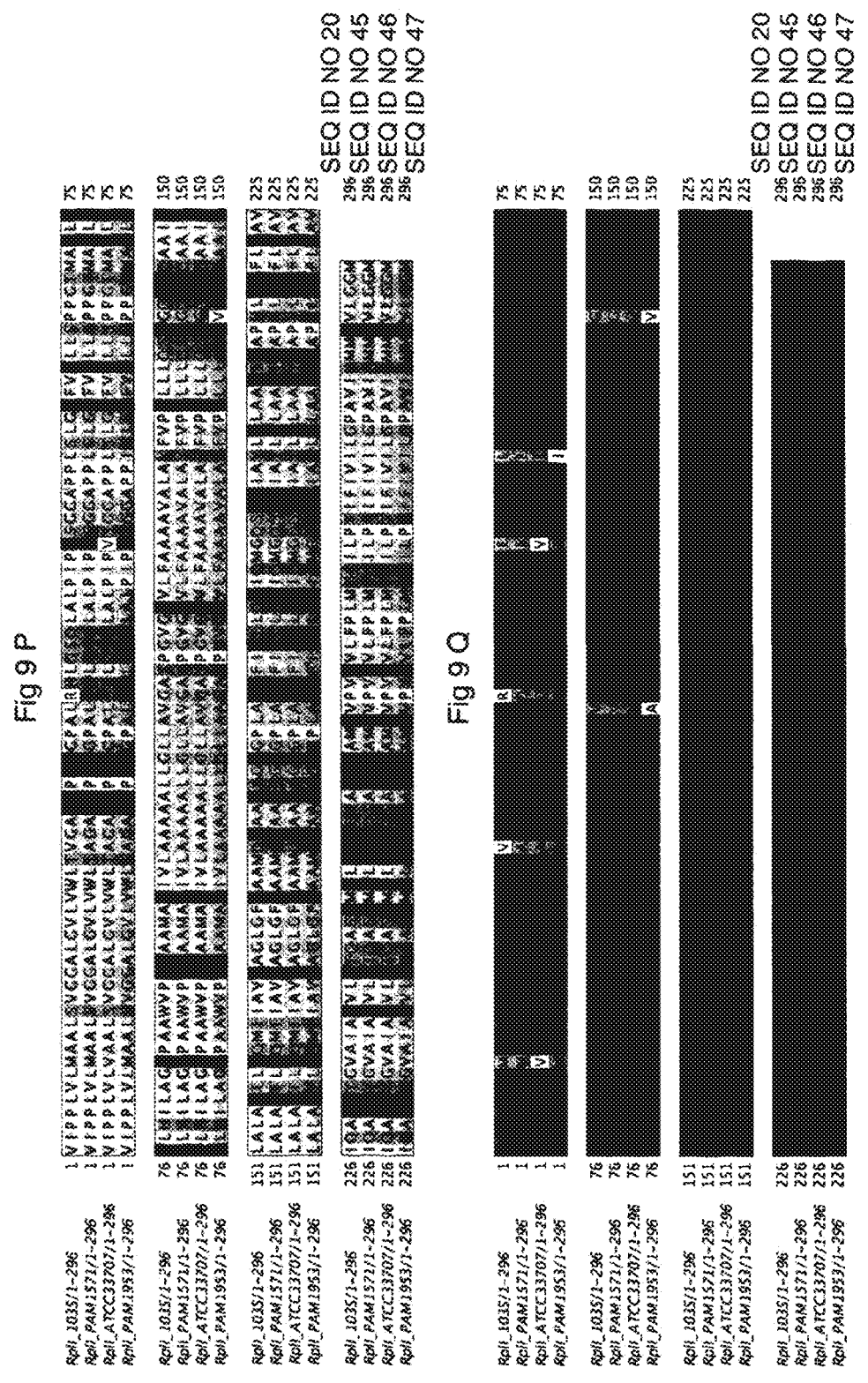

FIG. 9 illustrates variability of RplB amino acid sequence in *R. equi* strains and of other Rpl proteins.

FIG. 10 illustrates the nucleotide sequences encoding Rpl proteins of other strains of *R. equi*.

DETAILED DESCRIPTION OF THE INVENTION

As indicated above, the inventors have identified polypeptides which play an important role in virulence of *R equi* and have used this knowledge to identify polypeptides which can be used to mediate an immune response in infected subjects, particularly horses, and in particular foals. Whilst the amino acid sequences of the polypeptides determined for the identified strain are noted, as will be understood, biologically active immunogenic fragments, derivatives or variants of such a polypeptide can also be used. As discussed variant polypeptides can comprise amino acid percent identity with the amino acid sequences disclosed herein. Alternatively, polypeptides of the invention may be encoded by variant nucleic acid sequences which have nucleotide percent identity with the polynucleotide sequences disclosed herein.

The percent identity of two or more sequences may be determined by visual inspection and mathematical calculation. Alternatively, the percent identity of two nucleic acid sequences can be determined by comparing sequence information using the GAP computer program, version 6.0 described by Devereux et al. (Nucl. Acids Res. 12:387, 1984) and available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of Gribskov and Burgess, Nucl. Acids Res. 14:6745, 1986, as described by Schwartz and Dayhoff, eds., Atlas of Protein Sequence and Structure, National Biomedical Research Foundation, pp. 353-358, 1979; (2) a penalty of 3.0 for each gap and an additional 0.10 penalty for each symbol in each gap; and (3) no penalty for end gaps. Other programs used by one skilled in the art of sequence comparison may also be used.

Polypeptides of the invention may be prepared by any of a number of conventional techniques. A nucleic acid encoding a peptide or a biologically active immunogenic fragment, derivative, or variant thereof, may be subcloned into an expression vector for production of the polypeptide or fragment. The DNA sequence advantageously is fused to a sequence encoding a suitable leader or signal peptide and/or a promoter operable in a cell into which the nucleic acid is to be introduced. Alternatively, the desired fragment may be chemically synthesized using known techniques. DNA fragments also may be produced by restriction endonuclease digestion of a full length cloned DNA sequence, and isolated by electrophoresis on agarose gels. If necessary, oligonucleotides that reconstruct the 5' or 3' terminus to a desired point may be ligated to a DNA fragment generated by restriction enzyme digestion. Such oligonucleotides may additionally contain a restriction endonuclease cleavage site upstream of the desired coding sequence, and position an initiation codon (ATG) at the N-terminus of the coding sequence.

Polymerase chain reaction (PCR) procedure also may be employed to isolate and amplify a DNA sequence encoding a desired polypeptide fragment. Oligonucleotides that define the desired termini of the DNA fragment are employed as 5' and 3' primers. The oligonucleotides may additionally contain recognition sites for restriction endonucleases, to facilitate insertion of the amplified DNA fragment into an expression vector. PCR techniques are described in Saiki et al., Science 239:487 (1988); Recombinant DNA Methodology, Wu et al., eds., Academic Press, Inc., San Diego (1989), pp. 189-196; and PCR Protocols: A Guide to Methods and Applications, Innis et al., eds., Academic Press, Inc. (1990).

The invention encompasses polypeptides and biologically active immunogenic fragments, derivatives, or variants thereof in various forms, including those that are naturally occurring or produced through various techniques such as procedures involving recombinant DNA technology. For example, nucleotides encoding polypeptides of the invention can be derived from SEQ ID NO 1, 2, 3, 4, 5, 6, 7, 8, or 9 by in vitro mutagenesis, which includes site-directed mutagenesis, random mutagenesis, and in vitro nucleic acid synthesis. Such forms include, but are not limited to, derivatives, variants, and oligomers, as well as fusion proteins or fragments thereof.

Polypeptide Derivatives

Embodiments of a derivative of a polypeptide of the invention can comprise one or more non-naturally occurring amino acids or amino acid analogs, including non-genetically encoded L-amino acids, synthetic L-amino acids or D-enantiomers of an amino acid. Suitably, embodiments of a derivative can comprise one or more residues selected from the group consisting of: hydroxyproline, β-alanine, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylananine 3-benzothienyl alanine 4-chlorophenylalanine, 2-fluorophenylalanine, 3-fluorophenylalanine, 4-fluorophenylalanine, penicillamine, 1,2,3,4-tetrahydrotic isoquinoline-3-carboxylic acid β-2-thienylalanine, methionine sulfoxide, homoarginine, N-acetyl lysine, 2,4-diamino butyric acid, p-aminophenylalanine, N-methylvaline, homocysteine, homoserine, ε-amino hexanoic acid, δ-amino valeric acid, 2,3-diaminobutyric acid and mixtures thereof. Other amino acid residues that are useful for making the polypeptides and polypeptide derivatives described herein can be found, e.g., in Fasman, 1989, CRC Practical Handbook of Biochemistry and Molecular Biology, CRC Press, Inc., and the references cited therein.

In embodiments, derivatives of polypeptides of the invention can also comprise an isostere of a polypeptide. The term "isostere" as used herein is intended to include a chemical structure that can be substituted for a second chemical structure because the steric conformation of the first structure fits a binding site specific for the second structure. The term specifically includes peptide back-bone modifications (i.e., amide bond mimetics) known to those skilled in the art. Such modifications include modifications of the amide nitrogen, the α-carbon, amide carbonyl, complete replacement of the amide bond, extensions, deletions or backbone crosslinks. Several peptide backbone modifications are known, including ψ[CH2S], ψ[CH2NH], ψ[CSNH2], ψ[NHCO], ψ[COCH2], and ψ[(E) or (Z) CH=CH]. In the nomenclature used above, ψ indicates the absence of an amide bond. The structure that replaces the amide group is specified within the brackets. Other modifications include, for example, an N-alkyl (or aryl) substitution (ψ[CONR]), or backbone crosslinking to construct lactams and other cyclic structures. In another example, a polypeptide derivative may be a retro-peptide analog. A retro-peptide analog comprises a reversed amino acid sequence of a polypeptide described herein. For example, a retro-peptide analog of a polypeptide comprises a reversed amino acid sequence of a sequence set forth in any one of SEQ ID NO 10, 11, 12, 13, 14, 15, 16, 17, 18, 19, or 20. Retro-inverso polypeptides may be complete or partial. Complete retro-inverso peptides are those in which a complete sequence of a polypeptide described herein is reversed and the chirality of each amino acid in a sequence is inverted, other than glycine, because glycine does not have a chiral analog. Partial retro-inverso polypeptides are those in which only some of the peptide bonds are reversed and the chirality of only those amino acid residues in the reversed portion is inverted. For example, one or two or three or four or five or more than 10, more than 20, more than 30, more than 40 or more than 50 amino acid residues are D-amino acids. Suitably a polypeptide of and for use in the present invention may be further modified using at least one of C and/or N-terminal capping, and/or cysteine residue capping. Suitably, a polypeptide of and for use in the present invention may be capped at the N terminal residue with an acetyl group. Suitably, a polypeptide of and for use in the present invention may be capped at the C terminal with an amide group. Suitably, thiol groups of cysteines of polypeptides of the invention may be capped with acetamido methyl groups. In embodiments, the term derivative can include scrambled polypeptides comprising immunodominant epitopes of the rpl encoded pilus for example fragments of SEQ ID NOs 10, 11, 12, 13, 14, 15, 16, 17, 18, 19 or 20. In embodiments derivatives can be encoded by rpl genes or fragments thereof which encode immunodominant epitopes of Rpl pilus provided in tandem, or as longer repeat stretches, for example concatemerized, to increase the immunogenicity of the encoded polypeptides. In embodiments, combinations of polypeptides of the invention (and corresponding nucleic acid sequences) can be fused in a single polypeptide.

Polypeptide Synthesis

A polypeptide or a biologically active immunogenic fragment, derivative, or variant thereof may be synthesized using any suitable chemical method known to the person skilled in the art. For example, synthetic peptides can be prepared using known techniques of solid phase, liquid phase, or peptide condensation, or any combination thereof, and can include natural and/or unnatural amino acids. Amino acids used for peptide synthesis may be standard Boc (Nα-amino protected Nα-t-butyloxycarbonyl) amino acid resin with the deprotecting, neutralization, coupling and wash protocols of the original solid phase procedure of Merrifield, J. Am. Chem. Soc., 85:2149-2154, 1963, or the base-labile Na-amino protected 9-fluorenylmethoxycarbonyl (Fmoc) amino acids described by Carpino and Han, J. Org. Chem., 37:3403-3409, 1972. Both Fmoc and Boc Nα-amino protected amino acids can be obtained from various commercial sources, such as, for example, Fluka, Bachem, Advanced Chemtech, Sigma, Cambridge Research Biochemical, Bachem, or Peninsula Labs.

Generally, chemical synthesis methods comprise the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do notracemize chiral centers) a protected tripeptide with a properly protected dipeptide to form, after deprotection, a pentapeptide. See, e.g., J. M. Stewart and J. D. Young, Solid Phase Peptide Synthesis (Pierce Chemical Co., Rockford, Ill. 1984) and G. Barany and R. B. Merrifield, The Peptides: Analysis, Synthesis, Biology, editors E. Gross and J. Meienhofer, Vol. 2, (Academic Press, New York, 1980), pp. 3-254, for solid phase peptide synthesis techniques; and M. Bodansky, Principles of Peptide Synthesis, (Springer-Verlag, Berlin 1984)and E. Gross and J. Meienhofer, Eds., The Peptides: Analysis. Synthesis. Biology, Vol. 1, for classical solution synthesis. Typical protecting groups include t-butyloxycarbonyl (Boc), 9-fluorenylmethoxycarbonyl (Fmoc) benzyloxycarbonyl (Cbz); p-toluenesulfonyl (Tx); 2,4-dinitrophenyl; benzyl (Bzl); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like.

Typical solid supports are cross-linked polymeric supports. These can include divinylbenzene cross-linked-styrene-based polymers, for example, divinylbenzene-hydroxymethylstyrene copolymers, divinylbenzene-chloromethylstyrene copolymers and divinylbenzene-benzhydrylaminopolystyrene copolymers.

A peptide or a biologically active immunogenic fragment, derivative, or variant thereof as described herein according to any embodiment can also be chemically prepared by other methods such as by the method of simultaneous multiple peptide synthesis. See, e. g., Houghten Proc. Natl. Acad. Sci. USA 82: 5131-5135, 1985 or U.S. Pat. No. 4,631,211.

Recombinant Polypeptide Production

Alternatively, or in addition, a peptide or a biologically active immunogenic fragment, derivative, or variant thereof can be produced as a recombinant protein. To facilitate the production of a recombinant polypeptide, nucleic acid encoding the same is preferably isolated or synthesized. Typically the nucleic acid encoding the recombinant protein is/are isolated using a known method, such as, for example, amplification (e.g., using PCR or splice overlap extension) or isolated from nucleic acid from *R. equi* using one or more restriction enzymes or isolated from a library of nucleic acids.

Methods for such isolation will be apparent to the ordinary skilled artisan and/or described in Ausubel et al (In: Current Protocols in Molecular Biology. Wiley Interscience, ISBN 047 150338, 1987), Sambrook et al (In: Molecular Cloning: Molecular Cloning: A Laboratory Manual, Cold Spring Harbor Laboratories, New York, Third Edition 2001).

For expressing protein by recombinant means, a protein-encoding nucleic acid is placed in operable connection with a promoter or other regulatory sequence capable of regulating expression in a cell-free system or cellular system. For example, nucleic acid comprising a sequence that encodes a polypeptide of the pili of *R. equi* is placed in operable connection with a suitable promoter and maintained in a suitable cell for a time and under conditions sufficient for expression to occur.

A number of other gene construct systems for expressing a nucleic acid of a gene selected from Table 1 or Table 2 in bacterial cells are well-known in the art and are described for example, in Ausubel et al (In: Current Protocols in Molecular Biology. Wiley Interscience, ISBN 047 150338, 1987), and Sambrook et al (In: Molecular Cloning: Molecular Cloning: A Laboratory Manual, Cold Spring Harbor Laboratories, New York, Third Edition 2001).

A wide range of additional host/vector systems suitable for expressing a polypeptide of the present invention are available publicly, and described, for example, in Sambrook et al (In: Molecular cloning, A laboratory manual, second edition, Cold Spring Harbor Laboratory, Cold Spring Harbor, N.Y., 1989).

Following expression of a polypeptide, isolation and purification of the polypeptide may be accomplished by any suitable technique, as would be known in the art.

Compositions

A polypeptide or a biologically active immunogenic fragment, derivative, or variant thereof may be administered alone, but will preferably be administered as a pharmaceutical composition, which will generally comprise a suitable pharmaceutically acceptable excipient, diluent or carrier selected depending on the intended route of administration. Examples of suitable pharmaceutical carriers include; water, glycerol and ethanol.

The term "carrier or excipient" as used herein, refers to a carrier or excipient that is conventionally used in the art to facilitate the storage, administration, and/or the biological activity of an active compound. A carrier may also reduce any undesirable side effects of the active compound. A suitable carrier is, for example, stable, e.g., incapable of reacting with other ingredients in the formulation. In one example, the carrier does not produce significant local or systemic adverse effect in recipients at the dosages and concentrations employed for treatment. Such carriers and excipients are generally known in the art. Suitable carriers for this invention include those conventionally used, e.g., water, saline, aqueous dextrose, and glycols are preferred liquid carriers, particularly (when isotonic) for solutions. Suitable pharmaceutical carriers and excipients include starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like.

Pharmaceutical composition adapted for oral administration may be presented as discrete units such as capsules, soft gels, or tablets; powders or granules; solutions or suspensions in aqueous or non-aqueous liquids; edible foams or whips; or oil-in-water liquid emulsions or water-in-oil liquid emulsions.

Pharmaceutical compositions provided as formulations adapted for parenteral administration include aqueous and non-aqueous sterile injection solutions which contain a polypeptide or a biologically active immunogenic fragment, derivative, or variant thereof or a antibody of the invention and optionally, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Administration

As will be appreciated by a person of skill in the art, selecting an administration regimen for a therapeutic composition or vaccine of the invention depends on several factors, including the serum or tissue turnover rate of a polypeptide of the invention or an antibody invention, the level of symptoms, the immunogenicity of the polypeptide, and the accessibility of the target cells in the biological matrix. Preferably, an administration regimen maximizes the amount of therapeutic compound delivered to the subject consistent with an acceptable level of side effects. Accordingly, the amount of polypeptide, antibody or composition delivered depends in part on the polypeptide, antibody or composition and the severity of the condition being treated.

A polypeptide or antibody can be provided, for example, by continuous infusion, or by doses at intervals of, e.g., one day, one week, or 1-7 times per week. A preferred dose protocol is one involving the maximal dose or dose frequency that avoids significant undesirable side effects. A total weekly dose depends on the type and activity of the compound being used. Determination of the appropriate dose is made by a veterinarian or clinician, for example using parameters or factors known or suspected in the art to affect treatment or predicted to affect treatment.

EXAMPLES

Example 1

Figure 1:
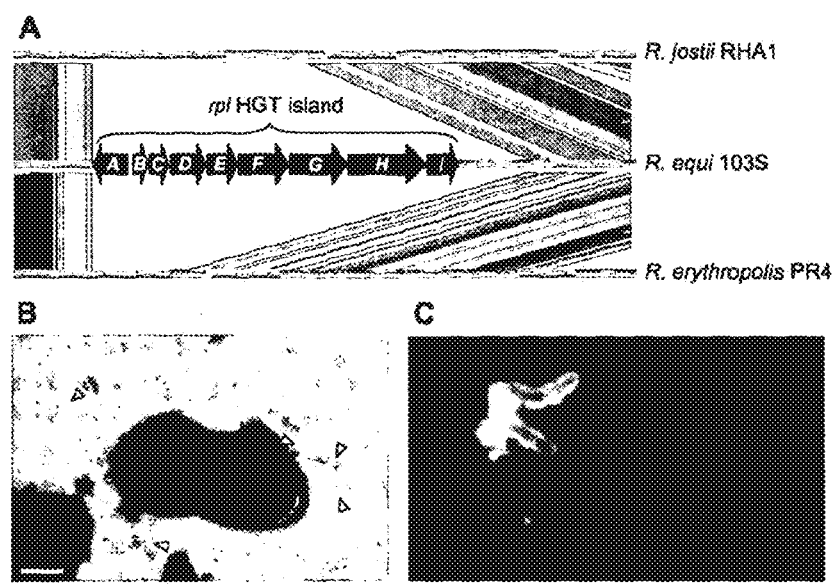

Using electron microscopy and other microscopical techniques we demonstrated that *R. equi* produces long, thick and apparently rigid pili appendages, typically between two and four per bacteria cell (FIG. 1 panels BC).

Example 2

Genome Sequencing

Genome sequencing of the complete genome sequence of *R. equi* strain 103S was determined in an international collaborative venture. The genome has just over 5 million base pairs and encodes 4598 genes of average length value 1009 pairs of nucleotides.

Example 3

Demonstration that the rpl (*R. equi* pili) locus (nucleotide positions 1,938,280 to 1,947,152, locus tags REQ18350-430)

encodes the *R. equi* pilus by targeted mutant construction and genetic re-complementation analysis.

Figure 2:
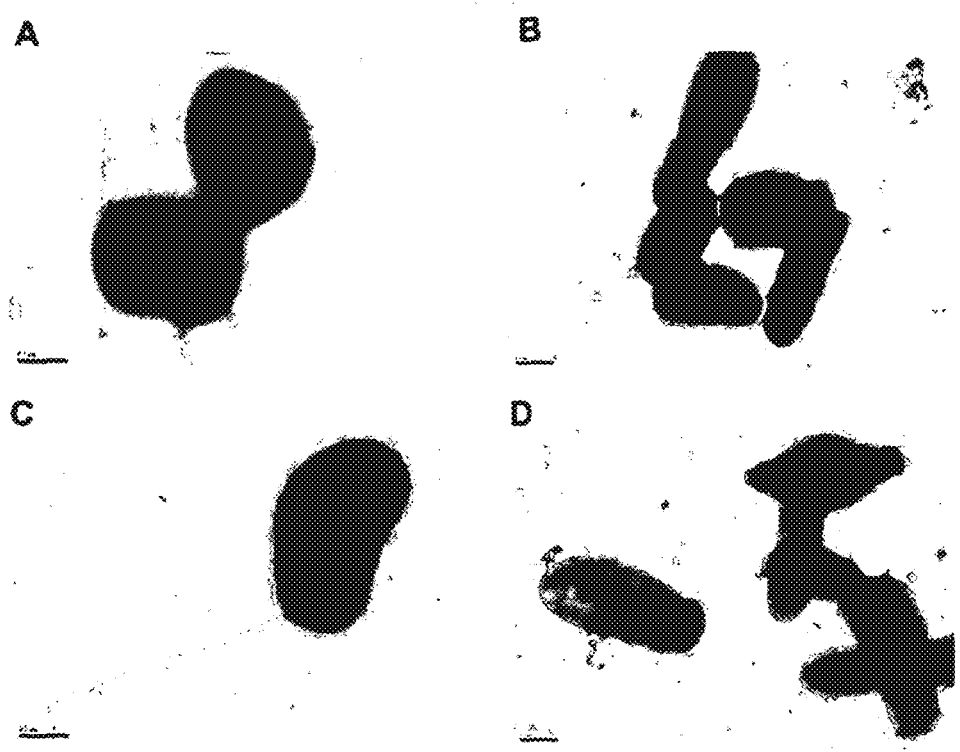

An in-frame deletion mutant was constructed in the rplB gene putatively encoding the Rpl pilin subunit (RplB). Homologous recombination methodology previously devised (Navas et al. 2001, Identification and mutagenesis by allelic exchange of choE, encoding a cholesterol oxidase from the intracellular pathogen *Rhodococcus equi*. J. Bacteriol. 183: 4796-4805), and a novel suicide vector, pSelAct, for positive selection of double recombinants on 5-fluorocytosine (5-FC) (van der Geize et al. 2008, A novel method to generate unmarked gene deletions in the intracellular pathogen *Rhodococcus equi* using 5-fluorocytosine conditional lethality. Nucleic Acids Res. 36: e1 51) was used in this approach. The ΔrplB mutant was complemented by stably inserting the rplB gene plus corresponding promoter region into the *R. equi* chromosome using the integrative vector pSET152 (Hong and Hondalus 2008, Site-specific integration of *Streptomyces* PhiC31 integrase-based vectors in the chromosome of *Rhodococcus equi*. FEMS Microbiol. Lett. 287: 63-68). As shown in FIG. 2, the inactivation of the rplB gene results in loss of pili formation by *R. equi*. Pili formation is restored upon reintroduction of the rplB gene in the ΔrplB mutant but not by complementation with an empty vector, demonstrating that rplB is a gene directly responsible for the piliated phenotype.

Example 4

Demonstration that the *R. equi* pili mediate attachment to mammalian cells.

Figure 3:
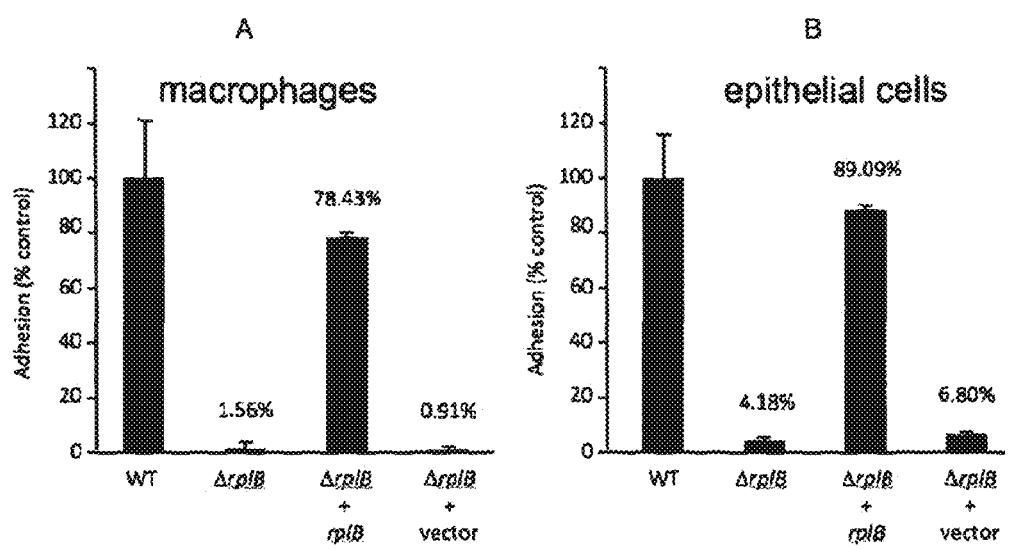
FIG. 3 illustrates the effect of rplB gene deletion and complementation on R. equi adhesion to (A) macrophages (J774A.1 cell line) and (B) epithelial cells (HeLa cell line), two key target cell types in the pathogenesis of airborne lung infection. Data expressed as percentage of the control (WT); mean of at least three independent duplicate experiments±SEM.

The ΔrplB mutant was tested in adhesion assays using monolayers of two cell types relevant to *R. equi* infection: epithelial cells to which the pathogen have to adhere to during the initial stages of lung colonization, and macrophages, which are used as host cells for bacterial intracellular replication. The rplB mutant was severely impaired in attachment to both eukaryotic cell types, and its complementation with the rplB gene but not an empty vector restored wild-type cytoadhesiveness (FIG. 3).

Two additional mutants were constructed in rplA and rplE (FIG. 1A) and they also caused a significant reduction of *R. equi* cytoadhesiveness (FIG. 4), indicating that other genes from the rpl locus are involved in pilus-mediated attachment to eukaryotic cells (not shown).

Example 5

Demonstration that the *R. equi* pili are essential for lung colonization in vivo in a mouse model of *R. equi* infection.

Figure 4:
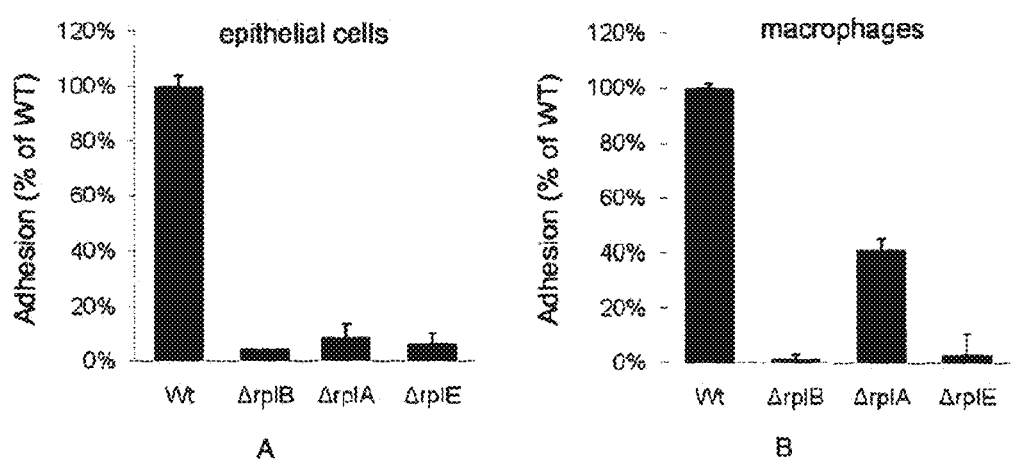
FIG. 4 illustrates the adhesion phenotype to (A) epithelial cells (HeLa cell line) and (B) macrophages (J774A.1 cell line) with additional rpl knock-out mutants (rplA and rplE).

A novel in vivo model of competitive *R. equi* lung infection in mice was developed and used to test the virulence of the rplB mutant in comparison to rplB-proficient (wild-type) bacteria. *R. equi* wild-type and an isogenic rplB knock-out mutant in equal amounts were inoculated intranasally to Balb/c mice. At specific time points after infection, the bacterial population was determined in lungs and tracheas to assess airway colonisation. The spleens were also analysed to determine the capacity of the bacteria to overwhelm local defences and spread deeper into host tissues. FIG. 4 shows that the mutant, initially accounting for 50% of the inoculum, was only detectable—in much less proportion—during the two first time points sampled (0 and 24 hour post inoculation), indicating that apiliated bacteria are immediately cleared from the lungs and thus substantially less virulent. In the first time point, only a very small fraction of the bacteria that translocated to the spleen were mutants. These data indicate that a wild-type capacity to attach to host cells via the Rpl pili is essential for host colonisation by *R. equi*.

Example 6

Demonstration that the RplB (putative pilin subunit) protein is antigenic in vivo in rabbits.

The synthetic RplB peptide indicated in FIG. 6A was used to hyperimmunize rabbits. The antiserum specifically detected the RplB pilin subunit in whole cell extracts of *R. equi* (FIG. 6B) and the production of Rpl pili in *R. equi* by immunofluorescence (FIG. 6C), indicating that it is immunogenic in vivo in rabbits.

Example 7

Demonstration that RplB elicits neutralizing antibodies that inhibit *R. equi* attachment.

The rabbit hyperimmune anti-RplB antiserum was used in attachment-inhibition assays in HeLa epithelial cells and J774A.1 macrophages. FIG. 7 shows that the RplB antiserum, but not an irrelevant antiserum, inhibited *R. equi* cytoadhesion. Given the key role of the Rpl pili in lung colonization by *R. equi* (FIG. 4), these data indicate that RplB is a vaccine target to prevent lung infection by the pathogen.

This is evidence that indicates that the pilin subunit RplB is recognised by the immune system in vivo and the animal body mounts a specific immune response with production of specific antibodies to the *R. equi* pilin subunit RplB. As the polyclonal antiserum containing anti-RplB antibodies inhibits attachment of *R. equi* to monolayers of HeLa epithelial cells or J774 macrophages if added to the infection assays, which effect is not seen if the Rpl antiserum is not added, or if an unrelated control antiserum raised against other bacteria (e.g. *Listeria*) is used, this indicates a protective function of the antibodies through inhibition of bacterial attachment to host cells, the first phase of host colonisation during infection.

Example 8

Demonstration that the RplB putative pilin subunit is an immunodominant antigen in naturally infected foals.

Using SDS-PAGE western immunoblotting and whole-cell extracts from wild-type and rplB (apiliated) deletion mutant bacteria, it was shown that the sera from natural cases of *R. equi* infection in foals contain antibodies to the RplB putative pilin subunit (FIG. 8). The RplB protein is the first detected in the crude *R. equi* protein preparation by the antibodies present in the case sera. Thus, the RplB pilin subunit is recognized in vivo by the foal's immune system during *R. equi* infection and is an immunodominant antigen. Normal, non-case sera did not react against the RplB protein, indicating that this antigen provides a suitable maker for the early detection and diagnosis of *R. equi* infection in foals.

Although the invention has been particularly shown and described with reference to particular examples, it will be understood by those skilled in the art that various changes in the form and details may be made therein without departing from the scope of the present invention.

The invention claimed is:

1. An isolated polypeptide associated with pilus formation in *Rhodococcus equi* comprising an amino acid sequence encoded by a polynucleotide sequence as set forth in SEQ ID NO:2, or an immunogenic fragment that has an amino acid sequence comprising DKITDLFDGFNFDDPGGE (SEQ ID NO:11) wherein the polypeptide or immunogenic fragment is linked to an immunogenic carrier.

2. The isolated polypeptide sequence as claimed in claim 1 comprising an amino acid sequence encoded by a polynucleotide sequence as set forth in SEQ ID NO:2 wherein the polypeptide or immunogenic fragment is linked to an immunogenic carrier.

3. The isolated polypeptide sequence as claimed in claim 1 wherein the polypeptide is encoded by a polynucleotide sequence comprising ATGAACCTCTTCTTCGCGAACCTGTACCTCATGGGCTTAGACGTCAA GGACCGTCTGACCCGTGACGACCGCGGCGCCACTGCGGTCGAGTAC GGACTGATGGTCGCCGGCATCGCGATGGTGATCATTGTTGCGGTTTT CGCCTTCGGCGATAAGATTACCGACCTCTTCGATGGCTTCAACTTCG ACGATCCCGGCGGCGAGTAG (SEQ ID NO:2), and wherein the polypeptide comprises an amino acid sequence MNLFFANLYLMGLDVKDRLTRDDRGATA-VEYGLMVAGIAMVIIVAVFAFG DKITDLFDGFNFD- DPGGE (SEQ ID NO:10) wherein the polypeptide or immunogenic fragment is linked to an immunogenic carrier.

4. A composition comprising a polypeptide associated with pilus formation in *Rhodococcus equi* comprising an amino acid sequence encoded by a polynucleotide sequence as set forth in SEQ ID NO:2, or an immunogenic fragment that has an amino acid sequence comprising DKITDLFDGFNFDDPGGE (SEQ ID NO:11), together with a pharmaceutically acceptable carrier.

5. A method of treating or preventing a disease or condition caused by *Rhodococcus equi*, comprising the step of administering an effective amount to a subject in need thereof of a polypeptide comprising an amino acid sequence encoded by a polynucleotide sequence as set forth in SEQ ID NO:2 or the immunogenic fragment that has an amino acid sequence comprising DKITDLFDGFNFDDPGGE (SEQ ID NO:11).

6. A method of detecting *Rhodococcus equi* wherein the method comprises detecting a polypeptide associated with Rpl pilus formation in *Rhodococcus equi*, comprising an amino acid sequence encoded by an isolated polynucleotide sequence as set forth in SEQ ID NO:2, or the immunogenic fragment that has an amino acid sequence comprising DKITDLFDGFNFDDPGGE (SEQ ID NO:11).

7. A composition capable of generating an immune response in a host comprising one or more surface-associated or secreted polypeptides of *Rhodococcus equi* wherein said polypeptides are isolated, and wherein said polypeptides are associated with formation of pili of *Rhodococcus equi*, wherein said composition comprises an isolated polypeptide comprising an amino acid sequence encoded by a polynucleotide sequence as set forth by SEQ ID NO:2 or the immunogenic fragment that has an amino acid sequence comprising DKITDLFDGFNFDDPGGE (SEQ ID NO:11) wherein the polypeptide or immunogenic fragment is linked to an immunogenic carrier, or a construct comprising an isolated nucleic acid molecule which encodes the isolated polypeptide wherein said isolated nucleic acid molecule is operably linked to a heterologous promoter which is functional to allow transcription of the nucleic acid sequence.

8. A method of inhibiting colonisation of a subject by *Rhodococcus equi* comprising the step of administering to a subject an effective amount of a polypeptide comprising an amino acid sequence encoded by a polynucleotide sequence as set forth in SEQ ID NO: 2 or the immunogenic fragment that has an amino acid sequence comprising DKITDLFDGFNFDDPGGE (SEQ ID NO 11).

9. The method of claim 5 wherein the subject is a horse or foal.

10. The method of claim 8 wherein the subject is a horse or foal.

11. The method of claim 5 wherein the condition is *Rhodococcus* pneumonia.

\* \* \* \* \*

SEQUENCE LISTING

<160> NUMBER OF SEQ ID NOS: 73

<210> SEQ ID NO 1
<211> LENGTH: 702
<212> TYPE: DNA
<213> ORGANISM: Rhodococcus equi

<400> SEQUENCE: 1

| | | | | | |
|---|---|---|---|---|---|
| gtgatcgtcg | cagcgggcgt | cggcgccgca | ctcctgggta | tcctcgccgg | ggcgttcgcg | 60 |
| aacagtgcga | tcgaccgcgt | gcgcctggag | accgcgtgcg | ccgagccgaa | gtcgaccccc | 120 |
| accggctcaa | ccccgccgcc | ccctcccct | gcgtccgcgg | tagccacccg | gatcgcgatg | 180 |
| atcgacacca | tcacgcgacg | acacgacatc | agtgcccgcc | gcgtgctcgt | cgaactcgca | 240 |
| acggccctcc | tgttcgtcgg | gatcactctc | cgtctcgccg | ctctcggtct | tctcccggca | 300 |
| acaccggcct | atctcttgca | aacggctgcc | gaacttcctc | gtcgtaccgt | cgtacccgat | 360 |
| cgtattcgcc | tgcctttcag | tgggttccgt | cgtgccgttc | tgttcggggt | ctacttcgta | 420 |
| ctagccctga | tctatccggc | cggcatgggg | ttcggcgacg | tcaaacttgc | cggcgtcatc | 480 |
| ggcgccgtcc | tcgcctacct | gtcgtacggc | acattgctcg | tcggggcgtt | tctcgcgttc | 540 |
| ctggtggccg | cactcgtcgg | cctgatcatc | ctggtcaccc | gtcgcggtcg | gatcgggacc | 600 |
| acgattccct | tcgggccgta | catgattgcg | cggccatcg | ttgcgatcct | ggcggccgat | 660 |
| ccgctggcgc | gcgcgtatct | ggactgggcc | gccgcggcct | ga | | 702 |

<210> SEQ ID NO 2
<211> LENGTH: 207
<212> TYPE: DNA
<213> ORGANISM: Rhodococcus equi

<400> SEQUENCE: 2

| | | | | | |
|---|---|---|---|---|---|
| atgaacctct | tcttcgcgaa | cctgtacctc | atgggcttag | acgtcaagga | ccgtctgacc | 60 |
| cgtgacgacc | gcggcgccac | tgcggtcgag | tacggactga | tggtcgccgg | catcgcgatg | 120 |
| gtgatcattg | ttgcggtttt | cgccttcggc | gataagatta | ccgacctctt | cgatggcttc | 180 |
| aacttcgacg | atcccggcgg | cgagtag | | | | 207 |

<210> SEQ ID NO 3
<211> LENGTH: 402
<212> TYPE: DNA
<213> ORGANISM: Rhodococcus equi

<400> SEQUENCE: 3

| | | | | | |
|---|---|---|---|---|---|
| atgaagcgcc | tcacttccga | ttcaggggtc | gccgcagtcg | aattcgctct | cgtcgttccg | 60 |
| atcctgatca | cactggtcct | cggcatcgtg | gagttcggtc | ggggttacaa | cgtccagaac | 120 |
| gcggtcagcg | ctgctgcccg | cgagggtgca | cggacgatgg | cgatcaagaa | ggatccggcg | 180 |
| gcggcgcgtg | ctgccgtgaa | gggcgcgggt | gtgttcagtc | cggcgatcac | cgatgcggag | 240 |
| atctgcatca | gcacttcggg | aacgcagggc | tgttcggcaa | cgtcgtgtcc | gagcggaagt | 300 |
| accgtgacgc | tcacggtcag | ctatccactc | gagtacatga | cgggactctt | tcccggtaag | 360 |
| ccgacgctca | ccggcacggg | ggtcatgcga | tgcggtgggt | ga | | 402 |

<210> SEQ ID NO 4
<211> LENGTH: 945
<212> TYPE: DNA
<213> ORGANISM: Rhodococcus equi

<400> SEQUENCE: 4

```
atgtcgaatg acgagcgcgg ggtcgtcgcc gtgctcgttg cgatcctcat ggtcgtgctc        60
ctgggatgtg ctgcgatctc ggtcgacatc ggtgcgaact atgtcgtcaa acgtcagttg       120
cagaacgggg ccgatgcggc tgcgctcgcc gtagctcagg aatccagttg caaggcagga       180
tcttccgcct catccgtgtc gagccttgtc caggcgaacg tcaacagctc gtcggctgca       240
agtgcggcgg tgatcgacgg tgtgaagcgg aaggtgacgg tcactgcgtc ggcggtgggt       300
gacgacggcc tcgccggccg gaggaacgtg ttcgctccgg tcctcggagt cgaccgcagc       360
gagatctcgg cgtctgcgac tgcaagctgc gtgtttcccc tcgggggggac cgcggaactc       420
ccgctcacgt tccacaagtg ccatttcgac gaatcccgca gtctggacgt gaagatcctc       480
gtcgcctaca acgtgacggc gccgcgctgc aatggaacct cgggaaatgc ggcaccgggc       540
aatttcggct ggctgcaggg ggcgaacggt cgatgcccgg cgaagatcga cgccgccgtc       600
tacgcaacac cgggcgacac cggtaacaac attccggggc cgtgcaagga caccatcaag       660
cagtttcaga atgccgtcgt gcgggtcccg atctacgacg tcgcaggtgg aaccggaagc       720
ggtggatggt ttcacgtcgt cggtttggct gccttcaaga ttcagggcta ccggctgagc       780
ggcaacccgg agttcaactg gaacaacgat gttcacgggg cgctgagttg caccggcagc       840
tgtcgcggca tcatcggcac cttcgtgaag attgtcagcc tcgattcgga tctgacgccg       900
ggagggatcg atttcggcgt gagtacgatc agcttgctcg attag                       945

<210> SEQ ID NO 5
<211> LENGTH: 738
<212> TYPE: DNA
<213> ORGANISM: Rhodococcus equi

<400> SEQUENCE: 5
ttgagaaccc gaatcattgc tgcgatctgt gcgatcgttc tcgcggtcgc gggaaccctc        60
gccctgatct cgtatgtacg cggggccgat gcccgcgccc tggcgggtac acgcaccgtc       120
gatgtgctcg tcgccgatca gacgattccg aagaacactc ccgctgattc gctcgtggga       180
atggttgtgg tcaagaaact tccggaaatg gcggtgctac ccgatcgggt gaccagtctc       240
gaccaactgt ccggcaaggt cgcgctgacc gacctcctgc ctggcgaaca actggtctcg       300
gcgcgattcg tcgacccggc gaccgcccga agtcaggacc agggaggaat ccccgagggg       360
atgcaggagg tgacggttct tctcgagccg caacgcgcac tgggaggcca catcgcgtcg       420
ggcgataccg tcggcgtctt catgtccttc tcgccgcccg tcaagaacta cgaaacacat       480
ctgagattgc agaaagtgcg agtcacgcgg gtccaggaa cgttctccaa cgccgacgaa       540
ggggattcgg ccacggtcga ctcgtcgccg agccctgctc ccaccgaggc ctttctcgtc       600
tcgctggcgt tcgacgtgcc gatggcggag cgcgtcgttt tcgccgcgga gcacgggacc       660
atctggcttt ccaatgagcc gccgagttcg aacgaggccg gggcatccgt ggtctccccg       720
gaaggagtgt tccgatga                                                     738

<210> SEQ ID NO 6
<211> LENGTH: 1200
<212> TYPE: DNA
<213> ORGANISM: Rhodococcus equi

<400> SEQUENCE: 6
atgagccgca tcgtcctgct gaccgatcgc gacgatttcg cccgccgcgt gtaccacgcc        60
gcggacggca accttctggt gttgccggcg cagccggttc ccgggggggcc ggcgcagttg       120
```

```
gtcgggctcg gcgtgaccgt gcaaccagaa gttctcgttc tcggtccgga cgtgccggaa      180
gtggagggcc tctccctcgc cggccggatc gatcattcga cgcccggcac cacggtggtt      240
ctggccagtg atgcgggcac cgacgtgtgg ttgcgggcga tgcgcgccgg cgtgcgggac      300
gtgatgtcgc cggaggcgga gatcgcggac gttcgtgcgg tactcgatcg agcgggccag      360
gccgcactgg cgcgacgtca gggggcgagt gcaccggcgg agcagcatgc ggttcaaggg      420
aaggtcatcg tggtcgcgtc gccgaaaggc ggaaccggaa agaccaccgt tgcgacgaat      480
cttgcagtag gactcgcggc ggcagcgcct cactcgacgg tgttggtgga cctcgacgtg      540
cagttcgggg acgttgccag tgctctccag ttggttccgg aacattgcct gaccgacgcc      600
gtcgcgggcc cggccagcca ggacatgatc gtcctcaaga ccgtcctgac accccattcc      660
acaggactgc atgcgctgtg tgggtcggac tcgcccgcgg cgggcgacag catcaccggc      720
gagcaggtga gcactctgct gacgcagttg gcggccgaat ccggtacgt ggtcgtcgac       780 accgcgcccg gtttgctcga acacaccctg gcggcgctcg accttgctac cgacgtcgtg      840
ttggtgtcgg gtatgacgt gcccagcgtc cgcgggatgc acaaggaact gcaattgctg       900
acggagctga atctgggtcc ggtcgtgcgg catgtcgtgc tcaactttgc ggatcgacgc      960
gaggggctga cggtccagga catccagaac accatcgggg tccccgccga tatcgtgatc     1020
aagcgctcga aagccgttgc cctctcgacg aaccgggggg ttccactgct tcagaacccg     1080
ggtcgggatc gcactgcgaa agagttgtgg cgactcgtcg gccgtatcga tccggctccc     1140
gataccgcca agggtggacg cgcgcggcat cgggcagccg aggcggtggg tgcgaaatga     1200
```

<210> SEQ ID NO 7
<211> LENGTH: 1398
<212> TYPE: DNA
<213> ORGANISM: Rhodococcus equi

<400> SEQUENCE: 7

```
atgagactgt cccaacggct cgaggccgtg cgcggagccg cacccgtcga agccgccgca       60
ccgatcccgc cggggaagca ggggaaggcg aaaacgtccc tccctccggc cgacgctctc      120
gccgaactga aggaccgtgc gagtgcggcc ctgtacaccc ggatcggcac ccgcttcaac      180
gactcctcgt tgagcgagga gcaactgcat ctcctggtcc gtgaggaact ggccgaaatc      240
gtggagcagg agacgacgcc actcaccttc gacgaacggc agcgcctgct ccgtgaggtt      300
gccgacgagg tactggggca cggaccgctc cagcggctac tggaggaccc gtcggtcacc      360
gagatcatgg tcaacagcca cgacatggtc tacgtcgagc gggacggcac cctcgtccgc      420
agctccgcgc gattcgcgga cgaggcgcac ctgcgtcgcg tgatcgaacg catcgtttcc      480
gccgtcggtc gacggatcga cgaatcgtcc ccgctcgtgg atgcacgctt ggcggatggc      540
tcccgtgtca acgcggtgat cccaccgctc gcattcaacg gctcctcgct caccattcga      600
aagttctcga agatccgtt ccaggtcgac gatctcatcg ccttcggcac tctctcgcac      660
gagatggccc aactgctcga cgcgtgtgtg caggcgcgac tgaacgtcat cgtctcgggc      720
ggcacgggca cggggaagac gacgctgctc aacgtgctct cgtcgttcat tccggaaggg      780
gagcggatct tcaccatcga ggacgccgtg gaactgcaac ttcagcagga ccacgtcgta      840
cggttggaga gccgaccgcc gaacatcgag ggcaagggtg ccgtcaccat ccgcgacctg      900
gtgcggaact cgctgcgtat gcgtcccgac cgcatcgtgg tggggagtg tcgcggaggc       960 gagagtctcg acatgctgca agcgatgaac accggtcacg acgggtcgct gtcgacggtc     1020
catgcgaatt cgccccgtga cgccatcgcg cgcttggaga cgctcgtgtt gatggccggc     1080
```

```
atggacctgc cgttgcgggc gatccgggag cagattgctt cggcggtcga cgtgatcgtg    1140
cagctcactc gactacgtga cggcactcgg cgagtgaccc acgtgaccga ggtccagggc    1200
atggagggtg agatcgtcac cctgcaggat gccttcctgt cgactacag cgccggcgtc     1260 gacgcgcgcg gcgattcct cggcagaccg cagccgaccg gagtgcggcc gcggttcacc    1320
gacagattcc gagatctcgg tattgctttg tcgccgagtg ttttcggggt gggagaaccc    1380
tcccgggggc gggtatga                                                  1398
```

<210> SEQ ID NO 8
<211> LENGTH: 1869
<212> TYPE: DNA
<213> ORGANISM: Rhodococcus equi

<400> SEQUENCE: 8

```
atgagccggt gcgtggtggc cgtcgtgctc gccctcggtg cgggtgttct gggaattccc      60
gccgtagccg cggcggccga ggaggctgtc caggtctcgg cggtcgacac gacccggttt     120
cccgacatcg aggtgtccat cctcgcgccg cccggtatcg aagggcaggc gatcgatccg     180
ggaacgttcg cgctcaccga gggcggcgtg ccgcgagaga tcgaggtcag gcagcagccg     240
ggttccgagc aggacatcgt gctcgcaatc gacgtgtccg ggggcatgtc gggtccggcg     300
ctggacgacg tgaagcgcgc cgcatcggat ttcgtgcggc aggcgccggc cggcgcccac     360
atcggaatcg tcgcgatctc gtcgacgcca caggtgctct cggaactgac gacggactcc     420
gaggacctgc tccgcaggat cgacggactg aaggcgggcg caacagcgc gatcgcagat     480 cggtggtga ccgccgccga gatgctcgag cgcggcgaag cggccaacaa catcctgctt     540
ctgttgacgg acggcgccga cacgtcgagt gcacactcga tgtcggaact cccgtccgtc     600
ctgagtcggt cgcgcgcgtc gctgtacgcc gtgcagatgt cgacacccga gacgaactct     660
gctctcctgc agcaggttgc gcgggagtcg cgcggtcagt acgcgtctgc gggtgatacg     720
gcggcgctgg gtgcgatcta ccagtcggcc gctcgcgcgc tcggaaaccct gtacgtcgtc     780 cgataccgat cggaagcgaa tggcgatacc caggtggtgg cgagcgtgcg cagcggcgca     840
gccggccgag tgagcgatcc gttcccggtg acattgcccg gtgtggtgcc gacgccgagc     900
gtcgtcgccg ggaccgtcga cggtttcttc acgtcttcga cggggctggt gatcgggctc     960
ctagcgtgct actcggcgct tgcgggaggc gtgctggcgg tcgccggtag agcgcccgcg    1020
aggatttcgg cagcacgtcg tgggcggcag gacggacggg actcgatgct gtcccgattc    1080
gcggaacggc tggtgcagtg gatcgatcag aacctgagga gacgcggacg catcgctgcc    1140
cgcacccagg cgctacagga ggcgggggctg aagcttcgtc caggtgactt catcgccctg    1200
gtcggtgctg cggcgatcac cgctgcgcg atcggtctcc tggcttcggg catcgtggcg    1260
gcgctcttgc tcgcggcgat cacagtggga ttgtcgagaa tctatctccg tgtgatggcc    1320
ggtaggcgtc gggccgcgtt cgctgatcag ctcgacgatt ccctgcagct gctggccagc    1380
aatctccgag ccgggcacag catgctccga gcgctcgatt ccctttcccg agaggcggag    1440
gtgccgactt cggaggagtt cgctcggatc gtcaacgaga ctcgggtggg acgtgatctc    1500
aacgagtctc tcgacgacgt ggcccggcgg atgcgaagtg acgatttcaa ctggatagct    1560
caggcaatcg ccatcaaccg tgaggtcgga ggcgacctcg cggaagtcct cgaccaggtg    1620
ggcaacacca ttcgagagcg aaatcagatt cgacggcagg tgaaagccct tgctgccgag    1680
gggaaactgt ccgcctacgt gctgatggcg ctgcccttcg gtctcaccgc atttctgctc    1740
```

```
gtctcgaatc cggactacct gtcgaagttg acgggtagcg ccatcggcta cgtgatgatc    1800
gcggtggggc tcgtcatgct gaccgtcggt gggctgtgga tgaacaaggt tgtctcggtc    1860
aagttctag                                                             1869

<210> SEQ ID NO 9
<211> LENGTH: 891
<212> TYPE: DNA
<213> ORGANISM: Rhodococcus equi

<400> SEQUENCE: 9
gtgattccac cgctggtgct catggcggcg ctgtccgtcg gcggggcgtt gggtgttctg      60
gtgtggttga cggtcggcgc ccgagatccg gaacgcggac ccgcccttcg gaacctgcag     120
tcgcagctgg cgttgccgat tccggagtcg ggaggcgcgc caccgctttc gctcggccga     180
ttcgtgaagc tgctgtcgcc gcccgggacg atggcccgct ggaacgact gcacatcctt     240 gccggtcgtc cagcggcgtg ggttccggaa cgggccgcga tggcgaagat cgttctcgcc     300
gcggccgccg ccctgctcgg ccttctcgcg gtgggtgcgt cgcctggcgt cggccgggtg     360
ctgttcgctg cggccgccgt cgcgctggcg tatttcgtcc cggaacttct cctgcagagc     420
agggggcagg agcgccaagc cgcgatcgaa ctggcgcttg ccgacaccct cgaccagatg     480
acgatcgcag tcgaggcggg cctggggttc gaagccgcca tgcagcgggc cgcgaagaac     540 ggaaagggc cgctggccga ggaattcatc cggacattgc aggacataca gatggggcag     600
tcgaggcgaa tcgcgtacct ggatcttgcc gccagaacga aagcacccaa cttgcggagg     660
ttccttcggg ccgtcatcca agccgacgag tacggcgtgg ccatcgccga ggtcctgcgg     720
acccaggcct cggagatgcg tctgaaacgc cgtcagagtg ctgaggagaa ggcgatgaag     780
gttccggtga agtgctgtt ccgttgatg acctgcatcc tgccgaccat cttcatcgtg     840
atcctgggtc cggcggtgat caacatgatg gaggtcttgg gcggtatgta a              891

<210> SEQ ID NO 10
<211> LENGTH: 68
<212> TYPE: PRT
<213> ORGANISM: Rhodococcus equi

<400> SEQUENCE: 10

Met Asn Leu Phe Phe Ala Asn Leu Tyr Leu Met Gly Leu Asp Val Lys
1               5                   10                  15

Asp Arg Leu Thr Arg Asp Asp Arg Gly Ala Thr Ala Val Glu Tyr Gly
            20                  25                  30

Leu Met Val Ala Gly Ile Ala Met Val Ile Val Ala Val Phe Ala
        35                  40                  45

Phe Gly Asp Lys Ile Thr Asp Leu Phe Asp Gly Phe Asn Phe Asp Asp
    50                  55                  60

Pro Gly Gly Glu
65

<210> SEQ ID NO 11
<211> LENGTH: 18
<212> TYPE: PRT
<213> ORGANISM: Rhodococcus equi

<400> SEQUENCE: 11

Asp Lys Ile Thr Asp Leu Phe Asp Gly Phe Asn Phe Asp Asp Pro Gly
1               5                   10                  15

Gly Glu
```

```
<210> SEQ ID NO 12
<211> LENGTH: 262
<212> TYPE: PRT
<213> ORGANISM: Rhodococcus equi

<400> SEQUENCE: 12

Val Ile Val Ala Ala Gly Val Ala Ala Leu Leu Gly Ile Leu Ala
1               5                   10                  15

Gly Ala Phe Ala Asn Ser Ala Ile Asp Arg Val Arg Leu Glu Thr Ala
                20                  25                  30

Cys Ala Glu Pro Lys Ser Thr Pro Thr Gly Ser Thr Pro Pro Pro
            35                  40                  45

Ser Pro Ala Ser Ala Val Ala Thr Arg Ile Ala Met Ile Asp Thr Ile
    50                  55                  60

Thr Arg Arg His Asp Ile Ser Ala Arg Arg Val Leu Val Glu Leu Ala
65                  70                  75                  80

Thr Ala Leu Leu Phe Val Gly Ile Thr Leu Arg Leu Ala Ala Leu Gly
                85                  90                  95

Leu Leu Pro Ala Thr Pro Ala Tyr Leu Trp Phe Ala Val Gly Ile
            100                 105                 110

Ala Leu Ala Val Ile Asp Ile Asp Cys Lys Arg Leu Pro Asn Phe Leu
            115                 120                 125

Val Val Pro Ser Tyr Pro Ile Val Phe Ala Cys Leu Ser Val Gly Ser
        130                 135                 140

Val Val Thr Gly Asp Trp Ser Ala Leu Leu Arg Ala Ala Ile Gly Ala
145                 150                 155                 160

Ala Val Leu Phe Gly Val Tyr Phe Val Leu Ala Leu Ile Tyr Pro Ala
                165                 170                 175

Gly Met Gly Phe Gly Asp Val Lys Leu Ala Gly Val Ile Gly Ala Val
            180                 185                 190

Leu Ala Tyr Leu Ser Tyr Gly Thr Leu Leu Val Gly Ala Phe Leu Ala
        195                 200                 205

Phe Leu Val Ala Ala Leu Val Gly Leu Ile Ile Leu Val Thr Arg Arg
    210                 215                 220

Gly Arg Ile Gly Thr Thr Ile Pro Phe Gly Pro Tyr Met Ile Ala Ala
225                 230                 235                 240

Ala Ile Val Ala Ile Leu Ala Ala Asp Pro Leu Ala Arg Ala Tyr Leu
                245                 250                 255

Asp Trp Ala Ala Ala Ala
            260

<210> SEQ ID NO 13
<211> LENGTH: 68
<212> TYPE: PRT
<213> ORGANISM: Rhodococcus equi

<400> SEQUENCE: 13

Met Asn Leu Phe Phe Ala Asn Leu Tyr Leu Met Gly Leu Asp Val Lys
1               5                   10                  15

Asp Arg Leu Thr Arg Asp Arg Gly Ala Thr Ala Val Glu Tyr Gly
                20                  25                  30

Leu Met Val Ala Gly Ile Ala Met Val Ile Ile Val Ala Val Phe Ala
            35                  40                  45

Phe Gly Asp Lys Ile Thr Asp Leu Phe Asp Gly Phe Asn Phe Asp Asp
        50                  55                  60
```

Pro Gly Gly Glu
65

<210> SEQ ID NO 14
<211> LENGTH: 133
<212> TYPE: PRT
<213> ORGANISM: Rhodococcus equi

<400> SEQUENCE: 14

Met Lys Arg Leu Thr Ser Asp Ser Gly Val Ala Ala Val Glu Phe Ala
1               5                   10                  15

Leu Val Val Pro Ile Leu Ile Thr Leu Val Leu Gly Ile Val Glu Phe
            20                  25                  30

Gly Arg Gly Tyr Asn Val Gln Asn Ala Val Ser Ala Ala Ala Arg Glu
        35                  40                  45

Gly Ala Arg Thr Met Ala Ile Lys Lys Asp Pro Ala Ala Ala Arg Ala
    50                  55                  60

Ala Val Lys Gly Ala Gly Val Phe Ser Pro Ala Ile Thr Asp Ala Glu
65                  70                  75                  80

Ile Cys Ile Ser Thr Ser Gly Thr Gln Gly Cys Ser Ala Thr Ser Cys
                85                  90                  95

Pro Ser Gly Ser Thr Val Thr Leu Thr Val Ser Tyr Pro Leu Glu Tyr
            100                 105                 110

Met Thr Gly Leu Phe Pro Gly Lys Pro Thr Leu Thr Gly Thr Gly Val
        115                 120                 125

Met Arg Cys Gly Gly
    130

<210> SEQ ID NO 15
<211> LENGTH: 314
<212> TYPE: PRT
<213> ORGANISM: Rhodococcus equi

<400> SEQUENCE: 15

Met Ser Asn Asp Glu Arg Gly Val Val Ala Val Leu Val Ala Ile Leu
1               5                   10                  15

Met Val Val Leu Leu Gly Cys Ala Ala Ile Ser Val Asp Ile Gly Ala
            20                  25                  30

Asn Tyr Val Val Lys Arg Gln Leu Gln Asn Gly Ala Asp Ala Ala Ala
        35                  40                  45

Leu Ala Val Ala Gln Glu Ser Ser Cys Lys Ala Gly Ser Ser Ala Ser
    50                  55                  60

Ser Val Ser Ser Leu Val Gln Ala Asn Val Asn Ser Ser Ser Ala Ala
65                  70                  75                  80

Ser Ala Ala Val Ile Asp Gly Val Lys Arg Lys Val Thr Val Thr Ala
                85                  90                  95

Ser Ala Val Gly Asp Asp Gly Leu Ala Gly Arg Arg Asn Val Phe Ala
            100                 105                 110

Pro Val Leu Gly Val Asp Arg Ser Glu Ile Ser Ala Ser Ala Thr Ala
        115                 120                 125

Ser Cys Val Phe Pro Leu Gly Gly Thr Ala Glu Leu Pro Leu Thr Phe
    130                 135                 140

His Lys Cys His Phe Asp Glu Ser Arg Ser Leu Asp Val Lys Ile Leu
145                 150                 155                 160

Val Ala Tyr Asn Val Thr Ala Pro Arg Cys Asn Gly Ser Gly Asn
                165                 170                 175

```
Ala Ala Pro Gly Asn Phe Gly Trp Leu Gln Gly Ala Asn Gly Arg Cys
            180                 185                 190

Pro Ala Lys Ile Asp Ala Ala Val Tyr Ala Thr Pro Gly Asp Thr Gly
        195                 200                 205

Asn Asn Ile Pro Gly Pro Cys Lys Asp Thr Ile Lys Gln Phe Gln Asn
    210                 215                 220

Ala Val Arg Val Pro Ile Tyr Asp Val Ala Gly Thr Gly Ser
225                 230                 235                 240

Gly Gly Trp Phe His Val Val Gly Leu Ala Ala Phe Lys Ile Gln Gly
                    245                 250                 255

Tyr Arg Leu Ser Gly Asn Pro Glu Phe Asn Trp Asn Asn Asp Val His
                260                 265                 270

Gly Ala Leu Ser Cys Thr Gly Ser Cys Arg Gly Ile Ile Gly Thr Phe
                275                 280                 285

Val Lys Ile Val Ser Leu Asp Ser Asp Leu Thr Pro Gly Gly Ile Asp
            290                 295                 300

Phe Gly Val Ser Thr Ile Ser Leu Leu Asp
305                 310

<210> SEQ ID NO 16
<211> LENGTH: 245
<212> TYPE: PRT
<213> ORGANISM: Rhodococcus equi

<400> SEQUENCE: 16

Leu Arg Thr Arg Ile Ile Ala Ala Ile Cys Ala Ile Val Leu Ala Val
1               5                   10                  15

Ala Gly Thr Leu Ala Leu Ile Ser Tyr Val Arg Gly Ala Asp Ala Arg
            20                  25                  30

Ala Leu Ala Gly Thr Arg Thr Val Asp Val Leu Val Ala Asp Gln Thr
        35                  40                  45

Ile Pro Lys Asn Thr Pro Ala Asp Ser Leu Val Gly Met Val Val Val
    50                  55                  60

Lys Lys Leu Pro Glu Met Ala Val Leu Pro Asp Arg Val Thr Ser Leu
65                  70                  75                  80

Asp Gln Leu Ser Gly Lys Val Ala Leu Thr Asp Leu Leu Pro Gly Glu
                85                  90                  95

Gln Leu Val Ser Ala Arg Phe Val Asp Pro Ala Thr Ala Arg Ser Gln
            100                 105                 110

Asp Gln Gly Gly Ile Pro Glu Gly Met Gln Glu Val Thr Val Leu Leu
        115                 120                 125

Glu Pro Gln Arg Ala Leu Gly Gly His Ile Ala Ser Gly Asp Thr Val
    130                 135                 140

Gly Val Phe Met Ser Phe Ser Pro Pro Val Lys Asn Tyr Glu Thr His
145                 150                 155                 160

Leu Arg Leu Gln Lys Val Arg Val Thr Arg Val Gln Gly Thr Phe Ser
                165                 170                 175

Asn Ala Asp Glu Gly Asp Ser Ala Thr Val Asp Ser Ser Pro Ser Pro
            180                 185                 190

Ala Pro Thr Glu Ala Phe Leu Val Ser Leu Ala Val Asp Val Pro Met
        195                 200                 205

Ala Glu Arg Val Val Phe Ala Ala Glu His Gly Thr Ile Trp Leu Ser
    210                 215                 220

Asn Glu Pro Pro Ser Ser Asn Glu Ala Gly Ala Ser Val Val Ser Pro
```

```
                225                 230                 235                 240

Glu Gly Val Phe Arg
                245

<210> SEQ ID NO 17
<211> LENGTH: 399
<212> TYPE: PRT
<213> ORGANISM: Rhodococcus equi

<400> SEQUENCE: 17

Met Ser Arg Ile Val Leu Leu Thr Asp Arg Asp Asp Phe Ala Arg Arg
  1               5                  10                  15

Val Tyr His Ala Ala Asp Gly Asn Leu Val Leu Pro Ala Gln Pro
             20                  25                  30

Val Pro Arg Gly Pro Ala Gln Leu Val Gly Leu Gly Val Thr Val Gln
         35                  40                  45

Pro Glu Val Leu Val Leu Gly Pro Asp Val Pro Glu Val Glu Gly Leu
     50                  55                  60

Ser Leu Ala Gly Arg Ile Asp His Ser Thr Pro Gly Thr Thr Val Val
 65                  70                  75                  80

Leu Ala Ser Asp Ala Gly Thr Asp Val Trp Leu Arg Ala Met Arg Ala
                 85                  90                  95

Gly Val Arg Asp Val Met Ser Pro Glu Ala Glu Ile Ala Asp Val Arg
            100                 105                 110

Ala Val Leu Asp Arg Ala Gly Gln Ala Ala Leu Ala Arg Arg Gln Gly
        115                 120                 125

Ala Ser Ala Pro Ala Glu Gln His Ala Val Gln Gly Lys Val Ile Val
    130                 135                 140

Val Ala Ser Pro Lys Gly Gly Thr Gly Lys Thr Thr Val Ala Thr Asn
145                 150                 155                 160

Leu Ala Val Gly Leu Ala Ala Ala Pro His Ser Thr Val Leu Val
                165                 170                 175

Asp Leu Asp Val Gln Phe Gly Asp Val Ala Ser Ala Leu Gln Leu Val
            180                 185                 190

Pro Glu His Cys Leu Thr Asp Ala Val Ala Gly Pro Ala Ser Gln Asp
        195                 200                 205

Met Ile Val Leu Lys Thr Val Leu Thr Pro His Ser Thr Gly Leu His
    210                 215                 220

Ala Leu Cys Gly Ser Asp Ser Pro Ala Ala Gly Asp Ser Ile Thr Gly
225                 230                 235                 240

Glu Gln Val Ser Thr Leu Leu Thr Gln Leu Ala Ala Glu Phe Arg Tyr
                245                 250                 255

Val Val Val Asp Thr Ala Pro Gly Leu Leu Glu His Thr Leu Ala Ala
            260                 265                 270

Leu Asp Leu Ala Thr Asp Val Val Leu Val Ser Gly Met Asp Val Pro
        275                 280                 285

Ser Val Arg Gly Met His Lys Glu Leu Gln Leu Thr Glu Leu Asn
    290                 295                 300

Leu Gly Pro Val Val Arg His Val Val Leu Asn Phe Ala Asp Arg Arg
305                 310                 315                 320

Glu Gly Leu Thr Val Gln Asp Ile Gln Asn Thr Ile Gly Val Pro Ala
                325                 330                 335

Asp Ile Val Ile Lys Arg Ser Lys Ala Val Ala Leu Ser Thr Asn Arg
            340                 345                 350
```

```
Gly Val Pro Leu Leu Gln Asn Pro Gly Arg Asp Arg Thr Ala Lys Glu
            355                 360                 365

Leu Trp Arg Leu Val Gly Arg Ile Asp Pro Ala Pro Asp Thr Ala Lys
370                 375                 380

Gly Gly Arg Ala Arg His Arg Ala Ala Glu Ala Val Gly Ala Lys
385                 390                 395

<210> SEQ ID NO 18
<211> LENGTH: 465
<212> TYPE: PRT
<213> ORGANISM: Rhodococcus equi

<400> SEQUENCE: 18

Met Arg Leu Ser Gln Arg Leu Glu Ala Val Arg Gly Ala Ala Pro Val
1               5                   10                  15

Glu Ala Ala Ala Pro Ile Pro Pro Gly Lys Gln Gly Lys Ala Lys Thr
                20                  25                  30

Ser Leu Pro Pro Ala Asp Ala Leu Ala Glu Leu Lys Asp Arg Ala Ser
            35                  40                  45

Ala Ala Leu Tyr Thr Arg Ile Gly Thr Arg Phe Asn Asp Ser Ser Leu
        50                  55                  60

Ser Glu Glu Gln Leu His Leu Leu Val Arg Glu Gly Leu Ala Glu Ile
65                  70                  75                  80

Val Glu Gln Glu Thr Thr Pro Leu Thr Phe Asp Glu Arg Gln Arg Leu
                85                  90                  95

Leu Arg Glu Val Ala Asp Glu Val Leu Gly His Gly Pro Leu Gln Arg
            100                 105                 110

Leu Leu Glu Asp Pro Ser Val Thr Glu Ile Met Val Asn Ser His Asp
        115                 120                 125

Met Val Tyr Val Glu Arg Asp Gly Thr Leu Val Arg Ser Ser Ala Arg
    130                 135                 140

Phe Ala Asp Glu Ala His Leu Arg Arg Val Ile Glu Arg Ile Val Ser
145                 150                 155                 160

Ala Val Gly Arg Arg Ile Asp Glu Ser Ser Pro Leu Val Asp Ala Arg
                165                 170                 175

Leu Ala Asp Gly Ser Arg Val Asn Ala Val Ile Pro Pro Leu Ala Phe
            180                 185                 190

Asn Gly Ser Ser Leu Thr Ile Arg Lys Phe Ser Lys Asp Pro Phe Gln
        195                 200                 205

Val Asp Asp Leu Ile Ala Phe Gly Thr Leu Ser His Glu Met Ala Glu
    210                 215                 220

Leu Leu Asp Ala Cys Val Gln Ala Arg Leu Asn Val Ile Val Ser Gly
225                 230                 235                 240

Gly Thr Gly Thr Gly Lys Thr Thr Leu Leu Asn Val Leu Ser Ser Phe
                245                 250                 255

Ile Pro Glu Gly Glu Arg Ile Val Thr Ile Glu Asp Ala Val Glu Leu
            260                 265                 270

Gln Leu Gln Gln Asp His Val Val Arg Leu Glu Ser Arg Pro Pro Asn
        275                 280                 285

Ile Glu Gly Lys Gly Ala Val Thr Ile Arg Asp Leu Val Arg Asn Ser
    290                 295                 300

Leu Arg Met Arg Pro Asp Arg Ile Val Val Gly Glu Cys Arg Gly Gly
305                 310                 315                 320

Glu Ser Leu Asp Met Leu Gln Ala Met Asn Thr Gly His Asp Gly Ser
                325                 330                 335
```

```
Leu Ser Thr Val His Ala Asn Ser Pro Arg Asp Ala Ile Ala Arg Leu
            340                 345                 350

Glu Thr Leu Val Leu Met Ala Gly Met Asp Leu Pro Leu Arg Ala Ile
355                 360                 365

Arg Glu Gln Ile Ala Ser Ala Val Asp Val Ile Val Gln Leu Thr Arg
        370                 375                 380

Leu Arg Asp Gly Thr Arg Arg Val Thr His Val Thr Glu Val Gln Gly
385                 390                 395                 400

Met Glu Gly Glu Ile Val Thr Leu Gln Asp Ala Phe Leu Phe Asp Tyr
                405                 410                 415

Ser Ala Gly Val Asp Ala Arg Gly Arg Phe Leu Gly Arg Pro Gln Pro
            420                 425                 430

Thr Gly Val Arg Pro Arg Phe Thr Asp Arg Phe Arg Asp Leu Gly Ile
            435                 440                 445

Ala Leu Ser Pro Ser Val Phe Gly Val Gly Glu Pro Ser Arg Gly Arg
        450                 455                 460

Val
465

<210> SEQ ID NO 19
<211> LENGTH: 622
<212> TYPE: PRT
<213> ORGANISM: Rhodococcus equi

<400> SEQUENCE: 19

Met Ser Arg Cys Val Ala Val Val Leu Ala Leu Gly Ala Gly Val
1               5                   10                  15

Leu Gly Ile Pro Ala Val Ala Ala Ala Glu Glu Ala Val Gln Val
            20                  25                  30

Ser Ala Val Asp Thr Thr Arg Phe Pro Asp Ile Glu Val Ser Ile Leu
            35                  40                  45

Ala Pro Pro Gly Ile Glu Gly Gln Ala Ile Asp Pro Gly Thr Phe Ala
        50                  55                  60

Leu Thr Glu Gly Gly Val Pro Arg Glu Ile Glu Val Arg Gln Gln Pro
65                  70                  75                  80

Gly Ser Glu Gln Asp Ile Val Leu Ala Ile Asp Val Ser Gly Gly Met
                85                  90                  95

Ser Gly Pro Ala Leu Asp Asp Val Lys Arg Ala Ala Ser Asp Phe Val
            100                 105                 110

Arg Gln Ala Pro Ala Gly Ala His Ile Gly Ile Val Ala Ile Ser Ser
        115                 120                 125

Thr Pro Gln Val Leu Ser Glu Leu Thr Thr Asp Ser Glu Asp Leu Leu
    130                 135                 140

Arg Arg Ile Asp Gly Leu Lys Ala Gly Gly Asn Ser Ala Ile Ala Asp
145                 150                 155                 160

Ser Val Val Thr Ala Ala Glu Met Leu Glu Arg Gly Glu Ala Ala Asn
                165                 170                 175

Asn Ile Leu Leu Leu Leu Thr Asp Gly Ala Asp Thr Ser Ser Ala His
            180                 185                 190

Ser Met Ser Glu Leu Pro Ser Val Leu Ser Arg Ser Arg Ala Ser Leu
        195                 200                 205

Tyr Ala Val Gln Met Ser Thr Pro Glu Thr Asn Ser Ala Leu Leu Gln
    210                 215                 220

Gln Val Ala Arg Glu Ser Arg Gly Gln Tyr Ala Ser Ala Gly Asp Thr
```

```
                225                 230                 235                 240
        Ala Ala Leu Gly Ala Ile Tyr Gln Ser Ala Arg Ala Leu Gly Asn
                        245                 250                 255
        Leu Tyr Val Val Arg Tyr Arg Ser Glu Ala Asn Gly Asp Thr Gln Val
                        260                 265                 270
        Val Ala Ser Val Arg Ser Gly Ala Gly Arg Val Ser Asp Pro Phe
                        275                 280                 285
        Pro Val Thr Leu Pro Gly Val Pro Thr Pro Ser Val Val Ala Gly
                290                 295                 300
        Thr Val Asp Gly Phe Phe Thr Ser Ser Thr Gly Leu Val Ile Gly Leu
        305                 310                 315                 320
        Leu Ala Cys Tyr Ser Ala Leu Ala Gly Gly Val Leu Ala Val Ala Gly
                        325                 330                 335
        Arg Ala Pro Ala Arg Ile Ser Ala Ala Arg Arg Gly Arg Gln Asp Gly
                        340                 345                 350
        Arg Asp Ser Met Leu Ser Arg Phe Ala Glu Arg Leu Val Gln Trp Ile
                        355                 360                 365
        Asp Gln Asn Leu Arg Arg Gly Arg Ile Ala Ala Arg Thr Gln Ala
        370                 375                 380
        Leu Gln Glu Ala Gly Leu Lys Leu Arg Pro Gly Asp Phe Ile Ala Leu
        385                 390                 395                 400
        Val Gly Ala Ala Ala Ile Thr Ala Ala Ile Gly Leu Leu Ala Ser
                        405                 410                 415
        Gly Ile Val Ala Ala Leu Leu Leu Ala Ala Ile Thr Val Gly Leu Ser
                        420                 425                 430
        Arg Ile Tyr Leu Arg Val Met Ala Gly Arg Arg Ala Ala Phe Ala
                435                 440                 445
        Asp Gln Leu Asp Asp Ser Leu Gln Leu Leu Ala Ser Asn Leu Arg Ala
                450                 455                 460
        Gly His Ser Met Leu Arg Ala Leu Asp Ser Leu Ser Arg Glu Ala Glu
        465                 470                 475                 480
        Val Pro Thr Ser Glu Glu Phe Ala Arg Ile Val Asn Glu Thr Arg Val
                        485                 490                 495
        Gly Arg Asp Leu Asn Glu Ser Leu Asp Asp Val Ala Arg Arg Met Arg
                        500                 505                 510
        Ser Asp Asp Phe Asn Trp Ile Ala Gln Ala Ile Ala Ile Asn Arg Glu
                        515                 520                 525
        Val Gly Gly Asp Leu Ala Glu Val Leu Asp Gln Val Gly Asn Thr Ile
                530                 535                 540
        Arg Glu Arg Asn Gln Ile Arg Arg Gln Val Lys Ala Leu Ala Ala Glu
        545                 550                 555                 560
        Gly Lys Leu Ser Ala Tyr Val Leu Met Ala Leu Pro Phe Gly Leu Thr
                        565                 570                 575
        Ala Phe Leu Leu Val Ser Asn Pro Asp Tyr Leu Ser Lys Leu Thr Gly
                        580                 585                 590
        Ser Ala Ile Gly Tyr Val Met Ile Ala Val Gly Leu Val Met Leu Thr
                        595                 600                 605
        Val Gly Gly Leu Trp Met Asn Lys Val Val Ser Val Lys Phe
                610                 615                 620

<210> SEQ ID NO 20
<211> LENGTH: 296
<212> TYPE: PRT
<213> ORGANISM: Rhodococcus equi
```

<400> SEQUENCE: 20

```
Val Ile Pro Pro Leu Val Leu Met Ala Ala Leu Ser Val Gly Gly Ala
1               5                   10                  15
Leu Gly Val Leu Val Trp Leu Thr Val Gly Ala Arg Asp Pro Glu Arg
            20                  25                  30
Gly Pro Ala Leu Arg Asn Leu Gln Ser Gln Leu Ala Leu Pro Ile Pro
        35                  40                  45
Glu Ser Gly Gly Ala Pro Pro Leu Ser Leu Gly Arg Phe Val Lys Leu
50                  55                  60
Leu Ser Pro Pro Gly Thr Met Ala Arg Leu Glu Arg Leu His Ile Leu
65                  70                  75                  80
Ala Gly Arg Pro Ala Ala Trp Val Pro Glu Arg Ala Ala Met Ala Lys
                85                  90                  95
Ile Val Leu Ala Ala Ala Ala Leu Leu Gly Leu Leu Ala Val Gly
            100                 105                 110
Ala Ser Pro Gly Val Gly Arg Val Leu Phe Ala Ala Ala Val Ala
        115                 120                 125
Leu Ala Tyr Phe Val Pro Glu Leu Leu Leu Gln Ser Arg Gly Gln Glu
130                 135                 140
Arg Gln Ala Ala Ile Glu Leu Ala Leu Ala Asp Thr Leu Asp Gln Met
145                 150                 155                 160
Thr Ile Ala Val Glu Ala Gly Leu Gly Phe Glu Ala Ala Met Gln Arg
                165                 170                 175
Ala Ala Lys Asn Gly Lys Gly Pro Leu Ala Glu Glu Phe Ile Arg Thr
            180                 185                 190
Leu Gln Asp Ile Gln Met Gly Gln Ser Arg Arg Ile Ala Tyr Leu Asp
        195                 200                 205
Leu Ala Ala Arg Thr Lys Ala Pro Asn Leu Arg Arg Phe Leu Arg Ala
210                 215                 220
Val Ile Gln Ala Asp Glu Tyr Gly Val Ala Ile Ala Glu Val Leu Arg
225                 230                 235                 240
Thr Gln Ala Ser Glu Met Arg Leu Lys Arg Arg Gln Ser Ala Glu Glu
                245                 250                 255
Lys Ala Met Lys Val Pro Val Lys Val Leu Phe Pro Leu Met Thr Cys
            260                 265                 270
Ile Leu Pro Thr Ile Phe Ile Val Ile Leu Gly Pro Ala Val Ile Asn
        275                 280                 285
Met Met Glu Val Leu Gly Gly Met
    290                 295
```

<210> SEQ ID NO 21
<211> LENGTH: 262
<212> TYPE: PRT
<213> ORGANISM: Rhodococcus equi

<400> SEQUENCE: 21

```
Val Ile Val Ala Ala Gly Val Gly Ala Ala Leu Leu Gly Ile Leu Ala
1               5                   10                  15
Gly Ala Phe Ala Asn Ser Ala Ile Asp Arg Val Arg Leu Glu Thr Ala
            20                  25                  30
Cys Ala Glu Pro Lys Ser Thr Pro Thr Gly Ser Thr Pro Pro Pro
        35                  40                  45
Ser Pro Ala Ser Ala Val Ala Thr Arg Ile Ala Met Ile Asp Thr Ile
50                  55                  60
```

```
Thr Arg Arg Arg Asp Ile Ser Ala Arg Arg Met Leu Val Glu Leu Ala
 65                  70                  75                  80

Thr Ala Leu Leu Phe Val Ala Ile Thr Leu Arg Leu Ala Ala Leu Gly
                 85                  90                  95

Leu Leu Pro Ala Ala Pro Ala Tyr Leu Trp Phe Ala Val Ile Gly Ile
            100                 105                 110

Ala Leu Ala Val Ile Asp Ile Asp Cys Lys Arg Leu Pro Asn Phe Leu
            115                 120                 125

Val Val Pro Ser Tyr Pro Ile Val Phe Ala Cys Leu Ala Val Gly Ser
            130                 135                 140

Val Val Thr Gly Asp Trp Ser Ala Leu Leu Arg Ala Ala Ile Gly Ala
145                 150                 155                 160

Ala Val Leu Phe Gly Phe Tyr Phe Val Leu Ala Leu Ile Tyr Pro Ala
                165                 170                 175

Gly Met Gly Phe Gly Asp Val Lys Leu Ala Gly Val Ile Gly Ala Val
            180                 185                 190

Leu Ala Tyr Leu Ser Tyr Gly Thr Leu Leu Val Gly Ala Phe Leu Ala
            195                 200                 205

Phe Leu Val Ala Ala Leu Val Gly Leu Ile Ile Leu Val Thr Arg Arg
            210                 215                 220

Gly Arg Ile Gly Thr Thr Ile Pro Phe Gly Pro Tyr Met Ile Ala Ala
225                 230                 235                 240

Ala Val Val Ala Ile Leu Ala Ala Asp Pro Leu Ala Arg Ala Tyr Leu
                245                 250                 255

Asp Trp Ala Ala Ala Ala
            260

<210> SEQ ID NO 22
<211> LENGTH: 262
<212> TYPE: PRT
<213> ORGANISM: Rhodococcus equi

<400> SEQUENCE: 22

Val Ile Val Ala Ala Gly Val Gly Ala Ala Leu Leu Gly Ile Leu Ala
  1               5                  10                  15

Gly Ala Phe Ala Asn Ser Ala Ile Asp Arg Val Arg Leu Glu Thr Ala
                 20                  25                  30

Cys Ala Glu Pro Arg Ala Thr Pro Thr Gly Ser Thr Pro Pro Pro Pro
             35                  40                  45

Ser Pro Thr Ser Ala Val Ala Thr Arg Ile Ala Met Ile Asp Thr Ile
         50                  55                  60

Thr Arg Arg Arg Asp Ile Ser Ala Arg Arg Met Leu Val Glu Leu Ala
 65                  70                  75                  80

Thr Ala Leu Leu Phe Val Ala Ile Thr Leu Arg Leu Ala Ala Leu Asp
                 85                  90                  95

Leu Leu Pro Ala Ala Pro Ala Tyr Leu Trp Phe Ala Val Ile Gly Ile
            100                 105                 110

Ala Leu Ala Val Ile Asp Ile Asp Cys Lys Arg Leu Pro Asn Phe Leu
            115                 120                 125

Val Val Pro Ser Tyr Pro Ile Val Phe Ala Cys Leu Ala Val Gly Ser
            130                 135                 140

Val Val Thr Gly Asp Trp Ser Ala Leu Leu Arg Ala Ala Ile Gly Ala
145                 150                 155                 160

Ala Val Leu Phe Gly Phe Tyr Phe Val Leu Ala Leu Ile Tyr Pro Ala
```

```
            165                 170                 175
Gly Met Gly Phe Gly Asp Val Lys Leu Ala Gly Val Ile Gly Ala Val
            180                 185                 190

Leu Ala Tyr Leu Ser Tyr Gly Thr Leu Leu Val Gly Ala Phe Leu Ala
            195                 200                 205

Phe Leu Val Ala Ala Leu Val Gly Leu Ile Ile Leu Val Thr Arg Arg
            210                 215                 220

Gly Arg Ile Gly Thr Thr Ile Pro Phe Gly Pro Tyr Met Ile Ala Ala
225                 230                 235                 240

Ala Val Val Ala Ile Leu Ala Ala Asp Pro Leu Ala Arg Ala Tyr Leu
                245                 250                 255

Asp Trp Ala Ala Ala Ala
            260

<210> SEQ ID NO 23
<211> LENGTH: 262
<212> TYPE: PRT
<213> ORGANISM: Rhodococcus equi

<400> SEQUENCE: 23

Val Ile Val Ala Ala Gly Val Gly Ala Ala Leu Leu Gly Ile Leu Ala
1               5                   10                  15

Gly Ala Phe Ala Asn Ser Ala Ile Asp Arg Val Arg Leu Glu Thr Ala
            20                  25                  30

Cys Ala Glu Pro Lys Ser Thr Pro Ala Asn Ser Thr Pro Ser Pro
        35                  40                  45

Ser Pro Thr Ser Ala Val Ala Arg Ile Ala Met Ile Asp Thr Ile
50                  55                  60

Thr Arg Arg His Asp Ile Ser Ala Arg Arg Val Leu Val Glu Leu Ala
65                  70                  75                  80

Thr Ala Leu Leu Phe Val Ala Ile Thr Leu Arg Leu Ala Ala Leu Asp
                85                  90                  95

Leu Leu Pro Ala Ala Pro Ala Tyr Leu Trp Phe Ala Val Val Gly Ile
            100                 105                 110

Ala Leu Ala Val Ile Asp Ile Asp Cys Lys Arg Leu Pro Asn Phe Leu
            115                 120                 125

Val Val Pro Ser Tyr Pro Ile Val Phe Ala Cys Leu Ala Val Gly Ser
        130                 135                 140

Val Val Thr Gly Asp Trp Ser Ala Leu Leu Arg Ala Ala Ile Gly Ala
145                 150                 155                 160

Ala Val Leu Phe Gly Phe Tyr Phe Val Leu Ala Leu Ile Tyr Pro Ala
                165                 170                 175

Gly Met Gly Phe Gly Asp Val Lys Leu Ala Gly Val Ile Gly Ala Val
            180                 185                 190

Leu Ala Tyr Leu Ser Tyr Gly Thr Leu Leu Val Gly Ala Phe Leu Ala
            195                 200                 205

Phe Leu Val Ala Ala Leu Val Gly Leu Ile Ile Leu Val Thr Arg Arg
            210                 215                 220

Gly Arg Ile Gly Thr Thr Ile Pro Phe Gly Pro Tyr Met Ile Ala Ala
225                 230                 235                 240

Ala Val Val Ala Ile Leu Ala Ala Asp Pro Leu Ala Arg Ala Tyr Leu
                245                 250                 255

Asp Trp Ala Ala Ala Ala
            260
```

<210> SEQ ID NO 24
<211> LENGTH: 70
<212> TYPE: PRT
<213> ORGANISM: Rhodococcus equi

<400> SEQUENCE: 24

Met Asn Leu Phe Phe Ala Asn Leu Tyr Leu Met Gly Leu Asp Val Lys
1               5                   10                  15

Asp Arg Leu Thr Arg Asp Asp Arg Gly Ala Thr Ala Val Glu Tyr Gly
                20                  25                  30

Leu Met Val Ala Gly Ile Ala Met Val Ile Leu Ile Ala Val Phe Ala
            35                  40                  45

Phe Gly Gly Lys Ile Ser Glu Leu Phe Ser Gly Phe Asn Phe Asp Lys
        50                  55                  60

Pro Ala Ala Ser Gly Thr
65                  70

<210> SEQ ID NO 25
<211> LENGTH: 67
<212> TYPE: PRT
<213> ORGANISM: Rhodococcus equi

<400> SEQUENCE: 25

Met Asn Leu Phe Phe Ala Asn Leu Tyr Leu Met Gly Leu Asp Val Lys
1               5                   10                  15

Asp Arg Leu Thr Arg Asp Asp Arg Gly Ala Thr Ala Val Glu Tyr Gly
                20                  25                  30

Leu Met Val Ala Gly Ile Ala Met Val Ile Ile Ile Ala Val Phe Ala
            35                  40                  45

Phe Gly Gly Arg Leu Ser Thr Leu Phe Gln Asn Phe Asn Phe Ala Asn
        50                  55                  60

Pro Gly Asn
65

<210> SEQ ID NO 26
<211> LENGTH: 63
<212> TYPE: PRT
<213> ORGANISM: Artificial Sequence
<220> FEATURE:
<223> OTHER INFORMATION: Consensus amino acid sequence of amino acid
      sequence alignment of SEQ ID NO 24 and SEQ ID NO 25

<400> SEQUENCE: 26

Met Asn Leu Phe Phe Ala Asn Leu Tyr Leu Met Gly Leu Asp Val Lys
1               5                   10                  15

Asp Arg Leu Thr Arg Asp Asp Arg Gly Ala Thr Ala Val Glu Tyr Gly
                20                  25                  30

Leu Met Val Ala Gly Ile Ala Met Val Ile Ile Ile Ala Val Phe Ala
            35                  40                  45

Phe Gly Gly Lys Ile Ser Leu Phe Gly Phe Asn Phe Asp Pro Gly
        50                  55                  60

<210> SEQ ID NO 27
<211> LENGTH: 135
<212> TYPE: PRT
<213> ORGANISM: Rhodococcus equi

<400> SEQUENCE: 27

Val Ile Met Lys Arg Leu Thr Ser Asp Ser Gly Val Ala Ala Val Glu
1               5                   10                  15

```
Phe Ala Leu Val Val Pro Ile Leu Ile Thr Leu Val Leu Gly Ile Val
            20                  25                  30

Glu Phe Gly Arg Gly Tyr Asn Val Gln Asn Ala Val Ser Ala Ala Ala
        35                  40                  45

Arg Glu Gly Ala Arg Thr Met Ala Ile Lys Lys Asp Pro Ala Ala Ala
65      50                  55                  60

Arg Ala Ala Val Lys Gly Ala Val Phe Ser Pro Ala Ile Thr Asp
65              70                  75                  80

Ala Glu Ile Cys Ile Ser Thr Ser Gly Ser Gln Gly Cys Ser Ala Thr
                85                  90                  95

Ser Cys Pro Ser Gly Ser Thr Val Thr Leu Thr Val Ser Tyr Pro Leu
            100                 105                 110

Glu Tyr Met Thr Gly Leu Phe Pro Gly Lys Pro Thr Leu Thr Gly Thr
            115                 120                 125

Gly Val Met Arg Cys Gly Gly
        130             135

<210> SEQ ID NO 28
<211> LENGTH: 130
<212> TYPE: PRT
<213> ORGANISM: Rhodococcus equi

<400> SEQUENCE: 28

Leu Arg Ser Asp Ser Gly Val Ala Ala Val Glu Phe Ala Leu Val Val
1               5                   10                  15

Pro Ile Leu Ile Thr Leu Val Leu Gly Ile Val Glu Phe Gly Arg Gly
            20                  25                  30

Tyr Asn Val Gln Asn Ala Val Ser Ala Ala Ala Arg Glu Gly Ala Arg
        35                  40                  45

Thr Met Ala Ile Lys Lys Asp Pro Ala Ala Ala Arg Ala Ala Val Lys
    50                  55                  60

Gly Ala Gly Val Phe Ser Pro Ala Ile Thr Asp Ala Glu Ile Cys Ile
65              70                  75                  80

Ser Thr Ser Gly Thr Gln Gly Cys Ser Ala Thr Ser Cys Pro Ser Gly
                85                  90                  95

Ser Thr Val Thr Leu Thr Val Ser Tyr Pro Leu Glu Tyr Met Thr Gly
            100                 105                 110

Leu Phe Pro Gly Lys Pro Thr Leu Thr Gly Thr Gly Val Met Arg Cys
            115                 120                 125

Gly Gly
    130

<210> SEQ ID NO 29
<211> LENGTH: 135
<212> TYPE: PRT
<213> ORGANISM: Rhodococcus equi

<400> SEQUENCE: 29

Met Gly Met Arg Arg Phe Gly Ser Asp Ser Gly Ala Ala Ala Val Glu
1               5                   10                  15

Phe Ala Leu Val Val Pro Ile Leu Ile Thr Leu Val Leu Gly Ile Val
            20                  25                  30

Glu Phe Gly Arg Gly Tyr Asn Val Gln Asn Ala Val Ser Ala Ala Ala
        35                  40                  45

Arg Glu Gly Ala Arg Thr Met Ala Ile Lys Lys Asp Pro Ala Ala Ala
    50                  55                  60
```

```
Arg Ala Ala Val Lys Gly Ala Gly Val Phe Ser Pro Ala Ile Thr Asp
 65                  70                  75                  80

Ala Glu Ile Cys Ile Ser Thr Ser Gly Thr Gln Gly Cys Ser Ala Thr
                 85                  90                  95

Ser Cys Pro Ser Gly Ser Thr Val Thr Leu Thr Val Ser Tyr Pro Leu
            100                 105                 110

Glu Tyr Met Thr Gly Leu Phe Pro Gly Lys Pro Thr Leu Thr Gly Thr
            115                 120                 125

Gly Val Met Arg Cys Gly Gly
            130             135

<210> SEQ ID NO 30
<211> LENGTH: 321
<212> TYPE: PRT
<213> ORGANISM: Rhodococcus equi

<400> SEQUENCE: 30

Met Arg Trp Val Arg Ser Arg Met Ser Asn Asp Glu Arg Gly Val Val
  1               5                  10                  15

Ala Val Leu Val Ala Ile Leu Met Val Val Leu Leu Gly Cys Ala Ala
                 20                  25                  30

Ile Ser Val Asp Ile Gly Ala Asn Tyr Val Val Lys Arg Gln Leu Gln
             35                  40                  45

Asn Gly Ala Asp Ala Ala Ala Leu Ala Val Ala Gln Glu Ser Ser Cys
 50                  55                  60

Lys Ala Gly Ser Ser Ala Ser Ser Val Ser Ser Leu Val Gln Ala Asn
 65                  70                  75                  80

Val Asn Ser Ser Ala Ser Ser Ala Ala Val Ile Asp Gly Val Lys
                 85                  90                  95

Arg Lys Val Thr Val Thr Ala Ser Ala Val Gly Asp Asp Gly Leu Ala
            100                 105                 110

Gly Arg Arg Asn Val Phe Ala Pro Val Leu Gly Val Asp Arg Ser Glu
            115                 120                 125

Ile Ser Ala Ser Ala Thr Ala Ser Cys Val Phe Pro Leu Gly Gly Thr
130                 135                 140

Ala Glu Leu Pro Leu Thr Phe His Lys Cys His Phe Asp Glu Ser Arg
145                 150                 155                 160

Ser Leu Asp Val Lys Ile Leu Val Ala Tyr Asn Val Thr Ala Pro Arg
                165                 170                 175

Cys Asn Gly Thr Ser Gly Asn Ala Ala Pro Gly Asn Phe Gly Trp Leu
            180                 185                 190

Gln Gly Ala Asn Gly Arg Cys Pro Ala Lys Ile Asp Ala Ala Val Tyr
            195                 200                 205

Ala Thr Pro Gly Asp Thr Gly Asn Asn Ile Pro Gly Pro Cys Lys Asp
            210                 215                 220

Thr Ile Lys Gln Phe Gln Asn Ala Val Val Arg Val Pro Ile Tyr Asp
225                 230                 235                 240

Val Ala Gly Gly Thr Gly Ser Gly Gly Trp Phe His Val Val Gly Leu
                245                 250                 255

Ala Ala Phe Lys Ile Gln Gly Tyr Arg Leu Ser Gly Asn Pro Glu Phe
            260                 265                 270

Asn Trp Asn Asn Asp Val His Gly Ala Leu Ser Cys Thr Gly Ser Cys
            275                 280                 285

Arg Gly Ile Ile Gly Thr Phe Val Lys Ile Val Ser Leu Asp Ser Asp
```

```
              290                 295                 300
Leu Thr Pro Gly Gly Ile Asp Phe Gly Val Ser Thr Ile Ser Leu Leu
305                 310                 315                 320

Asp

<210> SEQ ID NO 31
<211> LENGTH: 321
<212> TYPE: PRT
<213> ORGANISM: Rhodococcus equi

<400> SEQUENCE: 31

Met Arg Trp Val Arg Ser Arg Met Ser Asn Asp Glu Arg Gly Val Val
1               5                   10                  15

Ala Val Leu Val Ala Ile Leu Met Val Val Leu Leu Gly Cys Ala Ala
                20                  25                  30

Ile Ser Val Asp Ile Gly Ala Asn Tyr Val Val Lys Arg Gln Leu Gln
            35                  40                  45

Asn Gly Ala Asp Ala Ala Ala Leu Ala Val Ala Gln Glu Ser Asn Cys
        50                  55                  60

Lys Ala Gly Ser Ser Ala Ser Ser Val Ser Ser Leu Val Gln Ala Asn
65                  70                  75                  80

Val Asn Ser Ser Ala Ser Ser Ala Ala Val Ile Asp Gly Val Lys
                85                  90                  95

Arg Lys Val Thr Val Thr Ala Ser Ala Val Gly Asp Asp Gly Leu Ala
                100                 105                 110

Gly Arg Arg Asn Val Phe Ala Pro Val Leu Gly Val Asp Arg Ser Glu
            115                 120                 125

Ile Ser Ala Ser Ala Thr Ala Ser Cys Val Phe Pro Leu Gly Gly Thr
        130                 135                 140

Ala Glu Leu Pro Leu Thr Phe His Lys Cys His Phe Asp Glu Ser Arg
145                 150                 155                 160

Ser Leu Asp Val Lys Ile Leu Val Ala Tyr Asn Val Thr Ala Pro Arg
                165                 170                 175

Cys Asn Gly Thr Ser Gly Asn Ala Ala Pro Gly Asn Phe Gly Trp Leu
            180                 185                 190

Gln Gly Ala Asn Gly Arg Cys Pro Ala Lys Ile Asp Pro Thr Val Tyr
        195                 200                 205

Ala Thr Pro Gly Asp Thr Gly Asn Asn Ile Pro Gly Pro Cys Lys Asp
    210                 215                 220

Thr Ile Lys Gln Phe Gln Asn Ala Val Val Arg Val Pro Ile Tyr Asp
225                 230                 235                 240

Val Ala Gly Gly Thr Gly Ser Gly Gly Trp Phe His Val Val Gly Leu
                245                 250                 255

Ala Ala Phe Lys Ile Gln Gly Tyr Arg Leu Ser Gly Asn Pro Glu Phe
            260                 265                 270

Asn Trp Asn Asn Asp Val His Gly Ala Leu Ser Cys Thr Gly Ser Cys
        275                 280                 285

Arg Gly Ile Ile Gly Thr Phe Val Lys Ile Val Ser Leu Asp Ser Asp
    290                 295                 300

Leu Thr Pro Gly Gly Ile Asp Phe Gly Val Ser Thr Ile Ser Leu Leu
305                 310                 315                 320

Asp

<210> SEQ ID NO 32
```

```
<211> LENGTH: 321
<212> TYPE: PRT
<213> ORGANISM: Rhodococcus equi

<400> SEQUENCE: 32

Met Arg Trp Val Arg Ser Arg Met Ser Asn Asp Glu Arg Gly Val Val
1               5                   10                  15

Ala Val Phe Val Ala Ile Leu Met Val Val Leu Leu Gly Cys Ala Ala
            20                  25                  30

Ile Ser Val Asp Ile Gly Ala Asn Tyr Val Val Lys Arg Gln Leu Gln
        35                  40                  45

Asn Gly Ala Asp Ala Ala Leu Ala Val Ala Gln Glu Ser Ser Cys
    50                  55                  60

Lys Ala Gly Ser Ser Ala Ser Ser Val Ser Arg Leu Val Gln Ala Asn
65                  70                  75                  80

Val Asn Ser Ser Ser Ala Ser Ser Ala Ala Val Ile Asp Gly Val Lys
                85                  90                  95

Arg Lys Val Thr Val Thr Ala Ser Ala Val Gly Asp Asp Gly Leu Ala
            100                 105                 110

Gly Arg Arg Asn Val Phe Ala Pro Val Leu Gly Val Asp Arg Ser Glu
        115                 120                 125

Ile Ser Ala Ser Ala Thr Ala Ser Cys Val Phe Pro Leu Gly Thr
130                 135                 140

Ala Glu Leu Pro Leu Thr Phe His Lys Cys His Phe Asp Glu Ser Arg
145                 150                 155                 160

Ser Leu Asp Val Lys Ile Leu Val Ala Tyr Asn Val Thr Ala Pro Arg
                165                 170                 175

Cys Asn Gly Thr Ser Gly Asn Ala Ala Pro Gly Asn Phe Gly Trp Leu
            180                 185                 190

Gln Gly Val Asn Gly Arg Cys Pro Ala Lys Ile Asp Ala Ala Val Tyr
        195                 200                 205

Ala Thr Pro Gly Asp Thr Gly Asn Asn Ile Pro Gly Pro Cys Lys Asp
    210                 215                 220

Thr Ile Lys Gln Phe Gln Asn Ala Val Val Arg Val Pro Ile Tyr Asp
225                 230                 235                 240

Val Ala Gly Gly Thr Gly Ser Gly Gly Trp Phe His Val Val Gly Leu
                245                 250                 255

Ala Ala Phe Lys Ile Gln Gly Tyr Arg Leu Ser Gly Asn Pro Glu Phe
            260                 265                 270

Asn Trp Asn Asn Asp Val His Gly Ala Leu Ser Cys Thr Gly Ser Cys
        275                 280                 285

Arg Gly Ile Ile Gly Thr Phe Val Lys Ile Val Ser Leu Asp Ser Asp
    290                 295                 300

Leu Thr Pro Gly Gly Ile Asp Phe Gly Val Ser Thr Ile Ser Leu Leu
305                 310                 315                 320

Asp

<210> SEQ ID NO 33
<211> LENGTH: 245
<212> TYPE: PRT
<213> ORGANISM: Rhodococcus equi

<400> SEQUENCE: 33

Leu Arg Thr Arg Ile Ile Ala Ala Ile Cys Ala Ile Val Leu Ala Val
1               5                   10                  15
```

```
Ala Gly Thr Leu Ala Leu Ile Ser Tyr Val Arg Gly Ala Asp Ala Arg
            20                  25                  30

Ala Leu Ala Gly Thr Arg Thr Val Asp Val Leu Val Ala Asp Gln Thr
        35                  40                  45

Ile Pro Lys Asn Thr Pro Ala Asp Ser Leu Val Gly Met Val Val Val
 50                  55                  60

Lys Lys Leu Pro Glu Met Ala Val Leu Pro Glu Arg Val Thr Ser Leu
 65                  70                  75                  80

Asp Gln Leu Ser Gly Lys Val Ala Leu Thr Asp Leu Leu Pro Gly Glu
                85                  90                  95

Gln Leu Val Ser Ala Arg Phe Ala Asp Pro Ala Thr Ala Arg Ser Gln
            100                 105                 110

Asp Gln Gly Gly Ile Pro Glu Gly Met Gln Glu Val Thr Val Leu Leu
        115                 120                 125

Glu Pro Gln Arg Ala Leu Gly Gly His Ile Ala Ser Gly Asp Thr Val
130                 135                 140

Gly Val Phe Met Ser Phe Ser Pro Pro Val Lys Asn Tyr Glu Thr His
145                 150                 155                 160

Leu Arg Leu Gln Lys Val Arg Val Thr Arg Val Gln Gly Thr Phe Ser
                165                 170                 175

Asn Ala Asp Glu Gly Asp Ser Ala Thr Val Asp Ser Ser Pro Ser Pro
            180                 185                 190

Ala Pro Thr Glu Ala Phe Leu Val Ser Leu Ala Val Asp Val Pro Met
        195                 200                 205

Ala Glu Arg Val Val Phe Ala Ala Glu His Gly Thr Ile Trp Leu Ser
210                 215                 220

Asn Glu Pro Leu Ser Ser Asn Glu Ala Gly Ala Ser Val Val Ser Pro
225                 230                 235                 240

Glu Gly Val Phe Arg
                245

<210> SEQ ID NO 34
<211> LENGTH: 245
<212> TYPE: PRT
<213> ORGANISM: Rhodococcus equi

<400> SEQUENCE: 34

Leu Arg Thr Arg Ile Ile Ala Ala Ile Cys Ala Ile Val Leu Ala Val
1               5                   10                  15

Ala Gly Thr Leu Ala Leu Ile Ser Tyr Val Arg Gly Ala Asp Ala Arg
            20                  25                  30

Ala Leu Ala Gly Thr Arg Thr Val Asp Val Leu Val Ala Asp Gln Thr
        35                  40                  45

Ile Pro Lys Asn Thr Pro Ala Asp Ser Leu Val Gly Met Val Val Val
 50                  55                  60

Lys Lys Leu Pro Glu Met Ala Val Leu Pro Glu Arg Val Thr Ser Leu
 65                  70                  75                  80

Asp Gln Leu Ser Gly Lys Val Ala Leu Thr Asp Leu Leu Pro Gly Glu
                85                  90                  95

Gln Leu Val Ser Ala Arg Phe Ala Asp Pro Ala Thr Ala Arg Ser Gln
            100                 105                 110

Asp Gln Gly Gly Ile Pro Glu Gly Met Gln Glu Val Thr Val Leu Leu
        115                 120                 125

Glu Pro Gln Arg Ala Leu Gly Gly His Ile Ala Pro Gly Asp Thr Val
130                 135                 140
```

Gly Val Phe Met Ser Phe Ser Pro Pro Val Lys Asn Tyr Glu Thr His
145                 150                 155                 160

Leu Arg Leu Gln Lys Val Arg Val Thr Arg Val Gln Gly Thr Phe Ser
            165                 170                 175

Asn Ala Asp Glu Gly Asp Ser Ala Thr Val Asp Ser Ser Pro Ser Pro
        180                 185                 190

Ala Pro Thr Glu Ala Phe Leu Val Ser Leu Ala Val Asp Val Pro Met
    195                 200                 205

Ala Glu Arg Val Val Phe Ala Ala Glu His Gly Thr Ile Trp Leu Ser
210                 215                 220

Asn Glu Pro Leu Ser Ser Asn Glu Ala Gly Ala Ser Val Val Ser Pro
225                 230                 235                 240

Glu Gly Val Phe Arg
            245

<210> SEQ ID NO 35
<211> LENGTH: 245
<212> TYPE: PRT
<213> ORGANISM: Rhodococcus equi

<400> SEQUENCE: 35

Leu Arg Thr Arg Ile Ile Ala Ala Ile Cys Ala Ile Val Leu Ala Val
1               5                   10                  15

Ala Gly Thr Leu Ala Leu Ile Ser Tyr Val Arg Gly Ala Asp Ala Arg
            20                  25                  30

Ala Leu Ala Gly Thr Arg Thr Val Asp Val Leu Val Ala Asp Gln Thr
        35                  40                  45

Ile Pro Lys Asn Thr Pro Ala Asp Ser Leu Val Gly Met Val Val Val
50                  55                  60

Lys Lys Leu Pro Glu Met Ala Val Leu Pro Asp Arg Val Thr Ser Leu
65                  70                  75                  80

Asp Gln Leu Ser Gly Lys Val Ala Leu Thr Asp Leu Leu Pro Gly Glu
            85                  90                  95

Gln Leu Val Ser Ala Arg Phe Val Asp Pro Ala Thr Ala Arg Ser Gln
        100                 105                 110

Asp Gln Gly Gly Ile Pro Glu Gly Met Gln Glu Val Thr Val Leu Leu
    115                 120                 125

Glu Pro Gln Arg Ala Leu Gly Gly His Ile Ala Ser Gly Asp Thr Val
    130                 135                 140

Gly Val Phe Met Ser Phe Ser Pro Pro Val Lys Asn Tyr Glu Thr His
145                 150                 155                 160

Leu Arg Leu Gln Lys Val Arg Val Thr Arg Val Gln Gly Thr Phe Ser
            165                 170                 175

Asn Ala Asp Glu Gly Asp Ser Ala Thr Val Asp Ser Ser Pro Ser Pro
        180                 185                 190

Ala Pro Thr Glu Ala Phe Leu Val Ser Leu Ala Val Asp Val Pro Met
    195                 200                 205

Ala Glu Arg Val Val Phe Ala Ala Glu His Gly Thr Ile Trp Leu Ser
210                 215                 220

Asn Glu Pro Leu Ser Ser Asn Glu Ala Gly Ala Ser Val Val Ser Pro
225                 230                 235                 240

Glu Gly Val Phe Arg
            245

<210> SEQ ID NO 36
<211> LENGTH: 399
<212> TYPE: PRT
<213> ORGANISM: Rhodococcus equi

<400> SEQUENCE: 36

| Met | Ser | Arg | Ile | Val | Leu | Leu | Thr | Asp | Arg | Asp | Phe | Ala | Arg | Arg |
| 1 | | | | 5 | | | | | 10 | | | | | 15 |

| Val | Tyr | His | Ala | Ala | Asp | Gly | Asn | Leu | Leu | Val | Leu | Pro | Ala | Gln | Pro |
| | | | 20 | | | | | 25 | | | | | 30 | | |

| Val | Pro | Arg | Gly | Pro | Ala | Gln | Leu | Val | Gly | Leu | Gly | Val | Thr | Val | Gln |
| | | 35 | | | | | 40 | | | | | 45 | | | |

| Pro | Glu | Val | Leu | Val | Leu | Gly | Pro | Asp | Val | Pro | Glu | Val | Glu | Gly | Leu |
| | 50 | | | | | 55 | | | | | 60 | | | | |

Ser Leu Ala Gly Arg Ile Asp His Ser Thr Pro Gly Thr Thr Val Val
65                  70                  75                  80

Leu Ala Ser Asp Ala Gly Thr Asp Val Trp Leu Arg Ala Met Arg Ala
                85                  90                  95

Gly Val Arg Asp Val Met Ser Pro Glu Ala Glu Ile Ala Asp Val Arg
            100                 105                 110

Ala Val Leu Asp Arg Ala Gly Gln Ala Ala Leu Ala Arg Arg Gln Gly
            115                 120                 125

Ala Ser Ala Pro Ala Glu Gln His Ala Val Gln Gly Lys Val Ile Val
        130                 135                 140

Val Ala Ser Pro Lys Gly Gly Thr Gly Lys Thr Thr Val Ala Thr Asn
145                 150                 155                 160

Leu Ala Val Gly Leu Ala Ala Ala Pro His Ser Thr Val Leu Val
                165                 170                 175

Asp Leu Asp Val Gln Phe Gly Asp Val Ala Ser Ala Leu Gln Leu Val
            180                 185                 190

Pro Glu His Cys Leu Thr Asp Ala Val Ala Gly Pro Ala Ser Gln Asp
        195                 200                 205

Met Ile Val Leu Lys Thr Val Leu Thr Pro His Ser Thr Gly Leu His
    210                 215                 220

Ala Leu Cys Gly Ser Asp Ser Pro Ala Ala Gly Asp Ser Ile Thr Gly
225                 230                 235                 240

Glu Gln Val Ser Thr Leu Leu Thr Gln Leu Ala Ala Glu Phe Arg Tyr
                245                 250                 255

Val Val Val Asp Thr Ala Pro Gly Leu Leu Glu His Thr Leu Ala Ala
            260                 265                 270

Leu Asp Leu Ala Thr Asp Val Leu Val Ser Gly Met Asp Val Pro
        275                 280                 285

Ser Val Arg Gly Met His Lys Glu Leu Gln Leu Leu Ala Glu Leu Asn
    290                 295                 300

Leu Gly Pro Val Val Arg His Val Val Leu Asn Phe Ala Asp Arg Arg
305                 310                 315                 320

Glu Gly Leu Thr Val Gln Asp Ile Gln Asn Thr Ile Gly Val Pro Ala
                325                 330                 335

Asp Ile Val Ile Lys Arg Ser Lys Ala Val Ala Leu Ser Thr Asn Arg
            340                 345                 350

Gly Val Pro Leu Leu Gln Asn Pro Gly Arg Asp Arg Thr Ala Lys Glu
        355                 360                 365

Leu Trp Arg Leu Val Gly Arg Ile Asp Pro Ala Pro Asp Thr Thr Lys
    370                 375                 380

Gly Gly Arg Ala Arg His Arg Ala Ala Glu Ala Val Gly Ala Lys
385                 390                 395

<210> SEQ ID NO 37
<211> LENGTH: 398
<212> TYPE: PRT
<213> ORGANISM: Rhodococcus equi

<400> SEQUENCE: 37

Met Ser Arg Ile Val Leu Leu Thr Asp Arg Asp Ala Arg Arg Val
1               5                   10                  15

Tyr His Ala Ala Asp Gly Asn Leu Leu Val Leu Pro Ala Gln Pro Val
                20                  25                  30

Pro Arg Gly Pro Ala Gln Leu Val Gly Leu Gly Val Thr Val Gln Pro
            35                  40                  45

Asp Val Leu Val Leu Gly Pro Asp Val Pro Glu Val Glu Gly Leu Ser
50                  55                  60

Leu Ala Gly Arg Ile Asp His Ser Thr Pro Gly Thr Thr Val Val Leu
65                  70                  75                  80

Ala Ser Asp Ala Gly Thr Asp Val Trp Leu Arg Ala Met Arg Ala Gly
                85                  90                  95

Val Arg Asp Val Met Ser Pro Glu Ala Glu Ile Ala Asp Val Arg Ala
            100                 105                 110

Val Leu Asp Arg Ala Gly Gln Ala Ala Leu Ala Arg Arg Gln Gly Ala
        115                 120                 125

Ser Ala Pro Ala Glu Gln His Ala Val Gln Gly Lys Val Ile Val Val
130                 135                 140

Ala Ser Pro Lys Gly Gly Thr Gly Lys Thr Thr Val Ala Thr Asn Leu
145                 150                 155                 160

Ala Val Gly Leu Ala Ala Ala Pro His Ser Thr Val Leu Val Asp
                165                 170                 175

Leu Asp Val Gln Phe Gly Asp Val Ala Ser Ala Leu Gln Leu Val Pro
            180                 185                 190

Glu His Cys Leu Thr Asp Ala Val Ala Ser Pro Ala Ser Gln Asp Met
        195                 200                 205

Ile Val Leu Lys Thr Val Leu Thr Pro His Ser Thr Gly Leu His Ala
    210                 215                 220

Leu Cys Gly Ser Asp Ser Pro Ala Ala Gly Asp Ser Ile Thr Gly Glu
225                 230                 235                 240

Gln Val Ser Thr Leu Leu Thr Gln Leu Ala Ala Glu Phe Arg Tyr Val
                245                 250                 255

Val Val Asp Thr Ala Pro Gly Leu Leu Glu His Thr Leu Ala Ala Leu
            260                 265                 270

Asp Leu Ala Thr Asp Val Val Leu Val Ser Gly Met Asp Val Pro Ser
        275                 280                 285

Val Arg Gly Met His Lys Glu Leu Gln Leu Leu Thr Glu Leu Asn Leu
    290                 295                 300

Gly Pro Val Val Arg His Val Val Leu Asn Phe Ala Asp Arg Arg Glu
305                 310                 315                 320

Gly Leu Thr Val Gln Asp Ile Gln Asn Thr Ile Gly Val Pro Ala Asp
                325                 330                 335

Ile Val Ile Lys Arg Ser Lys Ala Val Ala Leu Ser Thr Asn Arg Gly
            340                 345                 350

Val Pro Leu Leu Gln Asn Pro Gly Arg Asp Arg Thr Ala Lys Glu Leu
        355                 360                 365

Trp Arg Leu Val Gly Arg Ile Asp Pro Ala Pro Asp Thr Ala Lys Gly
            370                 375                 380

Gly Arg Ala Arg His Arg Ala Ala Glu Ala Val Gly Ala Lys
385                 390                 395

<210> SEQ ID NO 38
<211> LENGTH: 399
<212> TYPE: PRT
<213> ORGANISM: Rhodococcus equi

<400> SEQUENCE: 38

Met Ser Arg Ile Val Leu Leu Thr Asp Arg Asp Phe Ala Arg Arg
1               5                   10                  15

Val Tyr His Ala Ala Asp Gly Asn Leu Leu Val Leu Pro Ala Gln Pro
                20                  25                  30

Val Pro Arg Gly Pro Ala Gln Leu Val Gly Leu Gly Val Thr Val Gln
            35                  40                  45

Pro Asp Val Leu Val Leu Gly Pro Asp Val Pro Glu Val Glu Gly Leu
    50                  55                  60

Ser Leu Ala Gly Arg Ile Asp His Ser Thr Pro Gly Thr Thr Val Val
65                  70                  75                  80

Leu Ala Ser Asp Ala Gly Thr Asp Val Trp Leu Arg Ala Met Arg Ala
                85                  90                  95

Gly Val Arg Asp Val Met Ser Pro Glu Ala Glu Ile Ala Asp Val Arg
            100                 105                 110

Ala Val Leu Asp Arg Ala Gly Gln Ala Ala Leu Ala Arg Arg Gln Gly
        115                 120                 125

Ala Ser Ala Pro Ala Glu Gln His Ala Val Gln Gly Lys Val Ile Val
    130                 135                 140

Val Ala Ser Pro Lys Gly Gly Thr Gly Lys Thr Thr Val Ala Thr Asn
145                 150                 155                 160

Leu Ala Val Gly Leu Ala Ala Ala Pro His Ser Thr Val Leu Val
                165                 170                 175

Asp Leu Asp Val Gln Phe Gly Asp Val Ala Ser Ala Leu Gln Leu Val
            180                 185                 190

Pro Glu His Cys Leu Thr Asp Ala Val Ala Ser Pro Ala Ser Gln Asp
        195                 200                 205

Met Ile Val Leu Lys Thr Val Leu Thr Pro His Ser Thr Gly Leu His
    210                 215                 220

Ala Leu Cys Gly Ser Asp Ser Pro Ala Ala Gly Asp Ser Ile Thr Gly
225                 230                 235                 240

Glu Gln Val Ser Thr Leu Leu Thr Gln Leu Ala Ala Glu Phe Arg Tyr
                245                 250                 255

Val Val Val Asp Thr Ala Pro Gly Leu Leu Glu His Thr Leu Ala Ala
            260                 265                 270

Leu Asp Leu Ala Thr Asp Val Val Leu Ser Gly Met Asp Val Pro
        275                 280                 285

Ser Val Arg Gly Met His Lys Glu Leu Gln Leu Leu Thr Glu Leu Asn
    290                 295                 300

Leu Gly Pro Val Val Arg His Val Val Leu Asn Phe Ala Asp Arg Arg
305                 310                 315                 320

Glu Gly Leu Thr Val Gln Asp Ile Gln Asn Thr Ile Gly Val Pro Ala
                325                 330                 335

Asp Ile Val Ile Lys Arg Ser Lys Ala Val Ala Leu Ser Thr Asn Arg

```
                340               345               350
Gly Val Pro Leu Leu Gln Asn Pro Gly Arg Asp Arg Thr Ala Lys Glu
            355                 360                 365

Leu Trp Arg Leu Val Gly Arg Ile Asp Pro Ala Pro Asp Thr Ala Lys
        370                 375                 380

Gly Gly Arg Ala Arg His Arg Ala Ala Glu Ala Val Gly Ala Lys
385                 390                 395

<210> SEQ ID NO 39
<211> LENGTH: 465
<212> TYPE: PRT
<213> ORGANISM: Rhodococcus equi

<400> SEQUENCE: 39

Met Arg Leu Ser Gln Arg Leu Glu Ala Val Arg Gly Ala Ala Pro Val
1               5                   10                  15

Glu Ala Ala Pro Ile Pro Gly Lys Gln Gly Lys Ala Lys Thr
            20                  25                  30

Ser Leu Pro Pro Ala Asp Ala Leu Ala Glu Leu Lys Asp Arg Ala Ser
        35                  40                  45

Ala Ala Leu Tyr Thr Arg Ile Gly Thr Arg Phe Asn Asp Ser Ser Leu
    50                  55                  60

Ser Glu Glu Gln Leu His Leu Val Arg Glu Glu Leu Ala Glu Ile
65                  70                  75                  80

Val Glu Gln Glu Thr Thr Pro Leu Thr Phe Asp Glu Arg Gln Arg Leu
                85                  90                  95

Leu Arg Glu Val Ala Asp Glu Val Leu Gly His Gly Pro Leu Gln Arg
            100                 105                 110

Leu Leu Glu Asp Pro Ser Val Thr Glu Ile Met Val Asn Ser His Asp
        115                 120                 125

Met Val Tyr Val Glu Arg Asp Gly Thr Leu Val Arg Ser Ser Ala Arg
    130                 135                 140

Phe Ala Asp Glu Ala His Leu Arg Arg Val Ile Glu Arg Ile Val Ser
145                 150                 155                 160

Ala Val Gly Arg Arg Ile Asp Glu Ser Ser Pro Leu Val Asp Ala Arg
                165                 170                 175

Leu Ala Asp Gly Ser Arg Val Asn Ala Val Ile Pro Pro Leu Ala Phe
            180                 185                 190

Asn Gly Ser Ser Leu Thr Ile Arg Lys Phe Ser Lys Asp Pro Phe Gln
        195                 200                 205

Val Asp Asp Leu Ile Ala Phe Gly Thr Leu Ser His Glu Met Ala Glu
    210                 215                 220

Leu Leu Asp Ala Cys Val Gln Ala Arg Leu Asn Val Ile Val Ser Gly
225                 230                 235                 240

Gly Thr Gly Thr Gly Lys Thr Thr Leu Leu Asn Val Leu Ser Ser Phe
                245                 250                 255

Ile Pro Glu Gly Glu Arg Ile Val Thr Ile Glu Asp Ala Val Glu Leu
            260                 265                 270

Gln Leu Gln Gln Asp His Val Val Arg Leu Glu Ser Arg Pro Pro Asn
        275                 280                 285

Ile Glu Gly Lys Gly Ala Val Thr Ile Arg Asp Leu Val Arg Asn Ser
    290                 295                 300

Leu Arg Met Arg Pro Asp Arg Ile Val Val Gly Glu Cys Arg Gly Gly
305                 310                 315                 320
```

```
Glu Ser Leu Asp Met Leu Gln Ala Met Asn Thr Gly His Asp Gly Ser
                325                 330                 335

Leu Ser Thr Val His Ala Asn Ser Pro Arg Asp Ala Ile Ala Arg Leu
            340                 345                 350

Glu Thr Leu Val Leu Met Ala Gly Met Asp Leu Pro Leu Arg Ala Ile
        355                 360                 365

Arg Glu Gln Ile Ala Ser Ala Val Asp Val Ile Val Gln Leu Thr Arg
370                 375                 380

Leu Arg Asp Gly Thr Arg Val Thr His Val Thr Glu Val Gln Gly
385                 390                 395                 400

Met Glu Gly Glu Ile Val Thr Leu Gln Asp Ala Phe Leu Phe Asp Tyr
                405                 410                 415

Ser Ala Gly Val Asp Ala Arg Gly Arg Phe Leu Gly Arg Pro Gln Pro
            420                 425                 430

Thr Gly Val Arg Pro Arg Phe Thr Asp Lys Phe Arg Asp Leu Gly Ile
        435                 440                 445

Ala Leu Ser Pro Ser Val Phe Gly Val Gly Glu Pro Ser Arg Gly Arg
    450                 455                 460

Ala
465

<210> SEQ ID NO 40
<211> LENGTH: 465
<212> TYPE: PRT
<213> ORGANISM: Rhodococcus equi

<400> SEQUENCE: 40

Met Arg Leu Ser Gln Arg Leu Glu Ala Val Arg Gly Ala Ala Pro Val
1               5                   10                  15

Glu Ala Ala Ala Pro Ile Pro Pro Gly Lys Gln Gly Lys Ala Lys Thr
                20                  25                  30

Ser Leu Pro Pro Ala Asp Ala Leu Ala Glu Leu Lys Asp Arg Ala Ser
            35                  40                  45

Ala Ala Leu Tyr Thr Arg Ile Gly Thr Arg Phe Asn Asp Ser Ser Leu
        50                  55                  60

Ser Glu Glu Gln Leu His Leu Leu Val Arg Glu Glu Leu Ala Glu Ile
65                  70                  75                  80

Val Glu Gln Glu Thr Thr Pro Leu Thr Phe Asp Glu Arg Gln Arg Leu
                85                  90                  95

Leu Arg Glu Val Ala Asp Glu Val Leu Gly His Gly Pro Leu Gln Arg
            100                 105                 110

Leu Leu Glu Asp Pro Ser Val Thr Glu Ile Met Val Asn Ser His Asp
        115                 120                 125

Met Val Tyr Val Glu Arg Asp Gly Thr Leu Val Arg Ser Ser Ala Arg
    130                 135                 140

Phe Ala Asp Glu Ala His Leu Arg Arg Val Ile Glu Arg Ile Val Ser
145                 150                 155                 160

Ala Val Gly Arg Arg Ile Asp Glu Ser Ser Pro Leu Val Asp Ala Arg
                165                 170                 175

Leu Ala Asp Gly Ser Arg Val Asn Ala Val Ile Pro Pro Leu Ala Phe
            180                 185                 190

Asn Gly Ser Ser Leu Thr Ile Arg Lys Phe Ser Lys Asp Pro Phe Gln
        195                 200                 205

Val Asp Asp Leu Ile Ala Phe Gly Thr Leu Ser His Glu Met Ala Glu
    210                 215                 220
```

Leu Leu Asp Ala Cys Val Gln Ala Arg Leu Asn Val Ile Val Ser Gly
225                 230                 235                 240

Gly Thr Gly Thr Gly Lys Thr Thr Leu Leu Asn Val Leu Ser Ser Phe
            245                 250                 255

Ile Pro Glu Gly Glu Arg Ile Val Thr Ile Glu Asp Ala Val Glu Leu
        260                 265                 270

Gln Leu Gln Gln Asp His Val Arg Leu Glu Ser Arg Pro Pro Asn
    275                 280                 285

Ile Glu Gly Lys Gly Ala Val Thr Ile Arg Asp Leu Val Arg Asn Ser
290                 295                 300

Leu Arg Met Arg Pro Asp Arg Ile Val Val Gly Glu Cys Arg Gly Gly
305                 310                 315                 320

Glu Ser Leu Asp Met Leu Gln Ala Met Asn Thr Gly His Asp Gly Ser
                325                 330                 335

Leu Ser Thr Val His Ala Asn Ser Pro Arg Asp Ala Ile Ala Arg Leu
            340                 345                 350

Glu Thr Leu Val Leu Met Ala Gly Met Asp Leu Pro Leu Arg Ala Ile
        355                 360                 365

Arg Glu Gln Ile Ala Ser Ala Val Asp Val Ile Val Gln Leu Thr Arg
370                 375                 380

Leu Arg Asp Gly Thr Arg Arg Val Thr His Val Thr Glu Val Gln Gly
385                 390                 395                 400

Met Glu Gly Glu Ile Val Thr Leu Gln Asp Ala Phe Leu Phe Asp Tyr
                405                 410                 415

Ser Ala Gly Val Asp Ala Arg Gly Phe Leu Gly Arg Pro Gln Pro
            420                 425                 430

Thr Gly Val Arg Pro Arg Phe Thr Asp Lys Phe Arg Asp Leu Gly Ile
            435                 440                 445

Ala Leu Ser Pro Ser Val Phe Gly Val Gly Glu Pro Ser Arg Gly Arg
    450                 455                 460

Ala
465

<210> SEQ ID NO 41
<211> LENGTH: 465
<212> TYPE: PRT
<213> ORGANISM: Rhodococcus equi

<400> SEQUENCE: 41

Met Arg Leu Ser Gln Arg Leu Glu Ala Val Arg Gly Ala Ala Pro Val
1               5                   10                  15

Glu Ala Ala Ala Pro Ile Pro Pro Gly Lys Gln Gly Lys Ala Lys Thr
            20                  25                  30

Ser Leu Pro Pro Ala Asp Ala Leu Ala Glu Leu Lys Asp Arg Ala Ser
        35                  40                  45

Ala Ala Leu Tyr Thr Arg Ile Gly Thr Arg Phe Asn Asp Ser Ser Leu
    50                  55                  60

Ser Glu Glu Gln Leu His Leu Val Arg Glu Glu Leu Ala Glu Ile
65                  70                  75                  80

Val Glu Gln Glu Thr Thr Pro Leu Thr Phe Asp Glu Arg Gln Arg Leu
                85                  90                  95

Leu Arg Glu Val Ala Asp Glu Val Leu Gly His Gly Pro Leu Gln Arg
            100                 105                 110

Leu Leu Glu Asp Pro Ser Val Thr Glu Ile Met Val Asn Ser His Asp

```
            115                 120                 125
Met Val Tyr Val Glu Arg Asp Gly Thr Leu Val Arg Ser Ser Ala Arg
    130                 135                 140

Phe Ala Asp Glu Ala His Leu Arg Arg Val Ile Glu Arg Ile Val Ser
145                 150                 155                 160

Ala Val Gly Arg Arg Ile Asp Glu Ser Ser Pro Leu Val Asp Ala Arg
                165                 170                 175

Leu Ala Asp Gly Ser Arg Val Asn Ala Val Ile Pro Pro Leu Ala Phe
            180                 185                 190

Asn Gly Ser Ser Leu Thr Ile Arg Lys Phe Ser Lys Asp Pro Phe Gln
        195                 200                 205

Val Asp Asp Leu Ile Ala Phe Gly Thr Leu Ser His Glu Met Ala Glu
    210                 215                 220

Leu Leu Asp Ala Cys Val Gln Ala Arg Leu Asn Val Ile Val Ser Gly
225                 230                 235                 240

Gly Thr Gly Thr Gly Lys Thr Thr Leu Leu Asn Val Leu Ser Ser Phe
                245                 250                 255

Ile Pro Glu Gly Glu Arg Ile Val Thr Ile Glu Asp Ala Val Glu Leu
            260                 265                 270

Gln Leu Gln Gln Asp His Val Val Arg Leu Glu Ser Arg Pro Pro Asn
        275                 280                 285

Ile Glu Gly Lys Gly Ala Val Thr Ile Arg Asp Leu Val Arg Asn Ser
    290                 295                 300

Leu Arg Met Arg Pro Asp Arg Ile Val Val Gly Glu Cys Arg Gly Gly
305                 310                 315                 320

Glu Ser Leu Asp Met Leu Gln Ala Met Asn Thr Gly His Asp Gly Ser
                325                 330                 335

Leu Ser Thr Val His Ala Asn Ser Pro Arg Asp Ala Ile Ala Arg Leu
            340                 345                 350

Glu Thr Leu Val Leu Met Ala Gly Met Asp Leu Pro Leu Arg Ala Ile
        355                 360                 365

Arg Glu Gln Ile Ala Ser Ala Val Asp Val Ile Val Gln Leu Thr Arg
    370                 375                 380

Leu Arg Asp Gly Thr Arg Arg Val Thr His Val Thr Glu Val Gln Gly
385                 390                 395                 400

Met Glu Gly Glu Ile Val Thr Leu Gln Asp Ala Phe Leu Phe Asp Tyr
                405                 410                 415

Ser Ala Gly Val Asp Ala Arg Gly Arg Phe Leu Gly Arg Pro Gln Pro
            420                 425                 430

Thr Gly Val Arg Pro Arg Phe Thr Asp Lys Phe Arg Asp Leu Gly Ile
        435                 440                 445

Ala Leu Ser Pro Ser Val Phe Gly Val Gly Glu Pro Ser Arg Gly Arg
    450                 455                 460

Ala
465

<210> SEQ ID NO 42
<211> LENGTH: 623
<212> TYPE: PRT
<213> ORGANISM: Rhodococcus equi

<400> SEQUENCE: 42

Met Ser Arg Cys Val Val Ala Val Val Leu Ala Leu Gly Ala Gly Val
1               5                   10                  15
```

```
Leu Gly Ile Pro Ala Val Ala Ala Ala Glu Thr Glu Ala Val Gln
             20                  25                  30

Val Ser Ala Val Asp Thr Thr Arg Phe Pro Asp Ile Glu Val Ser Ile
         35                  40                  45

Leu Ala Pro Pro Gly Ile Glu Gly Gln Ala Ile Asp Pro Gly Thr Phe
     50                  55                  60

Ala Leu Thr Glu Gly Gly Val Pro Arg Glu Ile Glu Val Arg Gln Gln
 65                  70                  75                  80

Pro Gly Ser Glu Gln Asp Ile Val Leu Ala Ile Asp Val Ser Gly Gly
                 85                  90                  95

Met Ser Gly Pro Ala Leu Asp Asp Val Lys Arg Ala Ala Ser Asp Phe
            100                 105                 110

Val Arg Gln Ala Pro Thr Gly Ala His Ile Gly Ile Val Ala Ile Ser
        115                 120                 125

Ser Thr Pro Gln Val Leu Ser Glu Leu Thr Thr Asp Ser Glu Asp Leu
    130                 135                 140

Leu Arg Arg Ile Asp Gly Leu Lys Ala Gly Gly Asn Ser Ala Ile Ala
145                 150                 155                 160

Asp Ser Val Val Thr Ala Ala Glu Met Leu Glu Arg Gly Glu Ala Ala
                165                 170                 175

Asn Asn Ile Leu Leu Leu Leu Thr Asp Gly Ala Asp Thr Ser Ser Ala
            180                 185                 190

His Ser Met Ser Glu Leu Pro Ser Val Leu Ser Arg Ser Arg Ala Ser
        195                 200                 205

Leu Tyr Ala Val Gln Met Ser Thr Pro Glu Thr Asn Ser Ala Leu Leu
    210                 215                 220

Gln Gln Val Ala Arg Glu Ser Arg Gly Gln Tyr Ala Ser Ala Gly Asp
225                 230                 235                 240

Thr Ala Ala Leu Gly Ala Ile Tyr Gln Ser Ala Ala Arg Ala Leu Gly
                245                 250                 255

Asn Leu Tyr Val Val Arg Tyr Arg Ser Glu Ala Asn Gly Asp Thr Gln
            260                 265                 270

Val Val Ala Ser Val Arg Ser Gly Ala Ala Gly Arg Val Ser Asp Pro
        275                 280                 285

Phe Pro Val Thr Leu Pro Gly Val Val Pro Thr Pro Ser Val Val Ala
    290                 295                 300

Gly Thr Val Asp Gly Phe Phe Thr Ser Ser Thr Gly Leu Val Ile Gly
305                 310                 315                 320

Leu Leu Ala Cys Tyr Ser Ala Leu Ala Gly Gly Val Leu Ala Val Ala
                325                 330                 335

Gly Arg Ala Pro Ala Arg Ile Ser Ala Ala Arg Arg Gly Arg Gln Asp
            340                 345                 350

Gly Arg Asp Ser Met Leu Ser Arg Phe Ala Glu Arg Leu Val Gln Trp
        355                 360                 365

Ile Asp Gln Asn Leu Arg Arg Arg Gly Arg Ile Ala Ala Arg Thr Gln
    370                 375                 380

Ala Leu Gln Glu Ala Gly Leu Lys Leu Arg Pro Gly Asp Phe Ile Ala
385                 390                 395                 400

Leu Val Gly Ala Ala Ala Ile Thr Ala Ala Ile Gly Leu Leu Ala
                405                 410                 415

Ser Gly Ile Val Ala Ala Leu Leu Ala Ala Ile Thr Val Gly Leu
            420                 425                 430

Ser Arg Ile Tyr Leu Arg Val Met Ala Gly Arg Arg Arg Ala Ala Phe
```

```
            435                 440                 445
Ala Asp Gln Leu Asp Asp Ser Leu Gln Leu Leu Ala Ser Asn Leu Arg
450                 455                 460

Ala Gly His Ser Met Leu Arg Ala Leu Asp Ser Leu Ser Arg Glu Ala
465                 470                 475                 480

Glu Val Pro Thr Ser Glu Glu Phe Ala Arg Ile Val Asn Glu Thr Arg
                485                 490                 495

Val Gly Arg Asp Leu Asn Glu Ser Leu Asp Asp Val Ala Arg Arg Met
                500                 505                 510

Arg Ser Asp Asp Phe Asn Trp Ile Ala Gln Ala Ile Ala Ile Asn Arg
                515                 520                 525

Glu Val Gly Gly Asp Leu Ala Glu Val Leu Asp Gln Val Gly Asn Thr
530                 535                 540

Ile Arg Glu Arg Asn Gln Ile Arg Arg Gln Val Lys Ala Leu Ala Ala
545                 550                 555                 560

Glu Gly Lys Leu Ser Ala Tyr Val Leu Met Ala Leu Pro Phe Gly Leu
                565                 570                 575

Thr Ala Phe Leu Leu Val Ser Asn Pro Asp Tyr Leu Ser Lys Leu Thr
                580                 585                 590

Gly Ser Ala Ile Gly Tyr Val Met Ile Ala Val Gly Leu Val Met Leu
                595                 600                 605

Thr Val Gly Gly Leu Trp Met Asn Lys Val Val Ser Val Lys Phe
610                 615                 620

<210> SEQ ID NO 43
<211> LENGTH: 621
<212> TYPE: PRT
<213> ORGANISM: Rhodococcus equi

<400> SEQUENCE: 43

Met Ser Arg Cys Val Ala Val Val Leu Ala Leu Gly Ala Gly Val
1               5                   10                  15

Leu Gly Ile Pro Ala Val Ala Ala Ala Glu Thr Glu Ala Val Gln
                20                  25                  30

Val Ser Ala Val Asp Thr Thr Arg Phe Pro Ile Glu Val Ser Ile
                35                  40                  45

Leu Ala Pro Pro Gly Ile Glu Gly Gln Ala Ile Asp Pro Gly Thr Phe
50                  55                  60

Ala Leu Thr Glu Gly Gly Val Pro Arg Glu Ile Glu Val Arg Gln Gln
65                  70                  75                  80

Pro Gly Ser Glu Gln Asp Ile Val Leu Ala Ile Asp Val Ser Gly Gly
                85                  90                  95

Met Ser Gly Pro Ala Leu Asp Asp Val Lys Arg Ala Ala Ser Asp Phe
                100                 105                 110

Val Arg Gln Ala Pro Thr Gly Ala His Ile Gly Ile Val Ala Ile Ser
                115                 120                 125

Ser Thr Pro Gln Val Leu Ser Glu Leu Thr Thr Asp Ser Glu Asp Leu
                130                 135                 140

Leu Arg Arg Ile Asp Gly Leu Lys Ala Gly Asn Ser Ala Ile Ala
145                 150                 155                 160

Asp Ser Val Val Thr Ala Ala Glu Met Leu Glu Arg Gly Glu Ala Ala
                165                 170                 175

Asn Asn Ile Leu Leu Leu Leu Thr Asp Gly Ala Asp Thr Ser Ser Ala
                180                 185                 190
```

```
His Ser Met Ser Glu Leu Pro Ser Val Leu Ser Arg Ser Arg Ala Ser
        195                 200                 205
Leu Tyr Ala Val Gln Met Ser Thr Pro Glu Thr Asn Ser Ala Leu Leu
    210                 215                 220
Gln Gln Val Ala Arg Glu Ser Arg Gly Gln Tyr Ala Ser Ala Gly Asp
225                 230                 235                 240
Thr Ala Ala Leu Gly Ala Ile Tyr Gln Ser Ala Arg Ala Leu Gly
                245                 250                 255
Asn Leu Tyr Val Val Arg Tyr Arg Ser Glu Ala Asn Gly Asp Thr Gln
                260                 265                 270
Val Val Ala Ser Val Arg Ser Gly Ala Ala Gly Arg Val Ser Asp Pro
            275                 280                 285
Phe Pro Val Thr Leu Pro Gly Val Pro Thr Pro Ser Val Val Ala
    290                 295                 300
Gly Thr Val Asp Gly Phe Phe Thr Ser Ser Thr Gly Leu Val Ile Gly
305                 310                 315                 320
Leu Leu Ala Cys Tyr Ser Ala Leu Ala Gly Leu Ala Val Ala Gly Arg
                325                 330                 335
Gly Pro Ala Arg Ile Ser Ala Ala Arg Arg Gly Arg Gln Asp Gly Arg
                340                 345                 350
Asp Ser Met Leu Ser Arg Phe Ala Glu Arg Leu Val Gln Trp Ile Asp
                355                 360                 365
Gln Asn Leu Arg Arg Arg Gly Arg Ile Ala Ala Arg Thr Gln Ala Leu
    370                 375                 380
Gln Glu Ala Gly Leu Lys Leu Arg Pro Gly Asp Phe Ile Ala Leu Val
385                 390                 395                 400
Gly Ala Ala Ile Thr Ala Ala Ile Gly Leu Leu Ala Ser Gly
                405                 410                 415
Ile Val Ala Ala Leu Leu Leu Ala Ala Ile Thr Val Gly Leu Ser Arg
                420                 425                 430
Ile Tyr Leu Arg Val Met Ala Gly Arg Arg Ala Ala Phe Ala Asp
    435                 440                 445
Gln Leu Asp Asp Ser Leu Gln Leu Leu Ala Ser Asn Leu Arg Ala Gly
450                 455                 460
His Ser Met Leu Arg Ala Leu Asp Ser Leu Ser Arg Glu Ala Glu Val
465                 470                 475                 480
Pro Thr Ser Glu Glu Phe Ala Arg Ile Val Asn Glu Thr Arg Val Gly
                485                 490                 495
Arg Asp Leu Asn Glu Ser Leu Asp Asp Val Ala Arg Arg Met Arg Ser
                500                 505                 510
Asp Asp Phe Asn Trp Ile Ala Gln Ala Ile Ala Ile Asn Arg Glu Val
            515                 520                 525
Gly Gly Asp Leu Ala Glu Val Leu Asp Gln Val Gly Asn Thr Ile Arg
            530                 535                 540
Glu Arg Asn Gln Ile Arg Arg Gln Val Lys Ala Leu Ala Ala Glu Gly
545                 550                 555                 560
Lys Leu Ser Ala Tyr Val Leu Met Ala Leu Pro Phe Gly Leu Thr Ala
                565                 570                 575
Phe Leu Leu Val Ser Asn Pro Asp Tyr Leu Ser Lys Leu Thr Gly Ser
                580                 585                 590
Ala Ile Gly Tyr Val Met Ile Ala Val Gly Leu Val Met Leu Thr Val
            595                 600                 605
Gly Gly Leu Trp Met Asn Lys Val Val Ser Val Lys Phe
```

610                 615                 620

<210> SEQ ID NO 44
<211> LENGTH: 620
<212> TYPE: PRT
<213> ORGANISM: Rhodococcus equi

<400> SEQUENCE: 44

Met Ser Arg Cys Val Val Ala Val Leu Ala Leu Gly Ala Gly Val
1               5                   10                  15

Leu Gly Ile Pro Ala Val Ala Ala Glu Ala Val Gln Val Ser Ala
                20                  25                  30

Val Asp Thr Thr Arg Phe Pro Asp Ile Glu Val Ser Ile Leu Ala Pro
                35                  40                  45

Pro Gly Ile Glu Gly Gln Ala Ile Asp Pro Gly Thr Phe Ala Leu Thr
    50                  55                  60

Glu Gly Gly Val Pro Arg Glu Ile Glu Val Arg Gln Gln Pro Gly Ser
65                  70                  75                  80

Glu Gln Asp Ile Val Leu Ala Ile Asp Val Ser Gly Gly Met Ser Gly
                85                  90                  95

Pro Ala Leu Asp Asp Val Lys Arg Ala Ala Ser Asp Phe Val Arg Gln
            100                 105                 110

Ala Pro Thr Gly Ala His Ile Gly Ile Val Ala Ile Ser Ser Thr Pro
        115                 120                 125

Gln Val Leu Ser Glu Leu Thr Thr Asp Ser Glu Asp Leu Leu Arg Arg
    130                 135                 140

Ile Asp Gly Leu Lys Ala Gly Gly Asn Ser Ala Ile Ala Asp Ser Val
145                 150                 155                 160

Val Thr Ala Ala Glu Met Leu Glu Arg Gly Glu Ala Ala Asn Asn Ile
                165                 170                 175

Leu Leu Leu Leu Thr Asp Gly Ala Asp Thr Ser Ser Ala His Ser Met
            180                 185                 190

Ser Glu Leu Pro Ser Val Leu Ser Arg Ser Arg Ala Ser Leu Tyr Ala
        195                 200                 205

Val Gln Met Ser Thr Pro Glu Thr Asn Ser Ala Leu Leu Gln Gln Val
    210                 215                 220

Ala Arg Glu Ser Arg Gly Gln Tyr Ala Ser Ala Gly Asp Thr Ala Ala
225                 230                 235                 240

Leu Gly Ala Ile Tyr Gln Ser Ala Ala Arg Ala Leu Gly Asn Leu Tyr
                245                 250                 255

Val Val Arg Tyr Arg Ser Glu Ala Asn Gly Asp Thr Gln Val Val Ala
            260                 265                 270

Ser Val Arg Ser Gly Ala Ala Gly Arg Val Ser Asp Pro Phe Pro Val
        275                 280                 285

Thr Leu Pro Gly Val Val Pro Thr Pro Ser Val Ala Gly Thr Val
    290                 295                 300

Asp Gly Phe Phe Thr Ser Ser Thr Gly Leu Val Ile Gly Leu Leu Ala
305                 310                 315                 320

Cys Tyr Ser Ala Leu Ala Gly Gly Val Leu Ala Val Ala Gly Arg Ala
                325                 330                 335

Pro Ala Arg Ile Ser Ala Ala Arg Arg Gly Arg Gln Asp Gly Arg Asp
            340                 345                 350

Ser Met Leu Ser Arg Phe Ala Glu Arg Leu Val Gln Trp Ile Asp Gln
        355                 360                 365

Asn Leu Arg Arg Arg Gly Arg Ile Ala Ala Arg Thr Gln Ala Leu Gln
    370                 375                 380

Glu Ala Gly Leu Lys Leu Arg Pro Gly Asp Phe Ile Ala Leu Val Gly
385                 390                 395                 400

Ala Ala Ala Ile Thr Ala Ala Ile Gly Leu Leu Ala Ser Gly Ile
                405                 410                 415

Val Ala Ala Leu Leu Leu Ala Ala Ile Thr Val Gly Leu Ser Arg Ile
                420                 425                 430

Tyr Leu Arg Val Met Ala Gly Arg Arg Ala Ala Phe Ala Asp Gln
                435                 440                 445

Leu Asp Asp Ser Leu Gln Leu Leu Ala Ser Asn Leu Arg Ala Gly His
    450                 455                 460

Ser Met Leu Arg Ala Leu Asp Ser Leu Ser Arg Glu Ala Glu Val Pro
465                 470                 475                 480

Thr Ser Glu Glu Phe Ala Arg Ile Val Asn Glu Thr Arg Val Gly Arg
                485                 490                 495

Asp Leu Asn Glu Ala Leu Asp Asp Val Ala Arg Arg Met Arg Ser Asp
                500                 505                 510

Asp Phe Asn Trp Ile Ala Gln Ala Ile Ala Ile Asn Arg Glu Val Gly
                515                 520                 525

Gly Asp Leu Ala Glu Val Leu Asp Gln Val Gly Asn Thr Ile Arg Glu
    530                 535                 540

Arg Asn Gln Ile Arg Arg Gln Val Lys Ala Leu Ala Glu Gly Lys
545                 550                 555                 560

Leu Ser Ala Tyr Val Leu Met Ala Leu Pro Phe Gly Leu Thr Ala Phe
                565                 570                 575

Leu Leu Val Ser Asn Pro Asp Tyr Leu Ser Lys Leu Thr Gly Ser Ala
                580                 585                 590

Ile Gly Tyr Val Met Ile Ala Val Gly Leu Val Met Leu Thr Val Gly
                595                 600                 605

Gly Leu Trp Met Asn Lys Val Val Ser Val Lys Phe
    610                 615                 620

<210> SEQ ID NO 45
<211> LENGTH: 296
<212> TYPE: PRT
<213> ORGANISM: Rhodococcus equi

<400> SEQUENCE: 45

Val Ile Pro Pro Leu Val Leu Met Ala Ala Leu Ser Val Gly Gly Ala
1               5                   10                  15

Leu Gly Val Leu Val Trp Leu Thr Ala Gly Ala Arg Asp Pro Glu Arg
                20                  25                  30

Gly Pro Ala Leu Gln Asn Leu Gln Ser Gln Leu Ala Leu Pro Ile Pro
            35                  40                  45

Glu Ser Gly Gly Ala Pro Pro Leu Ser Leu Gly Arg Phe Val Lys Leu
    50                  55                  60

Leu Ser Pro Pro Gly Thr Met Ala Arg Leu Glu Arg Leu His Ile Leu
65                  70                  75                  80

Ala Gly Arg Pro Ala Ala Trp Val Pro Glu Arg Ala Ala Met Ala Lys
                85                  90                  95

Ile Val Leu Ala Ala Ala Ala Leu Leu Gly Leu Leu Ala Val Gly
                100                 105                 110

Ala Ser Pro Gly Val Gly Arg Val Leu Phe Ala Ala Ala Val Ala
            115                 120                 125

```
Leu Ala Tyr Phe Val Pro Glu Leu Leu Leu Gln Ser Arg Gly Gln Glu
        130                 135                 140

Arg Gln Ala Ala Ile Glu Leu Ala Leu Ala Asp Thr Leu Asp Gln Met
145                 150                 155                 160

Thr Ile Ala Val Glu Ala Gly Leu Gly Phe Glu Ala Ala Met Gln Arg
                165                 170                 175

Ala Ala Lys Asn Gly Lys Gly Pro Leu Ala Glu Glu Phe Ile Arg Thr
            180                 185                 190

Leu Gln Asp Ile Gln Met Gly Gln Ser Arg Arg Ile Ala Tyr Leu Asp
        195                 200                 205

Leu Ala Ala Arg Thr Lys Ala Pro Asn Leu Arg Arg Phe Leu Arg Ala
210                 215                 220

Val Ile Gln Ala Asp Glu Tyr Gly Val Ala Ile Ala Glu Val Leu Arg
225                 230                 235                 240

Thr Gln Ala Ser Glu Met Arg Leu Lys Arg Arg Gln Ser Ala Glu Glu
                245                 250                 255

Lys Ala Met Lys Val Pro Val Lys Val Leu Phe Pro Leu Met Thr Cys
            260                 265                 270

Ile Leu Pro Thr Ile Phe Ile Val Ile Leu Gly Pro Ala Val Ile Asn
        275                 280                 285

Met Met Glu Val Leu Gly Gly Met
            290                 295

<210> SEQ ID NO 46
<211> LENGTH: 296
<212> TYPE: PRT
<213> ORGANISM: Rhodococcus equi

<400> SEQUENCE: 46

Val Ile Pro Pro Leu Val Leu Val Ala Ala Leu Ser Val Gly Gly Ala
1               5                   10                  15

Leu Gly Val Leu Val Trp Leu Thr Ala Gly Ala Arg Asp Pro Glu Arg
            20                  25                  30

Gly Pro Ala Leu Gln Asn Leu Gln Ser Gln Leu Ala Leu Pro Ile Pro
        35                  40                  45

Val Ser Gly Gly Ala Pro Pro Leu Ser Leu Gly Arg Phe Val Lys Leu
    50                  55                  60

Leu Ser Pro Pro Gly Thr Met Ala Arg Leu Glu Arg Leu His Ile Leu
65                  70                  75                  80

Ala Gly Arg Pro Ala Ala Trp Val Pro Glu Arg Ala Ala Met Ala Lys
                85                  90                  95

Ile Val Leu Ala Ala Ala Ala Leu Leu Gly Leu Leu Ala Val Gly
            100                 105                 110

Ala Ser Pro Gly Val Gly Arg Val Leu Phe Ala Ala Ala Ala Val Ala
        115                 120                 125

Leu Ala Tyr Phe Val Pro Glu Leu Leu Leu Gln Ser Arg Gly Gln Glu
    130                 135                 140

Arg Gln Ala Ala Ile Glu Leu Ala Leu Ala Asp Thr Leu Asp Gln Met
145                 150                 155                 160

Thr Ile Ala Val Glu Ala Gly Leu Gly Phe Glu Ala Ala Met Gln Arg
                165                 170                 175

Ala Ala Lys Asn Gly Lys Gly Pro Leu Ala Glu Glu Phe Ile Arg Thr
            180                 185                 190

Leu Gln Asp Ile Gln Met Gly Gln Ser Arg Arg Ile Ala Tyr Leu Asp
```

```
                195                 200                 205
Leu Ala Ala Arg Thr Lys Ala Pro Asn Leu Arg Arg Phe Leu Arg Ala
    210                 215                 220
Val Ile Gln Ala Asp Glu Tyr Gly Val Ala Ile Ala Glu Val Leu Arg
225                 230                 235                 240
Thr Gln Ala Ser Glu Met Arg Leu Lys Arg Gln Ser Ala Glu Glu
                245                 250                 255
Lys Ala Met Lys Val Pro Val Lys Val Leu Phe Pro Leu Met Thr Cys
            260                 265                 270
Ile Leu Pro Thr Ile Phe Ile Val Ile Leu Gly Pro Ala Val Ile Asn
                275                 280                 285
Met Met Glu Val Leu Gly Gly Met
    290                 295

<210> SEQ ID NO 47
<211> LENGTH: 296
<212> TYPE: PRT
<213> ORGANISM: Rhodococcus equi

<400> SEQUENCE: 47

Val Ile Pro Pro Leu Val Leu Met Ala Ala Leu Ser Val Gly Gly Ala
1               5                   10                  15
Leu Gly Val Leu Val Trp Leu Thr Ala Gly Ala Arg Asp Pro Glu Arg
                20                  25                  30
Gly Pro Ala Leu Gln Asn Leu Gln Ser Gln Leu Ala Leu Pro Ile Pro
            35                  40                  45
Glu Ser Gly Gly Ala Pro Pro Ile Ser Leu Gly Arg Phe Val Lys Leu
    50                  55                  60
Leu Ser Pro Pro Gly Thr Met Ala Arg Leu Glu Arg Leu His Ile Leu
65                  70                  75                  80
Ala Gly Arg Pro Ala Ala Trp Val Pro Glu Arg Ala Ala Met Ala Lys
                85                  90                  95
Ile Val Leu Ala Ala Ala Ala Leu Leu Gly Leu Leu Ala Ala Gly
                100                 105                 110
Ala Ser Pro Gly Val Gly Arg Val Leu Phe Ala Ala Ala Ala Val Ala
            115                 120                 125
Leu Ala Tyr Phe Val Pro Glu Leu Leu Leu Gln Ser Arg Val Gln Glu
    130                 135                 140
Arg Gln Ala Ala Ile Glu Leu Ala Leu Ala Asp Thr Leu Asp Gln Met
145                 150                 155                 160
Thr Ile Ala Val Glu Ala Gly Leu Gly Phe Glu Ala Ala Met Gln Arg
                165                 170                 175
Ala Ala Lys Asn Gly Lys Gly Pro Leu Ala Glu Glu Phe Ile Arg Thr
            180                 185                 190
Leu Gln Asp Ile Gln Met Gly Gln Ser Arg Arg Ile Ala Tyr Leu Asp
    195                 200                 205
Leu Ala Ala Arg Thr Lys Ala Pro Asn Leu Arg Arg Phe Leu Arg Ala
    210                 215                 220
Val Ile Gln Ala Asp Glu Tyr Gly Val Ala Ile Ala Glu Val Leu Arg
225                 230                 235                 240
Thr Gln Ala Ser Glu Met Arg Leu Lys Arg Gln Ser Ala Glu Glu
                245                 250                 255
Lys Ala Met Lys Val Pro Val Lys Val Leu Phe Pro Leu Met Thr Cys
            260                 265                 270
```

```
Ile Leu Pro Thr Ile Phe Ile Val Ile Leu Gly Pro Ala Val Ile Asn
            275                 280                 285
Met Met Glu Val Leu Gly Gly Met
    290                 295

<210> SEQ ID NO 48
<211> LENGTH: 789
<212> TYPE: DNA
<213> ORGANISM: Rhodococcus equi

<400> SEQUENCE: 48
gtgatcgtcg cagcgggcgt cggcgctgcc ctcctgggca tcctcgccgg ggcgttcgca      60
aacagtgcga tcgaccgcgt gcgcctggag accgcgtgcg ccgagccgaa gtcgaccccc     120
gccaactcaa ccccgccgtc ccctccccct acgtccgcgg tggccgcccg gatcgcgatg     180
atcgacacca tcacgcgacg acacgacatc agtgcccgcc gcgtgctcgt cgaactcgca     240
actgccctcc tgttcgtcgc gatcactctc cgtctcgccg ctctcgatct tctcccggca     300
gcaccggcct atctctggtt cgccgtcgtc gggatcgccc tcgccgtcat cgacatcgat     360
tgcaaacggc tgccgaactt cctcgtcgta ccgtcgtacc cgatcgtatt cgcctgcctg     420
gcagtgggtt ccgtcgtcac gggcgactgg tcggccctgc tgcgcgccgc gatcggtgcc     480
gccgtcctgt tcgggttcta cttcgtactc gccctgatct atccggccgg catgggttc      540 ggcgacgtca aacttgccgg cgtcatcggc gccgtcctcg cctacctgtc gtacggcaca     600
ctgctcgtcg gggcgtttct cgcgttcctg gtggccgcac tcgtcggcct gatcatcctg     660
gtcacccgtc gcggacggat cgggaccacg attcccttcg ggccgtacat gattgcggcg     720
gccgtcgttg cgatcctggc agccgatccg ctggcgcgtg cgtatctgga ctgggccgcc     780
gcggcctga                                                             789

<210> SEQ ID NO 49
<211> LENGTH: 789
<212> TYPE: DNA
<213> ORGANISM: Rhodococcus equi

<400> SEQUENCE: 49
gtgatcgtcg cagcgggcgt cggcgccgca ctcctgggca tccttgccgg ggcattcgca      60
aacagtgcga tcgaccgcgt gcgcctggag accgcgtgcg ccgagccgag ggcgaccccc     120
accggctcaa ccccgccgcc ccctccccct acgtccgcgg tagccacccg gatcgcgatg     180
atcgacacca tcacgcgacg acgcgacatc agtgcccgcc gcatgctcgt cgaactcgca     240
acggccctcc tgttcgtcgc gatcactctc cgtctcgccg ctctcgatct tctcccggca     300
gcaccggcct atctctggtt cgccgtcatc gggatcgccc tcgccgtcat cgacatcgat     360
tgcaaacggc tgccgaactt cctcgtcgta ccgtcgtacc cgatcgtatt cgcctgcctg     420
gcagtgggtt ccgtcgtcac gggcgactgg tcggccctgc tgcgcgccgc gatcggtgcc     480
gccgtcctgt tcgggttcta cttcgtactc gccctgatct atccggccgg catggggttc     540
ggcgacgtca aacttgccgg cgtcatcggc gccgtcctcg cctacctgtc gtacggcaca     600
ctgctcgtcg gggcgtttct cgcgttcctg gtggccgcac tcgtgggcct catcatcctg     660
gtcacccgtc gcggtcggat cgggaccacg attcccttcg ggccgtacat gattgcggcg     720
gccgtcgttg cgatcctcgc ggccgatccg ctggcgcgtg cgtatctgga ctgggccgcc     780
gcggcctga                                                             789
```

<210> SEQ ID NO 50
<211> LENGTH: 789
<212> TYPE: DNA
<213> ORGANISM: Rhodococcus equi

<400> SEQUENCE: 50

```
gtgatcgtcg cagcgggcgt cggcgccgca ctcctgggta tcctcgccgg ggcgttcgcg      60
aacagtgcga tcgaccgcgt gcgcctggag accgcgtgcg ccgagccgaa gtcgaccccc     120
accggctcaa ccccgccgcc cccctcccct gcgtccgcgg tagccacccg gatcgcgatg     180
atcgacacca tcacgcgacg acgcgacatc agtgcccgcc gcatgctcgt cgaactcgca     240
acggccctcc tgttcgtcgc gatcactctc cgtctcgccg ctctcggtct tctcccggca     300
gcaccggcct atctctggtt cgccgtcatc gggatcgccc tcgccgtcat cgacatcgat     360
tgcaaacggc tgccgaactt cctcgtcgta ccgtcgtacc cgatcgtatt cgcctgcctg     420
gcagtgggtt ccgtcgtcac gggcgactgg tcggccctgc tgcgcgccgc gatcggtgcc     480
gccgtcctgt tcgggttcta cttcgtactc gccctgatct atccggccgg catgggcttc     540
ggcgacgtca aacttgccgg cgtcatcggc gccgtcctcg cctacctgtc gtacggcaca     600
ctgctcgtcg gggcgtttct cgcgttcctg gtggccgcac tgtcggcct gatcatcctg      660 gtcacccgtc gcggacggat cgggaccacg attcccttcg ggccgtacat gattgcggcg     720
gccgtcgttg cgatcctggc ggccgatccg ctggcgcgcg cgtatctgga ctgggccgcc     780
gcggcctga                                                            789
```

<210> SEQ ID NO 51
<211> LENGTH: 213
<212> TYPE: DNA
<213> ORGANISM: Rhodococcus equi

<400> SEQUENCE: 51

```
atgaacctct tcttcgcgaa cctgtacctc atgggcttag acgtcaagga ccgtctgacc      60
cgtgacgacc gcggcgccac tgcggtcgag tacggactga tggtcgccgg catcgcgatg     120
gtgatcctca ttgcggtctt cgccttcggc ggcaagatca gcgagctgtt tagcggcttc     180
aatttcgaca agcccgctgc gtcgggcacg tag                                  213
```

<210> SEQ ID NO 52
<211> LENGTH: 204
<212> TYPE: DNA
<213> ORGANISM: Rhodococcus equi

<400> SEQUENCE: 52

```
atgaacctct tcttcgcgaa cctgtacctc atgggcttag acgtcaagga ccgtctgacc      60
cgtgacgacc gcggcgccac tgcggtcgag tacggactga tggtcgccgg catcgcgatg     120
gtgatcatca tcgccgtctt tgccttcggc ggcagactca gcaccctgtt ccagaacttc     180
aacttcgcca acccgggtaa ctag                                            204
```

<210> SEQ ID NO 53
<211> LENGTH: 408
<212> TYPE: DNA
<213> ORGANISM: Rhodococcus equi

<400> SEQUENCE: 53

```
atgggcatgc gccgttttgg ttctgattct ggtgctgccg cagtcgaatt cgctctcgtt      60
gttccgattc tgatcacact ggtcctcggc atcgtggagt tcggtcgggg atacaacgtc     120
```

| | |
|---|---|
| cagaacgcgg tcagcgctgc tgcccgcgag ggtgcacgga cgatggcgat caagaaggat | 180 |
| ccggcggcgg cgcgtgccgc cgtgaagggc gcgggtgtgt tcagtccggc gatcaccgat | 240 |
| gcggagatct gcatcagcac ttcgggaacg cagggctgtt cggcaacgtc gtgcccgagc | 300 |
| ggaagtaccg tgacgctcac ggtcagctat ccactcgagt acatgacggg actctttccc | 360 |
| ggtaagccga cgctcaccgg cacggggtc atgcgatgcg gtgggtga | 408 |

<210> SEQ ID NO 54
<211> LENGTH: 408
<212> TYPE: DNA
<213> ORGANISM: Rhodococcus equi

<400> SEQUENCE: 54

| | |
|---|---|
| gtgatcatga agcgcctcac ttccgattca ggggtcgccg cagtcgaatt cgctctcgtc | 60 |
| gttccgatcc tgatcacact ggtcctcggc atcgtcgagt tcggtcgggg atacaacgtc | 120 |
| cagaacgcgg tcagcgctgc tgcccgcgag ggtgcacgga cgatggcgat caagaaggat | 180 |
| ccggcggcgg cgcgtgccgc cgtgaagggc gcgggtgtgt tcagtccggc gatcaccgat | 240 |
| gcggagatct gcatcagcac ttcgggctcg cagggctgtt cggcaacgtc gtgtccgagc | 300 |
| ggaagtaccg tgacgctcac ggtcagctat ccactcgagt acatgacggg actctttccc | 360 |
| ggtaagccga cgctcaccgg cacggggtc atgcgatgcg gtgggtga | 408 |

<210> SEQ ID NO 55
<211> LENGTH: 393
<212> TYPE: DNA
<213> ORGANISM: Rhodococcus equi

<400> SEQUENCE: 55

| | |
|---|---|
| ttgcgttccg attcaggggt cgccgcagtc gaattcgctc tcgtcgttcc gatcctgatc | 60 |
| acactggtcc tcggcatcgt ggagttcggt cggggttaca acgtccagaa cgcggtcagc | 120 |
| gctgctgccc gcgagggtgc acggacgatg gcgatcaaga aggatccggc ggcggcgcgt | 180 |
| gctgccgtga agggcgcggg tgtgttcagt ccggcgatca ccgatgcgga gatctgcatc | 240 |
| agcacttcgg gaacgcaggg ctgttcggca acgtcgtgtc cgagcggaag taccgtgacg | 300 |
| ctcacggtca gctatccact cgagtacatg acgggactct ttcccggtaa gccgacgctc | 360 |
| accggcacgg gggtcatgcg atgcggtggg tga | 393 |

<210> SEQ ID NO 56
<211> LENGTH: 966
<212> TYPE: DNA
<213> ORGANISM: Rhodococcus equi

<400> SEQUENCE: 56

| | |
|---|---|
| atgcggtggg tgaggtctcg catgtctaat gacgagcgcg gggtcgtcgc cgtgctcgtc | 60 |
| gcgatcctca tggtcgtgct cctgggatgt gctgcgatct cggtcgacat cggtgcgaac | 120 |
| tatgtcgtca acgtcagtt gcagaacggg gccgatgcgg ctgcgctcgc cgtagctcag | 180 |
| gaatccagtt gcaaggcagg atcttccgcc tcatccgtgt cgagccttgt ccaggcgaac | 240 |
| gtcaacagct cgtcggcttc aagtgcgcg gtgatcgacg tgtgaagcg gaaggtgacg | 300 |
| gtcactgcgt cggcggtggg tgacgacggc ctcgccggcc ggaggaacgt gttcgctccg | 360 |
| gtcctcggag tcgaccgcag cgagatctcg cgtctgcga ctgcaagctg cgtgtttccc | 420 |
| ctcgggggga ccgcggaact cccgctcacg ttccacaagt gccatttcga cgaatcccgc | 480 |
| agtctggacg tgaagatcct cgtcgcctac aacgtgacgg cgccgcgctg caacggaacc | 540 |

```
tcgggaaatg cggcaccggg caatttcggc tggctgcagg gggcgaacgg tcgatgcccg    600
gcgaagatcg acgccgccgt ctatgcaaca ccgggcgaca ccgtaacaa  cattccgggg    660 ccgtgcaagg acaccatcaa gcagtttcag aatgccgtcg tccgggtccc gatctacgac    720
gtcgcaggtg aaccggaag  cggtggatgg tttcacgtcg tcggtttggc tgccttcaag    780
attcagggct accggctgag cggcaacccg gagttcaact ggaacaacga tgttcacggg    840
gcgctgagtt gcaccggcag ctgtcgcggc atcatcggca ccttcgtgaa aattgtcagc    900
ctcgattcgg atctgacgcc gggagggatc gatttcggcg tgagtacgat cagcttgctc    960
gattag                                                               966

<210> SEQ ID NO 57
<211> LENGTH: 966
<212> TYPE: DNA
<213> ORGANISM: Rhodococcus equi

<400> SEQUENCE: 57
atgcggtggg tgaggtctcg catgtcgaat gacgagcgcg gggtcgtcgc cgtgttcgtc    60
gcgatcctca tggtcgtgct cctgggatgt gctgcgatct cggtcgacat cggtgcgaac    120
tatgtcgtca aacgtcagtt gcagaacggg gccgatgcgg ctgcgctcgc cgtagctcag    180
gaatccagtt gcaaggcagg atcttccgcc tcatccgtgt cgaggcttgt ccaggcgaac    240
gtcaacagct cgtcggcttc aagtgcgcg  gtgatcgacg gtgtgaagcg gaaggtgacg    300
gtcactgcgt cggcggtggg tgacgacggc ctcgccggcc ggaggaacgt gttcgctccg    360
gtcctcggag tcgaccgcag cgagatctcg gcgtctgcga ctgcaagctg cgtgtttccc    420
ctcgggggga ccgcggaact cccgctcacg ttccacaagt gccatttcga cgaatcccgc    480
agtctggacg tgaagatcct cgtcgcctac aacgtgacgg cgccgcgctg caacggaacc    540
tcgggaaatg cggcaccggg caatttcggc tggctacagg gggtgaacgg tcgatgcccg    600
gcgaagatcg acgcggccgt ctatgcaaca ccgggcgaca ccgtaacaa  cattccgggg    660 ccgtgcaagg acaccatcaa gcagtttcag aatgccgtcg tccgggtccc gatctacgac    720
gtcgcaggtg aaccggaag  cggtggatgg tttcacgtcg tcggtttggc tgccttcaag    780
attcagggct accggctgag cggcaacccg gagttcaact ggaacaacga tgttcacgga    840
gcgctgagtt gcaccggcag ctgtcgcggc atcatcggca ccttcgtgaa aattgtcagc    900
ctcgattcgg atctgacgcc gggagggatc gatttcggcg tgagtacgat cagcttgctc    960
gattag                                                               966

<210> SEQ ID NO 58
<211> LENGTH: 966
<212> TYPE: DNA
<213> ORGANISM: Rhodococcus equi

<400> SEQUENCE: 58
atgcggtggg tgaggtctcg catgtctaat gacgagcgcg gggtcgtcgc cgtgctcgtc    60
gcgatcctca tggtcgtgct cctgggatgt gctgcgatct cggtcgacat cggtgcgaac    120
tatgtcgtca aacgtcagtt gcagaacggg gccgatgcgg ctgcgctcgc cgtagctcag    180
gaatccaatt gcaaggcagg atcttccgcc tcatccgtgt cgagccttgt ccaggcgaac    240
gtcaacagct cgtcggcttc aagtgcggcg gtgatcgacg gtgtgaagcg gaaggtgacg    300
gtcactgcgt cggcggtggg tgacgacggc ctcgccggcc ggaggaacgt gttcgctccg    360
```

```
gtcctcggag tcgaccgcag cgagatctcg gcgtctgcga ctgcaagctg cgtgtttccc    420
ctcgggggga ccgcggaact cccgctcacg ttccacaagt gccatttcga cgaatcccgc    480
agtctggacg tgaagatcct cgtcgcctac aacgtgacgg cgccgcgctg caacggaacc    540
tcgggaaatg cggcaccggg caatttcggc tggctgcagg gggcgaacgg tcgatgcccg    600
gcgaagatcg accccaccgt ctatgcaaca ccgggcgaca ccggtaacaa cattccgggg    660
ccgtgcaagg acaccatcaa gcagtttcag aatgccgtcg tccgggtccc gatctacgac    720
gtcgcaggtg aaccggaag cggtggatgg tttcacgtcg tcggtttggc tgccttcaag    780
attcagggct accggctgag cggcaacccg gagttcaact ggaacaacga tgttcacggg    840
gcgctgagtt gcaccggcag ctgtcgcggc atcatcggta ccttcgtgaa aattgtcagc    900 ctcgattccgg atctgacgcc gggagggatc gatttcggcg tgagtacgat cagcttgctc    960
gattag                                                                966

<210> SEQ ID NO 59
<211> LENGTH: 738
<212> TYPE: DNA
<213> ORGANISM: Rhodococcus equi

<400> SEQUENCE: 59
ttgagaaccc gaatcattgc tgcgatctgt gcgatcgttc tcgcggtcgc gggaaccctc     60
gccctgatct cgtatgtacg cggggccgat gcccgcgccc tggcgggtac acgcaccgtc    120
gatgtgctcg tcgccgatca gacgattccg aagaacactc ccgccgattc gctcgtggga    180
atggttgtgg tcaagaaact tccggaaatg gcggtgctac ccgaacgggt gaccagtctc    240
gaccaactgt ccggcaaggt cgcgctgacc gacctcctac ctggcgaaca actggtctcg    300
gcgcgattcg ccgacccggc gaccgcccga agtcaggacc agggaggaat ccccgagggg    360
atgcaggagg tgacggttct tctcgagccg caacgcgcac tgggaggcca catcgcgtca    420
ggcgataccg tcggcgtctt catgtccttc tcgccgcccg tcaagaacta cgaaacacat    480
ctgagattgc agaaagtgcg agtcacgcgg gtccagggaa cgttttccaa cgccgacgaa    540
ggggattcgg ccacggtcga ctcgtcgccg agccctgctc ccaccgaggc ctttctcgtc    600
tcgctggcgg tcgacgtgcc gatggcggag cgcgtcgttt tcgccgcgga gcacgggacc    660
atctggcttt ccaatgagcc gctgagttcg aacgaggccg gggcatccgt ggtctccccg    720
gaaggagtgt tccgatga                                                   738

<210> SEQ ID NO 60
<211> LENGTH: 738
<212> TYPE: DNA
<213> ORGANISM: Rhodococcus equi

<400> SEQUENCE: 60
ttgagaaccc gaatcattgc tgcgatctgt gcgatcgttc tcgcggtcgc gggaaccctc     60
gccctgatct cgtatgtacg cggggccgat gcccgcgccc tggcgggtac acgcaccgtc    120
gatgtgctcg tcgccgatca gacgattccg aagaacactc ccgccgattc gctcgtggga    180
atggttgtgg tcaagaaact tccggaaatg gcggtgctac ccgaacgggt gaccagtctc    240
gaccaactgt ccggcaaggt cgcgctgacc gacctcctgc cggcgaaca actggtctcg    300 gcgcgattcg cagacccggc gaccgcccga agtcaggacc agggaggaat ccccgagggg    360
atgcaggagg tgacggttct tctcgagccc caacgcgcac tgggaggcca catcgcgccg    420
ggcgataccg tcggcgtctt catgtccttc tcgccgcccg tcaagaacta cgaaacacat    480
```

```
ctgagattgc agaaagtgcg agtcacgcgg gtccagggaa cgttttccaa cgccgacgaa    540
ggggattcgg ccacggtcga ctcgtcgccg agccctgctc ccaccgaggc ctttctcgtc    600
tcgctggcgg tcgacgtgcc gatggcggag cgcgtcgttt cgccgcggga gcacgggacc    660
atctggcttt ccaatgagcc gctgagttcg aacgaggccg gggcatccgt ggtctccccg    720
gaaggagtgt tccgatga                                                  738
```

<210> SEQ ID NO 61
<211> LENGTH: 738
<212> TYPE: DNA
<213> ORGANISM: Rhodococcus equi

<400> SEQUENCE: 61

```
ttgagaaccc gaatcattgc tgcgatctgt gcgatcgttc tcgcggtcgc gggaaccctc     60
gccctgatct cgtatgtacg cggggccgat gcccgcgccc tggcgggtac acgcaccgtc    120
gatgtgctcg tcgccgatca gacgattccg aagaacactc ccgccgattc gctcgtggga    180
atggttgtgg tcaagaaact tccggaaatg gcggtgctac ccgatcgggt gaccagtctc    240
gaccaactgt ccggcaaggt cgcgctgacc gacctcctgc ctggcgaaca actggtctcg    300
gcgcgattcg tcgacccggc gaccgcccga agtcaggacc agggaggaat ccccgagggg    360
atgcaggagg tgacggttct tctcgagccg caacgcgcac tggaggcca catcgcgtca    420 ggcgataccg tcggcgtctt catgtccttc tcgccgcccg tcaagaacta cgaaacacat    480
ctgagattgc agaaagtgcg agtcacgcgg gtccagggaa cgttctccaa cgccgacgaa    540
ggggattcgg ccacggtcga ctcgtcgccg agccctgctc ccaccgaggc ctttctcgtc    600
tcgctggcgg tcgacgtgcc gatggcggag cgcgtcgttt cgccgcggga gcacgggacc    660
atctggcttt ccaatgagcc gctgagttcg aacgaggccg gggcatccgt ggtctccccg    720
gaaggagtgt tccgatga                                                  738
```

<210> SEQ ID NO 62
<211> LENGTH: 1200
<212> TYPE: DNA
<213> ORGANISM: Rhodococcus equi

<400> SEQUENCE: 62

```
atgagccgca tcgtcctgct gaccgatcgc gacgatttcg cccgccgcgt gtaccacgcc     60
gcggacggca accttctggt gttgccggcg cagccggttc ccgggggcc ggcgcagttg    120 gtcgggctcg gcgtgaccgt gcaacccgaa gttctcgttc tcggtccgga cgtgccggaa    180
gtggagggcc tctccctcgc cggccggatc gatcattcga cgcccggcac cacggtggtt    240
ctggccagtg atgcgggcac cgacgtgtgg ttgcgggcga tgcgcgccgg cgtgcgggac    300
gtgatgtcgc cggaggcgga gatcgcggac gttcgtgcgg tactcgatcg agcgggccag    360
gccgcactgg cgcgacgtca gggggcgagt gcaccggcgg agcagcatgc ggttcaaggg    420
aaggtcatcg tggtcgcgtc gccgaaaggc ggaaccggaa agaccaccgt tgcgacgaat    480
cttgcagtag gactcgcggc ggcagcgcct cactcgacgg tgttggtgga cctcgacgtg    540
cagttcgggg acgttgccag tgctctccag ttggttccgg aacattgcct gaccgacgcc    600
gtcgcgggcc cggccagcca ggacatgatc gtcctcaaga ccgtccttac accccattcc    660
acaggactgc atgcgctgtg tgggtccgac tcgcccgcgg cgggcgacag catcaccggc    720
gagcaggtga gcactctgct gacgcagttg gcggccgaat tccggtacgt ggtcgtcgac    780
```

```
accgcgcccg gtttgctcga acacaccctg gcggcgctcg acctcgctac cgacgtcgtg    840
ttggtgtcgg gtatggacgt gcccagcgtc cgcgggatgc acaaggaact gcagttgctg    900
gcggagctga atctgggtcc ggtcgtgcgg catgtcgtgc tcaactttgc ggatcgacgc    960 gagggctga cggtccagga catccagaac accatcgggg tccccgccga tatcgtgatc   1020
aagcggtcga agccgttgc cctctcgacg aaccggggtg ttccactgct tcagaacccg   1080
ggtcgggatc gcactgcgaa agagttgtgg cgactcgtcg gccgtatcga tccggctccc   1140
gataccacca agggtggacg cgcgcggcat cgggcagccg aggcggtggg ggcgaaatga   1200
```

<210> SEQ ID NO 63
<211> LENGTH: 1200
<212> TYPE: DNA
<213> ORGANISM: Rhodococcus equi

<400> SEQUENCE: 63

```
atgagccgca tcgtcctgct gaccgatcgc gacgattycg cccgccgcgt gtaccacgcc     60
gcggacggca accttctggt gttgccggcg cagccggttc cccgggggcc ggcgcagttg    120
gtcgggctcg gcgtgaccgt gcaacccgac gttctcgttc tcggtccgga cgtgccggaa    180
gtggagggcc tctccctcgc cggccggatc gatcattcga cgcccggcac cacggtggtt    240
ctggccagtg atgcgggcac cgacgtgtgg ttgagggcga tgcgcgccgg cgtgcgggac    300
gtgatgtcgc cggaggcgga gatcgcggac gttcgtgccg tactcgatcg agcaggtcag    360
gccgcgctgg cgcgacgtca gggggcgagt gcaccggcgg agcagcatgc ggttcaaggg    420
aaggtcatcg tggtcgcgtc gccgaaaggc ggaaccggaa agaccaccgt tgcgacgaat    480
cttgcagtcg gactcgcggc ggcagcgcct cactccacgg tgttggtgga cctcgacgtg    540
cagttcggcg acgttgccag tgctctccag ttggttccgg aacattgcct gaccgacgcc    600
gtcgcgagcc cggccagcca ggacatgatc gtcctcaaga ccgtcctgac accccattcc    660
acaggactgc atgcgctgtg tggatcggac tcgcccgcgg cgggcgacag catcaccggc    720
gagcaggtga gcactctgct gacgcagttg gcggccgaat ccggtacgt ggtcgtcgac    780 accgcgcccg gtttgctcga acacaccctg gcggcgctcg accttgctac cgacgtcgtg    840
ttggtgtcgg gtatggacgt gcccagcgtc cgcgggatgc acaaggaact gcaattgctg    900
acggagctga atctgggtcc ggtcgtgcgg catgtcgtgc tcaactttgc ggatcgacgc    960 gagggctga cggtccagga catccagaac accatcgggg tccccgccga tatcgtgatc   1020
aagcgctcga agccgttgc cctctcgacg aaccgggggg ttccactgct tcagaacccg   1080
ggtcgggatc gcactgcgaa agagttgtgg cgactcgtcg gccgtatcga tccggctccc   1140
gataccgcca agggtggacg cgcgcggcat cgggcagccg aggcggtggg tgcgaaatga   1200
```

<210> SEQ ID NO 64
<211> LENGTH: 1200
<212> TYPE: DNA
<213> ORGANISM: Rhodococcus equi

<400> SEQUENCE: 64

```
atgagccgca tcgtcctgct gaccgatcgc gacgatttcg cccgccgcgt gtaccacgcc     60
gcggacggca accttctggt gttgccggcg cagccggttc cccgggggcc ggcgcagttg    120
gtcgggctcg gcgtgaccgt gcaacccgac gttctcgttc tcggtccgga cgtgccggaa    180
gtggagggcc tctccctcgc cggccggatc gatcattcga cgcccggcac cacggtggtt    240
ctggccagtg atgcgggcac cgacgtgtgg ttgagggcga tgcgcgccgg cgtgcgggac    300
```

```
gtgatgtcgc cggaggcgga gatcgcggac gttcgtgccg tactcgatcg agcaggtcag    360
gccgcgctgg cgcgacgtca gggggcgagt gcaccggcgg agcagcatgc ggttcaaggg    420
aaggtcatcg tggtcgcgtc gccgaaaggc ggaaccggaa agaccaccgt tgcgacgaat    480
cttgcagtcg gactcgcggc ggcagcgcct cactccacgg tgttggtgga cctcgacgtg    540
cagttcggcg acgttgccag tgctctccag ttggttccgg aacattgcct gaccgacgcc    600
gtcgcgagcc cggccagcca ggacatgatc gtcctcaaga ccgtcctgac accccattcc    660
acaggactgc atgcgctgtg tggatcggac tcgcccgcgg cgggcgacag cattaccggc    720
gagcaggtga gcactctgct gacgcagttg gcggccgaat tccggtacgt ggtcgtcgac    780
accgcgcccg gtttgctcga acacaccctg gcggcgctcg accttgctac cgacgtcgtg    840
ttggtgtcgg gtatgacgt gcccagcgtc cgcgggatgc acaaggaact gcaattgctg    900
acggagctga atctgggtcc ggtcgtgcgg catgtcgtgc tcaactttgc ggatcgacgc    960 gagggggctga cggtccagga catccagaac accatcgggg tccccgccga tatcgtgatc   1020
aagcgctcga aagccgttgc cctctcgacg aaccgggggg ttccactgct tcagaacccg   1080
ggtcgggatc gcactgcgaa agagttgtgg cgactcgtcg gccgtatcga tccggctccc   1140
gataccgcca agggtggacg cgcgcggcat cgggcagccg aggcggtggg tgcgaaatga   1200

<210> SEQ ID NO 65
<211> LENGTH: 1398
<212> TYPE: DNA
<213> ORGANISM: Rhodococcus equi

<400> SEQUENCE: 65
atgagactgt cccaacggct cgaggccgtg cgcggagccg cacccgtcga agccgccgca     60
ccgatcccgc cggggaagca ggggaaggcg aaaacgtccc tccctccggc cgacgctctc    120
gccgaactga aggaccgtgc gagtgcggcc ctgtacaccc ggatcggcac ccgcttcaac    180
gactcctcgt tgagcgagga gcaactgcat ctcctggtcc gtgaggaact ggccgaaatc    240
gtggagcaag agacgacgcc actcaccttc gacgaacggc agcgcctgct ccgtgaggtt    300
gccgacgagg tactggggca cggaccgctc cagcggctac tggaggaccc gtcggtcacc    360
gagatcatgg tcaacagcca cgacatggtc tacgtcgagc gggacggcac cctcgtccgc    420
agctccgcgc gattcgcgga cgaggcgcac ctgcgtcgcg tgatcgaacg catcgtttcc    480
gccgtcggtc gacggatcga cgaatcgtcc ccgctcgtgg atgcacgctt ggcggatggc    540
tcccgtgtca acgcggtgat cccaccgctc gcattcaacg gctcctcgct caccattcga    600
aagttctcga aagatccgtt ccaggtcgac gatctcatcg ccttcggcac tctctcgcac    660
gagatgccca actgctcga cgcgtgtgtg caggcgcgac tgaacgtcat cgtctcgggc    720
ggcacgggca cggggaagac gacgctgctc aacgtgctct cgtcgttcat tccggaaggg    780
gagcggatcg tcaccatcga ggacgccgtg gaactgcaac ttcagcagga ccacgtcgta    840
cggttggaga gccgaccgcc gaacatcgag ggcaagggtg ccgtcaccat ccgcgacctg    900
gtgcggaact cgctgcgtat gcgtcccgac cgcatcgtgg tggggagtg tcgcggaggc    960 gagagtctcg acatgctgca agcgatgaac accggtcacg acgggtcgct gtcgacggtg   1020
catgcgaatt cgccccgtga cgccatcgcg cgcttggaga cgctcgtgtt gatggcgggc   1080
atggacttgc cgttgcgggc gatcggagg cagattgctt cggcggtcga cgtgatcgtg   1140
cagctcactc gactacgtga cggcactcgg cgagtgaccc acgtgaccga ggtccagggc   1200
```

| | |
|---|---|
| atggagggtg agatcgtcac actgcaggat gccttcctgt cgactacag cgccggcgtc | 1260 |
| gacgcgcgcg ggcgattcct cggcagaccg cagccgacgg gagtgcggcc gcggttcacc | 1320 |
| gacaaattcc gagatctcgg tattgctttg tcgccgagtg ttttcggggt gggagaaccc | 1380 |
| tcccgggggc gggcatga | 1398 |

<210> SEQ ID NO 66
<211> LENGTH: 1398
<212> TYPE: DNA
<213> ORGANISM: Rhodococcus equi

<400> SEQUENCE: 66

| | |
|---|---|
| atgagactgt cccaacggct cgaggccgtg cgcggagccg cacccgtcga agccgccgca | 60 |
| ccgatcccgc cggggaagca ggggaaggcg aagacgtccc tccctccggc cgacgctctc | 120 |
| gccgaactga aggaccgtgc gagtgcggcc ctgtacaccc ggatcggcac ccgcttcaac | 180 |
| gactcctcgt tgagcgagga gcaactgcat ctcctggtcc gtgaggaact ggccgagatc | 240 |
| gtggagcaga gacgacgcc actcaccttc gacgagcggc agcgcctgct ccgtgaggtc | 300 |
| gccgacgagg tactggggca cggaccgctt cagcggctac tggaggaccc gtcggtcacc | 360 |
| gagatcatgg tcaacagcca cgacatggtc tacgtcgagc gggacggcac cctcgttcgc | 420 |
| agctccgcgc gattcgcgga cgaggcgcac ctgcgccgcg tgatcgaacg catcgtttcc | 480 |
| gccgtcggtc gacggatcga cgaatcgtcc ccgctcgtgg atgcacgctt ggcggacggc | 540 |
| tcccgtgtca acgcggtgat cccaccgctc gcattcaacg gctcctcgct caccattcga | 600 |
| aagttctcga aagatccgtt ccaggtcgac gatctcatcg ccttcggcac tctctcgcac | 660 |
| gagatggccg aactgctcga cgcgtgtgtg caggcgcgac tgaacgtcat cgtctcgggc | 720 |
| ggcacgggca cggggaagac gacgctgctc aacgtgctct cgtcgttcat tccggaaggg | 780 |
| gagcggatcg tcaccatcga ggacgccgtg gaactgcaac ttcagcagga ccacgtcgta | 840 |
| cggttggaga ccgaccgcc gaacatcgag ggcaagggcg ccgtcaccat ccgtgacctg | 900 |
| gtgcggaact cgctgcgtat cgtcctgac cgcatcgtgg tggggagtg tcgcggaggc | 960 |
| gagagtctcg acatgctgca agcgatgaac accggtcacg acgggtcgct gtcgacggtg | 1020 |
| catgcgaatt cgccccgtga cgccatcgcg cgcttggaga cgctcgtgtt gatggcgggc | 1080 |
| atggacctgc cgttgcgggc gatccgggag cagattgctt cggcggtcga cgtgatcgtg | 1140 |
| cagctcactc gactacgtga cggcactcgg cgagtgaccc acgtgaccga ggtccagggc | 1200 |
| atggagggtg agatcgtcac cctgcaggat gccttcctgt cgactacag cgccggcgtc | 1260 |
| gacgcgcgcg ggcgattcct cggcagaccg cagccgacgg gagtgcggcc gcggttcacc | 1320 |
| gacaaattcc gagatctcgg tattgctttg tcgccgagtg ttttcggggt gggagaaccc | 1380 |
| tcccgggggc gggcatga | 1398 |

<210> SEQ ID NO 67
<211> LENGTH: 1398
<212> TYPE: DNA
<213> ORGANISM: Rhodococcus equi

<400> SEQUENCE: 67

| | |
|---|---|
| atgagactgt cccaacggct cgaggccgtg cgcggagccg cacccgtcga agcggccgca | 60 |
| ccgatcccgc cggggaagca ggggaaggcg aagacgtccc tccctccggc cgacgctctc | 120 |
| gccgaactga aggaccgtgc gagtgcggcc ctgtacaccc ggatcggcac ccgcttcaac | 180 |
| gactcctcgt tgagcgagga gcaactgcat ctcctggtcc gtgaggaact ggccgaaatc | 240 |

| | |
|---|---|
| gtggagcaag agacgacgcc actcaccttc gacgaacggc agcgcctgct ccgtgaggtc | 300 |
| gccgacgagg tactggggca cggaccgctc cagcggctac tggaggaccc gtcggtcacc | 360 |
| gagatcatgg tcaacagcca cgacatggtc tacgtcgagc gggacggcac cctcgtccgc | 420 |
| agctccgcgc gattcgcgga cgaggcgcac ctgcgtcgcg tgatcgaacg catcgtttcc | 480 |
| gccgtcggtc gacggatcga cgaatcgtcc ccgctcgtgg atgcacgctt ggcggatggc | 540 |
| tcccgtgtca acgcggtgat cccaccgctc gcattcaacg gctcctcgct caccattcga | 600 |
| aagttctcga aagatccgtt ccaggtcgac gatctcatcg ccttcggcac tctctcgcac | 660 |
| gagatggccg aactgctcga cgcgtgtgtg caggcgcgac tgaacgtcat cgtctcgggc | 720 |
| ggcacgggca cggggaagac gacgctgctc aacgtgctct cgtcgttcat tccggaaggg | 780 |
| gagcggatcg tcaccatcga ggacgccgtg gaactgcaac ttcagcagga ccacgtcgta | 840 |
| cggttggaga gccgaccgcc gaacatcgag ggcaagggcg ccgtcaccat ccgcgacctg | 900 |
| gtgcggaact cgctgcgtat gcgtcccgac cgcatcgtgg tggggagtg tcgcggaggc | 960 |
| gagagtctcg acatgctgca agcgatgaac accggtcacg acgggtcgct gtcgacggtg | 1020 |
| catgcgaatt cgccccgtga cgccatcgcg cgcttggaga cgctcgtgtt gatggcgggc | 1080 |
| atggacctgc cgttgcgggc gatccgggag cagattgctt cggcggtcga cgtgatcgtg | 1140 |
| cagctcactc gactacgtga cggcactcgg cgagtgaccc acgtgaccga ggtccagggc | 1200 |
| atggagggtg agatcgtcac cctgcaggat gccttcctgt tcgactacag cgccggcgtc | 1260 |
| gacgcgcgcg ggcgattcct cggcagaccg cagccgaccg gagtgcggcc gcggttcacc | 1320 |
| gacaaattcc gagatctcgg tattgctttg tcgccgagtg ttttcggggt gggagaaccc | 1380 |
| tcccgggggc gggcatga | 1398 |

<210> SEQ ID NO 68
<211> LENGTH: 1869
<212> TYPE: DNA
<213> ORGANISM: Rhodococcus equi
<220> FEATURE:
<221> NAME/KEY: misc_feature
<222> LOCATION: (78)..(80)
<223> OTHER INFORMATION: n is a, c, g, or t

<400> SEQUENCE: 68

| | |
|---|---|
| atgagtcggt gcgtggtggc cgtcgtgctc gccctcggtg cgggtgttct gggaattcct | 60 |
| gccgtagccg cggcgccnnn ggaggctgtc caggtctcgg cggtcgacac gacccggttt | 120 |
| cccgacatcg aggtgtccat cctcgcgccg cccggtatcg aagggcaggc gatcgatccg | 180 |
| ggaacgttcg cgctcaccga gggcggcgtg ccgcgagaga tcgaggtcag gcagcagccg | 240 |
| ggttccgagc aggacatcgt gctcgcaatc gacgtgtccg ggggcatgtc gggtccggcg | 300 |
| ctggacgacg tgaagcgcgc cgcatcggat ttcgtgcggc aggcgccgac cggcgcccac | 360 |
| atcggaatcg tcgcgatctc gtcgacgcca caggtgctct cggaactgac gacggactcc | 420 |
| gaggacctgc tccgcaggat cgacggactg aaggcgggcg gcaacagcgc gatcgcagat | 480 |
| tcggtggtga ccgccgccga gatgctcgag cgcggcgaag cggccaacaa catcctgctt | 540 |
| ctgttgacgg acgcgccga cacgtcgagt gcacactcga tgtcggaact cccgtccgtc | 600 |
| ctgagtcggt cgcgcgcgtc gctgtacgcc gtgcagatgt cgacacccga gacgaactct | 660 |
| gctctcctgc agcaggttgc gcgggagtcg cgcggtcagt acgcgtctgc gggtgatacg | 720 |
| gcggcgctgg gtgcgatcta ccagtcggcc gctcgcgcgc tcggaaacct gtacgtcgtc | 780 |

| | |
|---|---|
| cgataccgat cggaagcgaa cggcgatacc caggtggtgg cgagcgtgcg cagcggcgca | 840 |
| gccggccgag tgagcgatcc gttcccggtg acattgcccg tgtggtgcc gacgccgagc | 900 |
| gtcgtcgccg ggaccgtcga cggtttcttc acgtcttcga cggggctggt gatcgggctc | 960 |
| ctagcgtgct actcggcgct tgcgggaggc gtgctggcgg tcgccggtag agcgcccgcg | 1020 |
| aggatttcgg cagcacgtcg tgggcggcag gacggacggg actcgatgct gtcccgattc | 1080 |
| gcggaacggc tggtgcagtg gatcgatcag aacctgagga gacgcggacg catcgctgcc | 1140 |
| cgcacccagg cgctacagga ggcggggctg aagcttcgtc caggtgactt catcgccctg | 1200 |
| gtcggtgctg cggcgatcac cgctgcggcg atcggtctcc tggcttcggg catcgtggcg | 1260 |
| gcgctcttgc tcgcggcgat cacagtggga ttgtcgagaa tctatctccg tgtgatggcc | 1320 |
| ggtaggcgtc gggccgcgtt cgctgatcag ctcgacgatt ccctgcagct gctggccagc | 1380 |
| aatctccgag ccgggcacag catgctccga gcgctcgatt cccttttcccg agaggcggag | 1440 |
| gtgccgactt cggaggagtt cgctcggatc gtcaacgaga ctcgggtggg acgtgatctc | 1500 |
| aacgaggctc tcgacgacgt ggcccggcgg atgcgaagtg acgatttcaa ctggatagct | 1560 |
| caggcgatcg ccatcaaccg tgaggtcgga ggcgacctcg cggaagtcct cgaccaggtg | 1620 |
| ggcaacacca ttcgagagcg aaatcagatt cgacggcagg tgaaagccct tgctgccgag | 1680 |
| gggaaactgt ccgcctacgt gctgatggcg ctgcccttcg gtctcaccgc atttctgctc | 1740 |
| gtctcgaatc cggactacct gtcgaagttg acgggtagcg ccatcggcta cgtgatgatc | 1800 |
| gcggtggggc tcgtcatgct gaccgtcggt gggctgtgga tgaacaaggt tgtctcggtc | 1860 |
| aagttctag | 1869 |

<210> SEQ ID NO 69
<211> LENGTH: 1872
<212> TYPE: DNA
<213> ORGANISM: Rhodococcus equi
<220> FEATURE:
<221> NAME/KEY: misc_feature
<222> LOCATION: (991)..(996)
<223> OTHER INFORMATION: n is a, c, g, or t

<400> SEQUENCE: 69

| | |
|---|---|
| atgagtcggt gcgtggtggc cgtcgtgctc gccctcggtg cgggtgttct gggaattcct | 60 |
| gccgtagccg cggcggccga gacggaggct gtccaggtct cggcggtcga cacgacccgg | 120 |
| tttcccgaca tcgaggtgtc catcctcgcg ccgcccggta tcgaagggca ggcgatcgat | 180 |
| ccgggaacgt tcgcgctcac cgagggaggc gtgccgcgag agatcgaggt caggcagcag | 240 |
| ccgggttccg agcaggacat cgtgctcgca atcgacgtgt ccgggggcat gtcgggtccg | 300 |
| gcgctggacg acgtgaagcg cgccgcatcg gatttcgtac ggcaggcgcc gaccggcgcc | 360 |
| cacatcggaa tcgtcgcgat ctcgtcgacg ccacaggtgc tctcggaact gacgacggac | 420 |
| tccgaggacc tgctccgcag gatcgacgga ctgaaggcgg gcggcaacag cgcgatcgca | 480 |
| gattcggtgg tgaccgccgc cgagatgctc gagcgcggcg aagcggccaa caacatcctg | 540 |
| cttctgttga cggacggcgc cgacacgtcg agtgcacact cgatgtcgga actcccgtcc | 600 |
| gtcctgagtc ggtcgcgcgc gtcgctgtac gccgtgcaga tgtcgacacc cgagacgaac | 660 |
| tctgctctcc tgcagcaggt tgcgcgggag tcgcgcggtc agtacgcgtc tgcgggtgat | 720 |
| acggccgcgc tgggtgcgat ctaccagtcg gccgctcgcg cgctcggaaa cctgtacgtc | 780 |
| gtccgatacc gatcggaagc gaacggcgat acccaggtgg tggcgagcgt gcgcagcggc | 840 |
| gcagccggcc gagtgagcga tccgttcccg gtgacattgc ccggtgtggt gccgacgccg | 900 |

```
agcgtcgtcg ccgggaccgt cgacggtttc ttcacgtctt cgacggggct ggtgatcggg      960
ctcctagcgt gctactcggc gcttgcggga nnnnnnctgg cggtcgccgg tagagggccc     1020
gcgaggattt cggcagcacg tcgtgggcgg caggacggac gggactcgat gctgtcccga     1080
ttcgcggaac ggctggtgca gtggatcgat cagaacctga ggagacgcgg acgcatcgct     1140
gcccgcaccc aggcgctaca ggaggcgggg ctgaagcttc gtccaggtga cttcatcgcc     1200
ctggtcggtg ctgcgcgat caccgctgcg gcgatcggtc tcctggcttc gggcatcgtg      1260
gcggcgctct tgctcgcggc gatcacagtg ggattgtcga gaatctatct ccgggtgatg     1320
gccggtaggc gtcgggccgc gttcgctgat cagctcgacg attccctgca gctgctggcc     1380
agcaatctcc gagccgggca cagcatgctc cgagcgctcg attccctttc ccgggaggcg     1440
gaggtgccga cttcggagga gttcgctcgg atcgtcaacg agactcgggt gggacgtgat     1500
ctcaacgagt ctctcgacga cgtggcccgg cggatgcgaa gtgacgattt caactggata     1560
gctcaggcga tcgccatcaa ccgtgaggtc ggaggcgacc tcgcggaagt cctcgaccag     1620
gtgggcaaca ccattcgaga gcgaaatcag attcgacggc aggtgaaagc ccttgctgcc     1680
gaggggaaac tgtccgccta cgtgctgatg gcgctgccct tcggtctcac cgcatttctg     1740
ctcgtctcga atccggacta cctgtcgaag ttgacgggta gcgccatcgg ctacgtgatg     1800
atcgcggtgg ggctcgtcat gctgaccgtc ggtgggctgt ggatgaacaa ggttgtctcg     1860
gtcaagttct ag                                                         1872

<210> SEQ ID NO 70
<211> LENGTH: 1872
<212> TYPE: DNA
<213> ORGANISM: Rhodococcus equi

<400> SEQUENCE: 70
atgagtcggt gcgtggtggc cgtcgtgctc gccctcggtg cgggtgttct gggaattcct       60
gccgtagccg cggcggccga gacggaggct gtccaggtct cggcggtcga cacgacccgg      120
tttcccgaca tcgaggtgtc catcctcgcg ccgcccggta tcgaagggca ggcgatcgat      180
ccgggaacgt tcgcgctcac cgagggaggc gtgccgcgag agatcgaggt caggcagcag      240
ccgggttccg agcaggacat cgtgctcgca atcgacgtgt ccgggggcat gtcgggtccg      300
gcgctggacg acgtgaagcg cgccgcatcg gatttcgtgc ggcaggcgcc gaccggcgcc      360
cacatcggaa tcgtcgcgat ctcgtcgacg ccacaggtgc tctcggaact gacgacggac      420
tccgaggacc tgctccgcag gatcgacgga ctgaaggcgg gcggcaacag cgcgatcgca      480
gattcggtgg tgaccgccgc cgagatgctc gagcgcggcg aagcggccaa caacatcctg      540
cttctgttga cggacggcgc cgacacgtcg agtgcacact cgatgtcgga actcccgtcc      600
gtcctgagtc ggtcgcgcgc gtcgctgtac gccgtgcaga tgtcgacgcc cgagacgaac      660
tctgctctcc tgcagcaggt tgcgcggag tcgcgcggtc agtacgcgtc tgcgggtgat       720
acggcggcgc tgggtgcgat ctaccagtcg gccgctcgcg cgctcggaaa cctgtacgtc      780
gtccgatacc gatcggaagc gaacggcgat acccaggtgg tggcgagcgt gcgcagcggc      840
gcagccggcc gagtgagcga tccgttcccg gtgacattgc ccgtgtggt gccgacgccg       900 agcgtcgtcg ccgggaccgt cgacggtttc ttcacgtctt cgacggggct ggtgatcggg      960
ctcctagcgt gctactcggc gcttgcggga ggcgtgctgg cggtcgccgg tagagcgccc     1020
gcgaggattt cggcagcacg tcgtgggcgg caggacggac gggactcgat gctgtcccga     1080
```

| | |
|---|---|
| ttcgcggaac ggctggtgca gtggatcgat cagaacctga ggagacgcgg acgcatcgct | 1140 |
| gcccgaaccc aggcgctaca ggaggcgggg ctgaagcttc gtccaggtga cttcatcgcc | 1200 |
| ctggtcggtg ctgcggcgat caccgctgcg gcgatcggtc tcctggcttc gggcatcgtg | 1260 |
| gcggcgctct tgctcgcggc gatcacagtg ggattgtcga gaatctatct ccgtgtgatg | 1320 |
| gccggtaggc gtcgggccgc gttcgctgat cagctcgacg attccctgca gctgctggcc | 1380 |
| agcaatctcc gagccgggca cagcatgctc cgagcgctcg attcccttc ccgagaggcg | 1440 |
| gaggtgccga cttcggagga gttcgctcgg atcgtcaacg agactcgggt gggacgtgat | 1500 |
| ctcaacgagt ctctcgacga cgtggcccgg cggatgcgaa gtgacgattt caactggata | 1560 |
| gctcaggcga tcgccatcaa ccgtgaggtc ggaggcgacc tcgcggaagt cctcgaccag | 1620 |
| gtcggcaaca ccattcgaga gcgaaatcag attcgacggc aggtgaaagc ccttgctgcc | 1680 |
| gaggggaaac tgtccgccta cgtgctgatg gcgctgccct tcggtctcac cgcatttctg | 1740 |
| ctcgtctcga atccggacta cctgtcgaag ttgacgggta gcgccatcgg ctacgtgatg | 1800 |
| atcgcggtgg ggctcgtcat gctgaccgtc ggtgggctgt ggatgaacaa ggttgtctcg | 1860 |
| gtcaagttct ag | 1872 |

<210> SEQ ID NO 71
<211> LENGTH: 891
<212> TYPE: DNA
<213> ORGANISM: Rhodococcus equi

<400> SEQUENCE: 71

| | |
|---|---|
| gtgattccac cgctggtgct catggcggcg ctgtccgtcg gcggggcgtt gggtgttctg | 60 |
| gtgtggttga cggccggcgc ccgagatcca gaacgcggac ccgcccttca gaacctgcag | 120 |
| tcgcagctgg cgttgccgat tccggagtcg ggaggcgcgc caccgctttc gctcggccga | 180 |
| ttcgtgaagc tgctgtcgcc gcccgggacg atggcccgct tggaacgact gcacatcctt | 240 |
| gccggtcgtc cagcggcgtg ggttccggaa cgggccgcga tggcgaagat cgttctcgcc | 300 |
| gcggccgccg ccctgctcgg ccttctcgcg gtgggtgcgt cgcctggcgt cggccgggtg | 360 |
| ctgttcgctg cggccgccgt cgcgctggcg tatttcgtcc ggaacttct cctgcagagc | 420 |
| aggggcagg agcgccaagc cgcgatcgaa ctggcgcttg ccgacaccct cgaccagatg | 480 |
| acgatcgcag tcgaggcggg cctggggttc gaagccgcca tgcagcgggc gcgaagaac | 540 |
| ggaaagggc cgctggccga ggaattcatc cggacattgc aggacataca gatggggcag | 600 |
| tcgaggcgaa tcgcgtacct ggatcttgcc gccagaacga aagcacccaa cttgcggagg | 660 |
| ttccttcggg ccgtcatcca agccgacgag tacggcgtgg ccatcgccga ggtcctgcgg | 720 |
| acccaggcct cggagatgcg tctgaaacgc cgtcagagtg ctgaggagaa ggcgatgaag | 780 |
| gttccggtga aggtgctgtt ccgttgatg acctgcatcc tgccgaccat cttcatcgtg | 840 |
| atcctgggtc cggcggtgat caacatgatg gaggtcttgg gcggtatgta a | 891 |

<210> SEQ ID NO 72
<211> LENGTH: 891
<212> TYPE: DNA
<213> ORGANISM: Rhodococcus equi

<400> SEQUENCE: 72

| | |
|---|---|
| gtgattccac cgctggtgct catggcggcg ctgtccgtcg gcggggcgtt gggtgttctg | 60 |
| gtgtggttga cggccggcgc ccgagatccg gaacgcggac ccgcccttca gaacctccag | 120 |
| tcgcagctgg cgctgccgat tccggagtcg ggaggcgcgc caccgatttc gctcggccga | 180 |

```
ttcgtgaagc tgctgtcgcc acccgggacg atggcccggt tggaacgact gcacatcctt     240
gccggtcgtc cagcggcgtg ggttccggaa cgggccgcga tggcgaagat cgttctcgcc     300
gcggccgccg ccctgctcgg ccttctcgcg gcgggtgcgt cgcctggcgt cggccgggtg     360
ctgttcgctg cggccgccgt cgcgctggcg tatttcgtcc cggaacttct cctgcagagc     420
agggtgcagg agcgccaagc cgcgatcgaa ctggcgcttg ccgacaccct cgaccagatg     480
acgatcgcag tcgaggcggg cctggggttc gaagccgcaa tgcagcgggc cgcgaagaac     540 ggaaagggc cgctggccga ggaattcatc cggacattgc aggacataca gatggggcag      600
tcgaggcgaa tcgcgtacct ggatcttgcc gccagaacga aagcaccgaa cttgcggagg     660
ttccttcggg ccgtcatcca agccgacgag tacggcgtgg ccatcgccga ggttttgcgg     720
acccaggcct cggagatgcg tctgaaacgc cgtcagagtg ctgaggagaa ggcgatgaag     780
gttccggtga aggtgctgtt tccattgatg acctgcatcc tgccgaccat cttcatcgtg     840
atcctgggtc cggcggtgat caacatgatg gaggtcctgg gcggtatgta a              891

<210> SEQ ID NO 73
<211> LENGTH: 891
<212> TYPE: DNA
<213> ORGANISM: Rhodococcus equi

<400> SEQUENCE: 73
gtgattccac cgctggtgct cgtggcggcg ctgtccgtcg gcggggcgtt gggtgttctg      60
gtgtggttga cggccggcgc ccgagatccg gaacgcggac ccgcccttca gaacctccag     120
tcgcagctgg cgttgccgat tccggtgtcg ggaggcgcgc caccgctttc gctcggccga     180
ttcgtgaagc tgctgtcgcc gcccgggacg atgcccgct tggaacgact gcacatcctt      240
gccggtcgtc cagcggcgtg ggttccggaa cgggccgcga tggcgaagat cgttctcgcc     300
gcggccgccg ccctgctcgg ccttctcgcg gtgggtgcgt cgcctggcgt cggccgggtg     360
ctgttcgctg cggccgccgt cgcgctggcg tatttcgtcc cggaacttct cctgcagagc     420 aggggggcagg agcgccaagc cgcgatcgaa ctggcgcttg ccgacaccct cgaccagatg    480
acgatcgcag tcgaggcggg cctggggttc gaagccgcca tgcagcgggc cgcgaagaac     540 ggaaagggc cgctggccga ggaattcatc cggacattgc aggacataca gatggggcag      600
tcgaggcgaa tcgcgtacct ggatcttgcc gccagaacga aagcacccaa cttgcggagg     660
ttccttcggg ccgtcatcca agccgacgag tacggcgtgg ccatcgccga ggtcctgcgg     720
acccaggcct cggagatgcg tctgaaacgc cgtcagagtg ctgaggagaa ggcgatgaag     780
gttccggtga aggtgctgtt tccgttgatg acctgcatcc tgccgaccat cttcatcgtg     840
atcctgggtc cggcggtgat caacatgatg gaggtcttgg gcggtatgta a              891
```